US008415350B2

(12) United States Patent
Gobbi et al.

(10) Patent No.: US 8,415,350 B2
(45) Date of Patent: Apr. 9, 2013

(54) BENZOYL-PIPERIDINE DERIVATIVES AS DUAL MODULATORS OF THE 5-HT$_{2A}$ AND D$_3$ RECEPTORS

(75) Inventors: Luca Gobbi, Oberwil BL (CH); Georg Jaeschke, Basel (CH); Thomas Luebbers, Loerrach (DE); Olivier Roche, Folgensbourg (FR); Rosa Maria Rodriguez-Sarmiento, Basel (CH); Lucinda Steward, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/233,056

(22) Filed: Sep. 15, 2011

(65) Prior Publication Data

US 2012/0004208 A1 Jan. 5, 2012

Related U.S. Application Data

(62) Division of application No. 11/705,635, filed on Feb. 13, 2007, now Pat. No. 8,039,490.

(30) Foreign Application Priority Data

Feb. 17, 2006 (EP) .................................... 06110112
Apr. 11, 2006 (EP) .................................... 06112464

(51) Int. Cl.
*A61K 31/496* (2006.01)
*A61K 31/5377* (2006.01)
*C07D 401/08* (2006.01)
*C07D 417/08* (2006.01)

(52) U.S. Cl. .................. 514/235.5; 514/227.8; 514/255; 514/326; 544/60; 544/129; 544/359; 546/297; 546/208

(58) Field of Classification Search ............... 514/235.5, 514/227.8, 255, 326; 544/129, 60, 359; 546/208, 546/207
See application file for complete search history.

(56) References Cited

U.S. PATENT DOCUMENTS

| 4,024,264 | A | 5/1977 | Bjork et al. | |
|---|---|---|---|---|
| 7,423,050 | B2 | 9/2008 | Cohen et al. | |
| 7,772,252 | B2 * | 8/2010 | Hendrix et al. ............... | 514/316 |
| 2009/0042943 | A1 | 2/2009 | Gobbi et al. | |
| 2012/0040972 | A1 * | 2/2012 | Gobbi et al. ............... | 514/228.2 |

FOREIGN PATENT DOCUMENTS

| DE | 2536103 | 2/1976 |
|---|---|---|
| EP | 0479601 | 4/1992 |
| EP | 1348434 | 10/2003 |
| JP | 03264579 | 11/1991 |
| WO | 00/58305 | 10/2000 |
| WO | 03/028526 | 4/2003 |
| WO | 03/048154 | 6/2003 |
| WO | 2004/063181 | 7/2004 |

OTHER PUBLICATIONS

Patani et al. "Bioisosterism: a rational . . . " Chem. Rev. 96 p. 3147-3176 (1996).*
Ravine et al. "Conformationally contstrain . . . " j. Med. Chem. 42, p. 2774-2797 (1999).*
Hendrix et al. "Preparation of hetero . . . " CA137:201331 (2002).*
Choi et al., "CA 138:964344" ( 2002).
Drescher et al., "Am. Soc. Neurosci. Online Abstract 894.6" ( 2002).
Porras et al., "Neuropsychopharmacology" 26:311-324 ( 2002).
Harrison et al., "J. Br. J. Psychiatry Suppl." (Suppl. 174), 38:12-22 ( 1999).
Gurevic et al., "Neuropsychopharmacology" 20:60-80 ( 1998).
Missale et al., "Physiol. Rev." 78:189-225 ( 1998).
Pompeiano et al., "Molecular Brain Research" 23:163-178 ( 1994).
Lieberman et al., "N. Engl. J. Med." 353:1209-1223 ( 2005).
Ashby et al., "Synapse" 48:154-156 ( 2003).
Campos et al., "Soc. Neurosci. Online Abstract 322.8" ( 2003).
Deangelis et al., "Curr. Opin. Investig. Drugs" 3:106-112 ( 2002).
Leikin et al., "Med. Toxicol. Adverse Drug Exp." 4:324-350 ( 1989).
Gobbi et al., "CA 147:300997" ( 2007).
Roth et al., "Pharmacol. Ther." 79:231-257 ( 1998).
Bernacka et al., "Tetrahedron Letters" 42:5093-5094 ( 2001).
Reavill et al., "J. Pharmacol. Exp. Ther." 294:1154-1165 ( 2000).
Joyce et al., "Drug Discovery Today" 10(13):917-925 ( 2005).
Arranz et al., "Lancet" 355:1615-1616 ( 2000).
Roth et al., "Nat. Rev. Drug Discov." 3:353-359 ( 2004).
Goldfarb et al., "CA 151:92836" ( 2009).
Watanabe et al., "Chemical and Pharmaceutical Bulletin" (XP001018922), 38(10):2726-2732 ( 1990).
Vorel et al., "J. Neurosci." 22:9595-9603 ( 2002).
Tokuyama et al., "Synthesis" 8:1121-1123 ( 2002).
Pazos et al., "Neuroscience" 21:123-139 ( 1987).
Mancuso et al., "Synthesis":165-185 ( 1981).
Barnes et al., "Neuropharmacology" 38:1083-1152 ( 1999).
Herndon et al., "Journal of Medicinal Chemistry" (XP000941731), 35:4903-4910 ( 1992).
Meltzer et al., "J. Pharmacol. Exp. Ther." 251:238-246 ( 1989).
Gurevic et al., "Arch. Gen. Psychiatry" 54:225-232 ( 1997).
Gobbi et al., "CA 150:214184" ( 2009).
Spurlock et al., "Mol. Psychiatry" 3:42-49 ( 1998).
Patani et al., "Chem. Rev." 96:3147-3176 ( 1996).
Wustrow et al., "Journal of Medicinal Chem." 41:760-771 ( 1998).

* cited by examiner

*Primary Examiner* — Celia Chang
(74) *Attorney, Agent, or Firm* — George W. Johnston; Patricia S. Rocha-Tramaloni; Kimberly J. Prior

(57) ABSTRACT

The present invention relates to compounds of the general formula

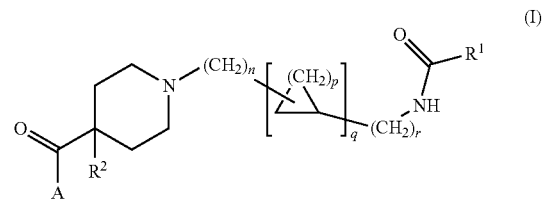

as dual modulators of the 5-HT$_{2a}$ and D$_3$ receptors useful against CNS disorders, wherein A, R$^1$, R$^2$, n, p, q and r are as defined in the specification.

5 Claims, No Drawings

BENZOYL-PIPERIDINE DERIVATIVES AS DUAL MODULATORS OF THE 5-HT$_{2A}$ AND D$_3$ RECEPTORS

PRIORITY TO RELATED APPLICATIONS

This application is a division of U.S. application Ser. No. 11/705,635, filed Feb. 13, 2007, now pending; which claims the benefit of European Application Nos. 06110112.7, filed Feb. 17, 2006, and European Application No. 06112464.0, filed Apr. 11, 2006. The entire contents of the above-identified applications are hereby incorporated by reference.

BACKGROUND OF THE INVENTION

In particular schizophrenia is characterized by complex symptomatology including positive symptoms, (i.e. delusions and hallucinations), and negative symptoms, (i.e. anhedonia, restricted fluency and productivity of thought and speech). In addition it is now well recognized that cognitive impairment is the third major diagnostic category of schizophrenia, characterized by loss in working memory as well as other deficits. Other symptoms include aggressiveness, depression and anxiety (Stahl, S. M. (2000) Essential Psychopharmacology. Neuroscientific Basis and Practical Applications. Cambridge University Press, second edition, Cambridge, UK). The different categories and the clinical features of the disorder are defined in diagnostic schemes such as DSM-IV (Diagnostic and statistical manual of mental disorders, 4$^{th}$ edition) or ICD-10 (International classification of diseases, 10$^{th}$ edition). Currently used medications to treat schizophrenia, bipolar mania and other psychoses, include antipsychotics both typical (D$_2$/D$_3$ preferring) or the more recent atypicals, which exhibit polypharmacology interacting at multiple receptors (eg., D$_1$, D$_2$, D$_3$, D$_4$, 5-HT$_{1A}$, 5-HT$_{2A}$, 5-HT$_{2C}$, H$_1$, M$_1$, M$_2$, M$_4$, etc; Roth, B. L. et al. (2004) Magic shotguns versus magic bullets: selectively non-selective drugs for mood disorders and schizophrenia. Nat. Rev. Drug Discov. 3, 353-359). These antipsychotics, although relatively successful (some patients exhibit treatment resistance) at treating the positive symptoms of schizophrenia, are less effective at treating negative symptoms, cognitive deficits, and associated depression and anxiety, all of which lead to reduced patient quality of life and socioeconomic problems (Lieberman, J. A. et al. Clinical Antipsychotic Trials of Intervention Effectiveness (CATIE) Investigators. (2005) Effectiveness of antipsychotic drugs in patients with chronic schizophrenia. N. Engl. J. Med. 353, 1209-1223). Furthermore, patient compliance is compromised by prevalent side effects such as weight gain, extrapyramidal symptoms (EPS), and cardiovascular effects (Lieberman, J. A. et al. Clinical Antipsychotic Trials of Intervention Effectiveness (CATIE) Investigators. (2005) Effectiveness of antipsychotic drugs in patients with chronic schizophrenia. N. Engl. J. Med. 353, 1209-1223). In the current invention, compounds with high affinity and greater selectivity for D$_3$ and 5-HT$_{2A}$ receptors are described and are proposed to treat psychoses and other diseases, with fewer associated side affects.

Dopamine, a major catecholamine neurotransmitter, is involved in the regulation of a variety of functions which include emotion, cognition, motor functions, and positive reinforcement, (Purves, D. et al. (2004) Neuroscience. Sinauer, third edition, Sunderland, Mass.). The biological activities of dopamine are mediated through G protein-coupled receptors (GPCRs) and in human, five different dopamine receptors D$_1$-D$_5$ have been identified, where the D$_2$-like receptors (D$_2$, D$_3$ and D$_4$) couple to the G-protein G$_{\alpha I}$ (Missale, C. et al. (1998) Dopamine receptors: from structure to function. Physiol. Rev. 78, 189-225). The D$_3$ dopamine receptor is most highly expressed in the nucleus accumbens (Gurevich, E. V., Joyce, J. N. (1999) Distribution of dopamine D$_3$ receptor expressing neurons in the human forebrain: comparison with D$_2$ receptor expressing neurons. Neuropsychopharmacology 20, 60-80), and is proposed to modulate the mesolimbic pathway consisting of neuronal projections from the ventral tegmental area, hippocampus and amygdala to the nucleus accumbens, which projects to the prefrontal and cingulate cortices as well as various thalamic nuclei.

The limbic circuit is thought to be important for emotional behavior and thus D$_3$ receptor antagonists are proposed to modulate psychotic symptoms such as hallucinations, delusions and thought disorder (Joyce, J. N. and Millan, M. J., (2005) Dopamine D$_3$ receptor antagonists as therapeutic agents. Drug Discovery Today, 1 July, Vol. 10, No. 13, 917-25), while these antagonists spare the D$_2$ modulated striatal extrapyramidal system (associated with EPS induction). In addition, it has been reported that drug naive schizophrenic patients show altered levels of D$_3$ receptor expression (Gurevich, E. V. et al. (1997) Mesolimbic dopamine D$_3$ receptors and use of antipsychotics in patients with schizophrenia. A postmortem study. Arch. Gen. Psychiatry 54, 225-232) and dopamine release (Laruelle, M. (2000) Imaging dopamine dysregulation in schizophrenia: implication for treatment. Presented at Workshop Schizophr.: Pathol. Bases and Mech. Antipsychotic Action, Chicago), indicating that a disturbed homeostasis of dopamine plays an important role in the etiology of schizophrenic symptoms.

The neurotransmitter serotonin is implicated in several psychiatric conditions including schizophrenia (Kandel, E. R. et al. (eds.; 2000) Principles of Neural Science, 3$^{rd}$ edition Appleton & Lange, Norwalk, Conn.). The involvement of serotonin in psychotic disorders is suggested by multiple studies which include treatment in humans with the psychotropic drug Lysergic acid (LSD; a serotonin agonist) which can induce schizophrenia-like symptoms such as hallucinations (Leikin, J. B. et al. (1989) Clinical features and management of intoxication due to hallucinogenic drugs. Med. Toxicol. Adverse Drug Exp. 4, 324-350).

Furthermore, altered brain distribution of serotonin receptors as well as an altered serotonergic tone, have been detected in schizophrenic patients (Harrison, P. J. (1999) Neurochemical alterations in schizophrenia affecting the putative receptor targets of atypical antipsychotics. Focus on dopamine (D1, D3, D4) and 5-HT2A receptors. Br. J. Psychiatry Suppl. 38, 12-22).

In mammals serotonin exerts its biological activities through a family of 14 5-HT GPCRs (Barnes, N. M., Sharp, T. (1999) A review of central 5-HT receptors and their function. Neuropharmacology 38, 1083-1152). The 5-HT$_{2A}$ receptor is most prominently expressed in the prefrontal cortex and at lower levels in the basal ganglia and the hippocampus in human brain (Pompeiano, M. et al. (1994) Distribution of the serotonin 5-HT2 receptor family mRNAs: comparison between 5-HT2A and 5-HT2C receptors. Brain Res. Mol. Brain. Res. 23, 163-178; Pazos, A., Probst, A., Palacios, J. M. (1987) Serotonin receptors in the human brain—IV. Autoradiographic mapping of serotonin-2 receptors. Neuroscience 21, 123-139), and is coupled predominantly to the G-protein G$_{\alpha q}$ (Roth, B. L. et al. (1998) 5-Hydroxytryptamine-2-family receptors (5-hydroxytryptamine-2A, 5-hydroxytryptamine-2B, 5-hydroxytryptamine-2C): where structure meets function. Pharmacol. Ther. 79, 231-257).

Genetic linkage studies of a 5-HT$_{2A}$ polymorphism to schizophrenia (Spurlock, G. et al. (1998) A family based association study of T102C polymorphism in 5HT2A and schizophrenia plus identification of new polymorphisms in the promoter. Mol. Psychiatry. 3, 42-49), as well as responsiveness to antipsychotic drugs (Arranz, M. J. et al. (2000) Pharmacogenetic prediction of clozapine response. Lancet 355, 1615-1616), further suggests a role for the 5-$HT_{2A}$ receptor both in the treatment and pathology of psychosis. In addition, dopaminergic neurotransmission appears to be under the afferent regulation of the 5-$HT_{2A}$ receptor (Porras, G. et al. 5-HT2A and 5-HT2C/2B receptor subtypes modulate dopamine release induced in vivo by amphetamine and morphine in both the rat nucleus accumbens and striatum. Neuropsychopharmacology 26, 311-324-2002). Overall 5-$HT_{2A}$ receptor antagonists are proposed to be suitable for the treatment of disorders associated with dysfunctional dopaminergic systems. Moreover, 5-$HT_{2A}$ receptor antagonism has been recognized as beneficial for the treatment of psychosis (reviewed in de Angelis, L. (2002) 5-HT2A antagonists in psychiatric disorders. Curr. Opin. Investig. Drugs 3, 106-112) and indeed is one of the defining features of so-called atypical antipsychotic drugs which are characterized by a relatively high affinity for the 5-$HT_{2A}$-relative to the $D_2$ receptor (Meltzer, H. Y. et al. (1989) Classification of typical and atypical antipsychotic drugs on the basis of dopamine D-1, D-2 and serotonin2 pKi values. J. Pharmacol. Exp. Ther. 251, 238-246).

SUMMARY OF THE INVENTION

The present invention provides compounds of formula (I)

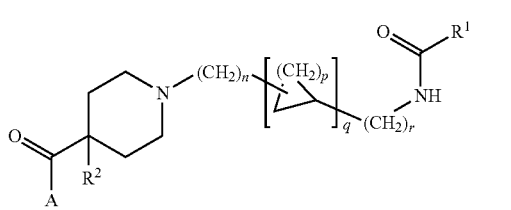

(I)

wherein:
A is aryl or 5 to 6 membered heteroaryl each of which is optionally substituted by one to five substituents selected from the group consisting of halo, $C_{1-6}$-alkyl and $C_{1-6}$-alkoxy;
n is 1, 2, 3 or 4;
p is 1, 2, 3 or 4;
q is 0 or 1;
r is 0, 1, 2 or 3;
$R^1$ is $C_{2-6}$-alkenyl or $C_{2-6}$-alkynyl each of which is optionally substituted by aryl,
or is $C_{1-6}$-alkyl optionally substituted by one to five substituents selected from the group consisting of:
halo,
hydroxy,
$C_{1-6}$-alkyl,
—CO(O)—$C_{1-6}$-alkyl,
$C_{3-10}$-cycloalkyl,
$C_{1-6}$-alkoxy optionally substituted by one, two or three halo or substituted by aryl, aryl optionally substituted by halo or $C_{1-6}$-alkoxy,
5 to 10 membered heteroaryl optionally substituted by $C_{1-6}$-alkyl, and phenoxyl,
or is $C_{1-6}$-alkoxy,
or is $C_{3-10}$-cycloalkyl optionally substituted by one or more $R^a$, or is 5 to 10 membered heterocycloalkyl optionally substituted by one or more $R^a$,
or is aryl optionally substituted by one or more $R^a$,
or is 5 to 10 membered heteroaryl optionally substituted by one or more $R^a$,
or is —$NR^bR^c$, wherein $R^b$ is H or $C_{1-6}$-alkyl and wherein $R^c$ is H, $C_{1-6}$-alkyl or aryl optionally substituted by one or more $R^a$,
wherein $R^a$ is selected from:
halo,
cyano,
oxo,
hydroxy,
halobenzenesulfonyl,
$C_{1-6}$-alkyl optionally substituted by one, two or three substitutents selected from the group consisting of:
5 to 6 membered heterocycloalkyl, and
aryl which is optionally substituted by halo or by $C_{1-6}$-alkoxy,
$C_{1-6}$-haloalkyl,
$C_{1-6}$-haloalkoxy,
$C_{1-6}$-alkoxy optionally substituted by aryl or by 5 to 6 membered heteroaryl each of which is optionally substituted by $C_{1-6}$-alkyl,
aryloxy,
—NH(CO)—$C_{1-6}$-alkyl,
—O(CO)—$C_{1-6}$-alkyl,
$C_{1-6}$-alkylsulfonyl,
aryl,
5 to 6 membered heterocycloalkyl optionally substituted by hydroxy, $C_{1-6}$-alkyl or oxo,
5 to 6 membered heteroaryl optionally substituted by $C_{1-6}$-alkyl or oxo, and di($C_{1-6}$)alkylamino; and
$R^2$ is H, OH, $C_{1-6}$-alkyl or halo;
and pharmaceutically acceptable salts thereof.

The invention also provides pharmaceutical compositions containing compounds of the invention and processes for the preparation of such compounds and compositions.

Compounds of formula (I) according to the invention are dual modulators of the serotonin 5-$HT_{2a}$ and dopamine $D_3$ receptors. The compounds of the invention have high affinity for the dopamine $D_3$ and serotonin (5-hydroxytryptamine; 5-HT) 5-$HT_{2A}$ receptors and are believed to be effective in the treatment of psychotic disorders, as well as other diseases such as depression and anxiety, drug dependence, dementias and memory impairment. Psychotic disorders encompass a variety of diseases, which include schizophrenia, schizoaffective disorders, bipolar disease, mania, psychotic depression, and other psychoses involving paranoia and delusions.

As mentioned hereinabove, the compounds of the invention have high affinity for the dopamine $D_3$ and serotonin 5-$HT_{2A}$ receptors and are expected to be effective in the treatment of psychotic disorders which include schizophrenia, schizoaffective disorders, bipolar disease, mania, psychotic depression, and other psychoses involving paranoia and delusions (Reavill-C, et al. (2000) Pharmacological actions of a novel, high-affinity, and selective human dopamine D3 receptor antagonist, SB-277011-A. JPET 294:1154-1165; Harrison, P. J. (1999) Neurochemical alterations in schizophrenia affecting the putative receptor targets of atypical antipsychotics. Focus on dopamine (D1, D3, D4) and 5-HT2A receptors. Br. J. Psychiatry Suppl. 38, 12-22; de Angelis, L. (2002) 5-HT2A antagonists in psychiatric disorders. Curr. Opin. Investig. Drugs 3, 106-112; Joyce, J. N. and Millan, M. J., (2005) Dopamine D3 receptor antagonists as therapeutic agents. Drug Discovery Today, 1 July, Vol. 10, No. 13, P. 917-25); drug dependency and abuse and withdrawal (Vorel, S. R. et al. (2002) Dopamine D₃ receptor antagonism inhibits cocaine-seeking and cocaine-enhanced brain reward in rats. J. Neurosci., 22, 9595-9603; Campos, A. C. et al. (2003) The dopamine D3 receptor antagonist SB277011A antagonizes nicotine-enhanced brain-stimulation reward in rat. Soc. Neurosci. Abstr., 322.8; Ashby, et al. (2003) Acute administration of the selective D3 receptor antagonist SB-277011-A blocks the acquisition and expression of the conditioned place preference response to heroin in male rats. Synapse, 48, 154-156); anxiety, and depression (Reavill-C et al. (2000) Pharmacological actions of a novel, high-affinity, and selective human dopamine D3 receptor antagonist, SB-277011-A. JPET 294: 1154-1165; Drescher, K. et al. (2002) In vivo effects of the selective dopamine D3 receptor antagonist A-437203. Am. Soc. Neurosci. 894.6).

Compounds of formula (I) can form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate, and methanesulphonate. Preferred are the hydrochloride salts. Also solvates and hydrates of compounds of formula I and their salts form part of the present invention.

Compounds of formula (I) can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula (I) in this invention can be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

"Aryl" represents an aromatic carbocyclic group consisting of one individual ring, or one or more fused rings in which at least one ring is aromatic in nature. Preferred aryl group is phenyl or naphthyl, as well as those specifically illustrated by the examples herein below.

"Aryloxy" denotes an aryl group as defined above which is connected via an oxygen atom.

"$C_{1-6}$-alkyl" denotes a straight- or branched-hydrocarbon carbon chain group containing from 1 to 6 carbon atoms, for example, methyl, ethyl, propyl, isopropyl, isobutyl, sec-butyl, tert-butyl, pentyl, n-hexyl as well as those specifically illustrated by the examples herein below.

"di($C_{1-6}$-alkyl)amino" denotes a nitrogen atom substituted by two $C_{1-6}$-alkyl groups as defined hereinabove. Examples of di($C_{1-6}$-alkyl)amino are dimethylamino, diethylamino, dipropylamino, methylethylamino as well as those groups which are specifically illustrated by the examples herein below.

"$C_{1-6}$-haloalkyl" denotes a $C_{1-6}$-alkyl group as defined above which is substituted by one or more halogen atom. Examples of $C_{1-6}$-haloalkyl include but are not limited to methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Preferred $C_1$-$C_7$-haloalkyl are difluoro- or trifluoro-methyl or ethyl.

"$C_{1-6}$-alkylsulfonyl" denotes a sulfonyl group ($SO_2$) which is substituted by a $C_{1-6}$-alkyl group as defined above.

"halobenzenesulfonyl" denotes a group having the following formula:

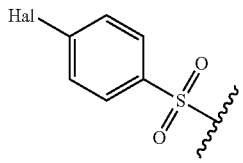

"$C_{1-6}$-alkoxy" denotes an alkyl group as defined above which is connected via an oxygen atom.

"$C_{1-6}$-haloalkoxy" denotes a $C_{1-6}$-alkoxy group as defined above which is substituted by one or more halogen atom. Examples of $C_{1-6}$-haloalkoxy include but are not limited to methoxy or ethoxy, substituted by one or more Cl, F, Br or I atom(s) as well as those groups specifically illustrated by the examples herein below. Preferred $C_1$-$C_7$ haloalkoxy are difluoro- or trifluoro-methoxy or ethoxy.

"Halo" or "Halogen" denotes chlorine, iodine, fluorine and bromine.

"$C_{2-6}$Alkenyl" denotes straight-chain or branched unsaturated hydrocarbon residues with 2-6, preferably 2-4 carbon atoms, such as ethenyl, 2-propenyl, isobutene-1-yl, and those specifically exemplified in the instant patent application.

"$C_{2-6}$Alkynyl" denotes

"$C_{3-10}$-cycloalkyl" denotes a monovalent saturated moiety, consisting of one, two or three carbon rings having 3 to 10 carbon atoms as ring members and includes but is not limited to cyclopropyl, cyclobutyl, cyclopentyl, cyclohexyl, cycloheptyl and polyspiro groups such as bicyclo[2.2.2]octanyl, bicyclo[2.2.1]heptanyl, bicyclo[3.2.1]octanyl or adamantanyl as well as those groups specifically illustrated by the examples herein below.

"5 to 10 membered heteroaryl" means a monocyclic, bicyclic or tricyclic radical of 5 to 10 ring atoms having at least one aromatic ring and furthermore containing one, two, or three ring heteroatoms selected from N, O, and S, the remaining ring atoms being C. Heteroaryl can optionally be substituted with one, two, three or four substituents, wherein each substituent is independently hydroxy, cyano, alkyl, alkoxy, thioalkyl, halo, haloalkyl, hydroxyalkyl, alkoxycarbonyl, amino, acetyl, —NHCOOC(CH₃)₃ or halogen substituted benzyl, or for the non aromatic part of cyclic ring also by oxo, unless otherwise specifically indicated. Examples of heteroaryl moieties include, but are not limited to, optionally substituted imidazolyl, optionally substituted thiophenyl, optionally substituted oxazolyl, optionally substituted isoxazolyl, optionally substituted thiazolyl, optionally substituted pyrazinyl, optionally substituted pyrrolyl, optionally substituted pyridinyl, optionally substituted pyrimidinyl, optionally substituted pyridazinyl, optionally substituted indolyl, optionally substituted isoindolyl, optionally substituted 2,3-dihydroinidolyl, optionally substituted indazolyl, optionally substituted naphthyridinyl, optionally substituted isoquinolinyl, optionally substituted carbazol-9-yl, optionally substituted furanyl, optionally substituted benzofuranyl, optionally substituted quinolinyl, optionally substituted benzo[1,3]dioxolyl, optionally substituted benzo[1,2,3]thiadiazolyl, optionally substituted benzo[b]thiophenyl, optionally substituted 9H-thioxanthenyl, optionally substituted thieno[2,3-c]pyridinyl, optionally substituted 3H-imidazo[4,5,b]pyridinyl, optionally substituted phthalazinyl, optionally substituted 2,3-dihydrobenzo[1,4]dioxinyl, and the like or those which are specifically exemplified herein. Preferred 5 to 10 membered heteroaryls are 5 or 6 membered heteroaryls.

"5 to 10 heterocycloalkyl" means a monovalent saturated heterocyclic moiety, consisting of one, two or three rings, incorporating one, two, or three heteroatoms independently chosen from nitrogen, oxygen and sulfur. Heterocycloalkyl can optionally be substituted with one, two, three or four substituents, wherein each substituent is independently hydroxy, alkyl, alkoxy, thioalkyl, halo, haloalkyl, hydroxyalkyl, alkoxycarbonyl, amino, alkylamino, dialkylamino, aminocarbonyl, or carbonylamino, unless otherwise specifically indicated. Examples of heterocyclic moieties include, but are not limited to, piperidinyl, piperazinyl, homopiperazinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, quinuclidinyl, quinolinyl, isoquinolinyl, benzimidazolyl, chromanyl, thiadiazolylidinyl, benzothiazolidinyl, benzoazolylidinyl, dihydrofuryl, tetrahydrofuryl, dihydropyranyl, tetrahydropyranyl, thiomorpholinyl, dioxothiomorpholinyl thiomorpholinylsulfoxide, thiomorpholinylsulfone, dihydroquinolinyl, dihydrisoquinolinyl, tetrahydroquinolinyl, tetrahydroisoquinolinyl, 1-oxothiomorpholin, 1,1-dioxo-thiomorpholin, 1,4-diazepane, 1,4-oxazepane as well as those groups specifically illustrated by the examples herein below. Preferred 5 to 10 membered heterocycloalkyls are 5 or 6 membered heterocycloalkyls.

"one or more" denotes herein, 1, 2, 3, 4, 5, 6, 7, 8, 9 or 10 and preferably 1, 2, 3, 4 or 5 and still more preferably 1, 2 or 3.

"oxo" denotes a group =O.

"Pharmaceutically acceptable," such as pharmaceutically acceptable carrier, excipient, etc., means pharmacologically acceptable and substantially safe, non-toxic, and neither biologically nor otherwise undesirable to the subject to which the particular compound is administered and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like.

"Therapeutically effective amount" means an amount that is effective to prevent, alleviate or ameliorate symptoms of disease or prolong the survival of the subject being treated.

Also encompassed by the compounds of formula (I) are the compounds of formula (Ia):

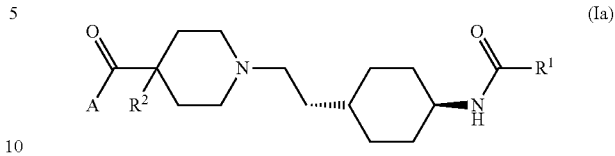

wherein A, $R^1$ and $R^2$ are as defined hereinabove for formula (I).

In a particular embodiment, the compounds of formula (Ia) are those compounds wherein $R^1$ is 5 to 10 membered heteroaryl optionally substituted by one or more $R^a$, for example the following compounds:

2-Methyl-2H-indazole-3-carboxylic acid trans-(4-{2-[4-(4-fluoro-benzoyl)-piperidin-1-yl]-ethyl}-cyclohexyl)-amide;

6-Chloro-2-methyl-quinoline-3-carboxylic acid trans-(4-{2-[4-(4-fluoro-benzoyl)-piperidin-1-yl]-ethyl}-cyclohexyl)-amide;

5-Chloro-1-(3,4-dichloro-benzyl)-6-oxo-1,6-dihydro-pyridine-3-carboxylic acid trans-(4-{2-[4-(4-fluoro-benzoyl)-piperidin-1-yl]-ethyl}-cyclohexyl)-amide;

N-trans-(4-{2-[4-(4-Fluoro-benzoyl)-piperidin-1-yl]-ethyl}-cyclohexyl)-6-methyl-nicotinamide;

[1,8]Naphthyridine-4-carboxylic acid trans-(4-{2-[4-(4-fluoro-benzoyl)-piperidin-1-yl]-ethyl}-cyclohexyl)-amide;

5-Fluoro-1H-indole-2-carboxylic acid (trans-4-{2-[4-(4-fluoro-benzoyl)-piperidin-1-yl]-ethyl}-cyclohexyl)-amide;

5-Trifluoromethoxy-1H-indole-2-carboxylic acid (trans-4-{2-[4-(4-fluoro-benzoyl)-piperidin-1-yl]-ethyl}-cyclohexyl)-amide;

5-Methoxy-1H-indole-2-carboxylic acid trans-(4-{2-[4-(4-fluoro-benzoyl)-piperidin-1-yl]-ethyl}-cyclohexyl)-amide;

Thiophene-2-carboxylic acid trans-(4-{2-[4-(4-fluoro-benzoyl)-piperidin-1-yl]-ethyl}-cyclohexyl)-amide;

3H-Imidazo[4,5-b]pyridine-6-carboxylic acid trans-(4-{2-[4-(4-fluoro-benzoyl)-piperidin-1-yl]-ethyl}-cyclohexyl)-amide;

5-Methanesulfonyl-thiophene-2-carboxylic acid trans-(4-{2-[4-(4-fluoro-benzoyl)-piperidin-1-yl]-ethyl}-cyclohexyl)-amide;

6-Fluoro-N-trans (4-{2-[4-(4-fluoro-benzoyl)-piperidin-1-yl]-ethyl}-cyclohexyl)-nicotinamide;

N-trans (4-{2-[4-(4-Fluoro-benzoyl)-piperidin-1-yl]-ethyl}-cyclohexyl)-6-morpholin-4-yl-nicotinamide;

3-Methyl-chroman-3-carboxylic acid (4-{2-[4-(4-fluoro-benzoyl)-piperidin-1-yl]-ethyl}-cyclohexyl)-amide;

2-Morpholin-4-yl-pyrimidine-5-carboxylic acid (4-{2-[4-(4-fluoro-benzoyl)-piperidin-1-yl]-ethyl}-cyclohexyl)-amide;

6-Morpholin-4-yl-pyridazine-3-carboxylic acid trans-(4-{2-[4-(4-fluoro-benzoyl)-piperidin-1-yl]-ethyl}-cyclohexyl)-amide;

5-Morpholin-4-yl-pyrazine-2-carboxylic acid trans-(4-{2-[4-(4-fluoro-benzoyl)-piperidin-1-yl]-ethyl}-cyclohexyl)-amide;

Benzo[1,3]dioxole-5-carboxylic acid trans-(4-{2-[4-(4-fluoro-benzoyl)-piperidin-1-yl]-ethyl}-cyclohexyl)-amide;

3-Methyl-isoxazole-5-carboxylic acid trans-(4-{2-[4-(4-fluoro-benzoyl)-piperidin-1-yl]-ethyl}-cyclohexyl)-amide;

Trans N-(4-{2-[4-(4-Fluoro-benzoyl)-piperidin-1-yl]-ethyl}-cyclohexyl)-2-methoxy-isonicotinamide;

N-trans (4-{2-[4-(4-Fluoro-benzoyl)-piperidin-1-yl]-ethyl}-cyclohexyl)-6-morpholin-4-yl-nicotinamide;

2,3-Dihydro-benzo[1,4]dioxine-2-carboxylic acid trans-(4-{2-[4-(4-fluoro-benzoyl)-piperidin-1-yl]-ethyl}-cyclohexyl)-amide;

5-(4-Methyl-piperazin-1-yl)-pyridine-2-carboxylic acid trans-(4-{2-[4-(4-fluoro-benzoyl)-piperidin-1-yl]-ethyl}-cyclohexyl)-amide;

5-Morpholin-4-yl-pyridine-2-carboxylic acid trans-(4-{2-[4-(4-fluoro-benzoyl)-piperidin-1-yl]-ethyl}-cyclohexyl)-amide;

5-Phenyl-pyridine-2-carboxylic acid trans-(4-{2-[4-(4-fluoro-benzoyl)-piperidin-1-yl]-ethyl}-cyclohexyl)-amide;

Quinoline-4-carboxylic acid trans-(4-{2-[4-(4-fluoro-benzoyl)-piperidin-1-yl]-ethyl}-cyclohexyl)-amide;

Quinoline-4-carboxylic acid trans-(4-{2-[4-(4-methoxy-benzoyl)-piperidin-1-yl]-ethyl}-cyclohexyl)-amide;

Quinoline-4-carboxylic acid trans-{4-[2-(4-benzoyl-4-hydroxy-piperidin-1-yl)-ethyl]-cyclohexyl}-amide;

Quinoline-4-carboxylic acid trans-{4-[2-(4-benzoyl-4-fluoro-piperidin-1-yl)-ethyl]-cyclohexyl}-amide;

Quinoline-4-carboxylic acid trans-(4-{2-[4-(3,4-dichloro-benzoyl)-piperidin-1-yl]-ethyl}-cyclohexyl)-amide;

2,3-Dihydro-indole-1-carboxylic acid trans-(4-{2-[4-(4-fluoro-benzoyl)-piperidin-1-yl]-ethyl}-cyclohexyl)-amide;

6-Trifluoromethyl-2,3-dihydro-indole-1-carboxylic acid trans-(4-{2-[4-(4-fluoro-benzoyl)-piperidin-1-yl]-ethyl}-cyclohexyl)-amide;

1,3-Dihydro-isoindole-2-carboxylic acid trans-(4-{2-[4-(4-fluoro-benzoyl)-piperidin-1-yl]-ethyl}-cyclohexyl)-amide;

3,4-Dihydro-1H-isoquinoline-2-carboxylic acid trans-(4-{2-[4-(4-fluoro-benzoyl)-piperidin-1-yl]-ethyl}-cyclohexyl)-amide;

Quinoline-4-carboxylic acid trans-(4-{2-[4-(4-fluoro-benzoyl)-4-hydroxy-piperidin-1-yl]-ethyl}-cyclohexyl)-amide;

5-Methanesulfonyl-thiophene-2-carboxylic acid (4-{2-[4-(2,4-difluoro-benzoyl)-piperidin-1-yl]-ethyl}-cyclohexyl)-amide;

Chroman-3-carboxylic acid (4-{2-[4-(2,4-difluoro-benzoyl)-piperidin-1-yl]-ethyl}-cyclohexyl)-amide;

(R)-Chroman-3-carboxylic acid (4-{2-[4-(2,4-difluoro-benzoyl)-piperidin-1-yl]-ethyl}-cyclohexyl)-amide;

(S)-Chroman-3-carboxylic acid (4-{2-[4-(2,4-difluoro-benzoyl)-piperidin-1-yl]-ethyl}-cyclohexyl)-amide;

N-trans (4-{2-[4-(2,4-Difluoro-benzoyl)-piperidin-1-yl]-ethyl}-cyclohexyl)-6-morpholin-4-yl-nicotinamide;

2,3-Dihydro-indole-1-carboxylic acid (4-{2-[4-(2,4-difluoro-benzoyl)-piperidin-1-yl]-ethyl}-cyclohexyl)-amide;

Quinoline-4-carboxylic acid trans-(4-{2-[4-(3,4-difluoro-benzoyl)-piperidin-1-yl]-ethyl}-cyclohexyl)-amide;

5-Methanesulfonyl-thiophene-2-carboxylic acid (4-{2-[4-(3,4-difluoro-benzoyl)-piperidin-1-yl]-ethyl}-cyclohexyl)-amide;

Chroman-3-carboxylic acid (4-{2-[4-(3,4-difluoro-benzoyl)-piperidin-1-yl]-ethyl}-cyclohexyl)-amide;

5-Methanesulfonyl-thiophene-2-carboxylic acid (4-{2-[4-(2-chloro-4-fluoro-benzoyl)-piperidin-1-yl]-ethyl}-cyclohexyl)-amide;

Quinoline-4-carboxylic acid (4-{2-[4-(2-chloro-benzoyl)-piperidin-1-yl]-ethyl}-cyclohexyl)-amide;

Chroman-3-carboxylic acid (trans-4-{2-[4-(4-chloro-benzoyl)-piperidin-1-yl]-ethyl}-cyclohexyl)-amide;

Chroman-3-carboxylic acid (trans-4-{2-[4-(3-chloro-thiophene-2-carbonyl)-piperidin-1-yl]-ethyl}-cyclohexyl)-amide; and Benzo[1,3]dioxole-5-carboxylic acid (trans-4-{2-[4-(5-chloro-thiophene-2-carbonyl)-piperidin-1-yl]-ethyl}-cyclohexyl)-amide.

In a particular embodiment, the compounds of formula (Ia) are those compounds wherein $R^1$ is —$NR^bR^c$, wherein $R^b$ is H or $C_{1-6}$-alkyl and wherein $R^c$ is H, $C_{1-6}$-alkyl or aryl optionally substituted by one or more $R^a$, for example the following compounds:

Trans 1-(2,4-Dichloro-phenyl)-3 (4-{2-[4-(4-fluoro-benzoyl)-piperidin-1-yl]-ethyl}-cyclohexyl)-urea;

Trans 1-(4-Chloro-phenyl)-3 (4-{2-[4-(4-fluoro-benzoyl)-piperidin-1-yl]-ethyl}-cyclohexyl)-urea;

Trans 1-(4-Ethoxy-phenyl)-3-(4-{2-[4-(4-fluoro-4-(4-fluoro-benzoyl)-piperidin-1-yl]-ethyl}-cyclohexyl)-urea;

Trans 1-(4-{2-[4-(4-Fluoro-benzoyl)-piperidin-1-yl]-ethyl}-cyclohexyl)-3-p-tolyl-urea;

Trans 1-(4-Chloro-phenyl)-3 (4-{2-[4-(4-fluoro-benzoyl)-piperidin-1-yl]-ethyl}-cyclohexyl)-1-methyl-urea;

Trans-3 (4-{2-[4-(4-Fluoro-benzoyl)-piperidin-1-yl]-ethyl}-cyclohexyl)-1,1-dimethyl-urea;

Trans 1-(4-Chloro-phenyl)-3-(4-{2-[4-(4-fluoro-4-(4-fluoro-benzoyl)-piperidin-1-yl]-ethyl}-cyclohexyl)-urea;

Trans 1-(4-Chloro-phenyl)-3-(4-{2-[4-(2,4-difluoro-benzoyl)-piperidin-1-yl]-ethyl}-cyclohexyl)-urea; and Trans 1-(4-{2-[4-(2,4-Difluoro-benzoyl)-piperidin-1-yl]-ethyl}-cyclohexyl)-3-(4-ethoxy-phenyl)-urea.

In a particular embodiment, the compounds of formula (Ia) are those compounds wherein $R^1$ is aryl optionally substituted by one or more $R^a$, for example the following compounds:

4-Chloro-N-trans (4-{2-[4-(4-fluoro-benzoyl)-piperidin-1-yl]-ethyl}-cyclohexyl)-benzamide;

4-(3,5-Dimethyl-isoxazol-4-ylmethoxy)-N-trans (4-{2-[4-(4-fluoro-benzoyl)-piperidin-1-yl]-ethyl}-cyclohexyl)-benzamide;

N-trans-(4-{2-[4-(4-Fluoro-benzoyl)-piperidin-1-yl]-ethyl}-cyclohexyl)-4-trifluoromethyl-benzamide;

N-trans-(4-{2-[4-(4-Fluoro-benzoyl)-piperidin-1-yl]-ethyl}-cyclohexyl)-4-morpholin-4-yl-benzamide;

N-trans-(4-{2-[4-(4-Fluoro-benzoyl)-piperidin-1-yl]-ethyl}-cyclohexyl)-3-(5-methyl-[1,2,4]oxadiazol-3-yl)-benzamide;

N-trans-(4-{2-[4-(4-Fluoro-benzoyl)-piperidin-1-yl]-ethyl}-cyclohexyl)-4-pyrrol-1-yl-benzamide;

4-Ethoxy-N-trans (4-{2-[4-(4-fluoro-benzoyl)-piperidin-1-yl]-ethyl}-cyclohexyl)-benzamide;

4-Acetylamino-N-trans (4-{2-[4-(4-fluoro-benzoyl)-piperidin-1-yl]-ethyl}-cyclohexyl)-benzamide;

N-trans-(4-{2-[4-(4-Fluoro-benzoyl)-piperidin-1-yl]-ethyl}-cyclohexyl)-4-(3-methyl-5-oxo-4,5-dihydro-pyrazol-1-yl)-benzamide;

4-Cyano-N-trans (4-{2-[4-(4-fluoro-benzoyl)-piperidin-1-yl]-ethyl}-cyclohexyl)-benzamide;

N-trans-(4-{2-[4-(4-Fluoro-benzoyl)-piperidin-1-yl]-ethyl}-cyclohexyl)-4-pyrazol-1-yl-benzamide;

2,4-Dichloro-N-trans (4-{2-[4-(4-fluoro-benzoyl)-piperidin-1-yl]-ethyl}-cyclohexyl)-benzamide;

4-(4-Chloro-benzenesulfonyl)-N-trans (4-{2-[4-(4-fluoro-benzoyl)-piperidin-1-yl]-ethyl}-cyclohexyl)-benzamide;
N-trans-(4-{2-[4-(4-Fluoro-benzoyl)-piperidin-1-yl]-ethyl}-cyclohexyl)-4-trifluoromethoxy-benzamide;
N-trans-(4-{2-[4-(4-Fluoro-benzoyl)-piperidin-1-yl]-ethyl}-cyclohexyl)-4-(1,1,2,2-tetrafluoro-ethoxy)-benzamide;
N-trans (4-{2-[4-(4-Fluoro-benzoyl)-piperidin-1-yl]-ethyl}-cyclohexyl)-4-pyridin-3-yl-benzamide;
N-trans (4-{2-[4-(4-Fluoro-benzoyl)-piperidin-1-yl]-ethyl}-cyclohexyl)-4-pyridin-4-yl-benzamide;
N-trans (4-{2-[4-(4-Fluoro-benzoyl)-piperidin-1-yl]-ethyl}-cyclohexyl)-4-pyridin-2-yl-benzamide;
N-trans (4-{2-[4-(4-Fluoro-benzoyl)-piperidin-1-yl]-ethyl}-cyclohexyl)-4-(4-methyl-piperazin-1-yl)-benzamide;
N-trans (4-{2-[4-(4-Fluoro-benzoyl)-piperidin-1-yl]-ethyl}-cyclohexyl)-4-phthalazin-1-yl-benzamide;
N-trans (4-{2-[4-(4-Fluoro-benzoyl)-piperidin-1-yl]-ethyl}-cyclohexyl)-3-methoxy-4-pyridin-2-yl-benzamide;
Biphenyl-4-carboxylic acid (4-{2-[4-(4-fluoro-benzoyl)-piperidin-1-yl]-ethyl}-cyclohexyl)-amide;
2-Fluoro-N-trans (4-{2-[4-(4-fluoro-benzoyl)-piperidin-1-yl]-ethyl}-cyclohexyl)-4-morpholin-4-yl-benzamide;
4-(3,3-Dimethyl-2-oxo-azetidin-1-yl)-N-trans (4-{2-[4-(4-fluoro-benzoyl)-piperidin-1-yl]-ethyl}-cyclohexyl)-benzamide;
N-trans (4-{2-[4-(4-Fluoro-benzoyl)-piperidin-1-yl]-ethyl}-cyclohexyl)-4-morpholin-4-ylmethyl-benzamide;
4-tert-Butoxy-N-trans (4-{2-[4-(4-fluoro-benzoyl)-piperidin-1-yl]-ethyl}-cyclohexyl)-benzamide;
4-Dimethylamino-N-trans (4-{2-[4-(4-fluoro-benzoyl)-piperidin-1-yl]-ethyl}-cyclohexyl)-benzamide;
4-(1,1-Dioxo-6-thiomorpholin-4-yl)-N-trans (4-{2-[4-(4-fluoro-benzoyl)-piperidin-1-yl]-ethyl}-cyclohexyl)-benzamide;
3-Fluoro-N-trans (4-{2-[4-(4-fluoro-benzoyl)-piperidin-1-yl]-ethyl}-cyclohexyl)-4-morpholin-4-yl-benzamide;
N-trans (4-{2-[4-(4-Fluoro-benzoyl)-piperidin-1-yl]-ethyl}-cyclohexyl)-4-(3-hydroxy-pyrrolidin-1-yl)-benzamide;
N-trans (4-{2-[4-(4-Fluoro-benzoyl)-piperidin-1-yl]-ethyl}-cyclohexyl)-4-(4-hydroxy-piperidin-1-yl)-benzamide;
N-trans (4-{2-[4-(4-Fluoro-benzoyl)-piperidin-1-yl]-ethyl}-cyclohexyl)-4-thiomorpholin-4-yl-benzamide; N-trans (4-{2-[4-(4-Fluoro-benzoyl)-piperidin-1-yl]-ethyl}-cyclohexyl)-4-piperidin-1-yl-benzamide;
N-trans (4-{2-[4-(4-Fluoro-benzoyl)-piperidin-1-yl]-ethyl}-cyclohexyl)-2-morpholin-4-yl-benzamide;
N-trans (4-{2-[4-(4-Fluoro-benzoyl)-4-hydroxy-piperidin-1-yl]-ethyl}-cyclohexyl)-3-(5-methyl-[1,2,4]oxadiazol-3-yl)-benzamide;
N-trans (4-{2-[4-(2,4-Difluoro-benzoyl)-piperidin-1-yl]-ethyl}-cyclohexyl)-4-ethoxy-benzamide;
N-trans (4-{2-[4-(2,4-Difluoro-benzoyl)-piperidin-1-yl]-ethyl}-cyclohexyl)-3-(5-methyl-[1,2,4]oxadiazol-3-yl)-benzamide;
4-Chloro-N-(4-{2-[4-(2,4-difluoro-benzoyl)-piperidin-1-yl]-ethyl}-cyclohexyl)-benzamide;
Biphenyl-4-carboxylic acid (4-{2-[4-(2,4-difluoro-benzoyl)-piperidin-1-yl]-ethyl}-cyclohexyl)-amide;
N-(4-{2-[4-(2,4-Difluoro-benzoyl)-piperidin-1-yl]-ethyl}-cyclohexyl)-4-morpholin-4-yl-benzamide
4-Cyano-N-trans (4-{2-[4-(3,4-difluoro-benzoyl)-piperidin-1-yl]-ethyl}-cyclohexyl)-benzamide;
N-trans (4-{2-[4-(3,4-Difluoro-benzoyl)-piperidin-1-yl]-ethyl}-cyclohexyl)-4-pyrrol-1-yl-benzamide;
N-trans (4-{2-[4-(3,4-Difluoro-benzoyl)-piperidin-1-yl]-ethyl}-cyclohexyl)-4-morpholin-4-yl-benzamide;
N-trans (4-{2-[4-(2-Chloro-4-fluoro-benzoyl)-piperidin-1-yl]-ethyl}-cyclohexyl)-4-morpholin-4-yl-benzamide;
4-Chloro-N-trans (4-{2-[4-(2-chloro-4-fluoro-benzoyl)-piperidin-1-yl]-ethyl}-cyclohexyl)-benzamide;
N-trans (4-{2-[4-(2,4-Dichloro-benzoyl)-piperidin-1-yl]-ethyl}-cyclohexyl)-4-morpholin-4-yl-benzamide; and
N-(trans-4-{2-[4-(4-Chloro-benzoyl)-piperidin-1-yl]-ethyl}-cyclohexyl)-4-morpholin-4-yl-benzamide.

In a particular embodiment, the compounds of formula (Ia) are those compounds wherein $R^1$ is $C_{3-10}$-cycloalkyl optionally substituted by one or more $R^a$, for example the following compounds:

Cyclopropanecarboxylic acid trans-(4-{2-[4-(4-fluoro-benzoyl)-piperidin-1-yl]-ethyl}-cyclohexyl)-amide;
Cyclohexanecarboxylic acid trans-(4-{2-[4-(4-fluoro-benzoyl)-piperidin-1-yl]-ethyl}-cyclohexyl)-amide;
Adamantane-1-carboxylic acid trans-(4-{2-[4-(4-fluoro-benzoyl)-piperidin-1-yl]-ethyl}-cyclohexyl)-amide;
2-Cyclopropyl-N-trans (4-{2-[4-(4-fluoro-benzoyl)-piperidin-1-yl]-ethyl}-cyclohexyl)-acetamide;
2-Methyl-cyclopropanecarboxylic acid trans-(4-{2-[4-(4-fluoro-benzoyl)-piperidin-1-yl]-ethyl}-cyclohexyl)-amide;
4-Methoxy-cyclohexanecarboxylic acid trans-(4-{2-[4-(4-fluoro-benzoyl)-piperidin-1-yl]-ethyl}-cyclohexyl)-amide;
4-Hydroxy-cyclohexanecarboxylic acid trans-(4-{2-[4-(4-fluoro-benzoyl)-piperidin-1-yl]-ethyl}-cyclohexyl)-amide;
(1S,4R)-Bicyclo[2.2.1]heptane-2-carboxylic acid trans-(4-{2-[4-(4-fluoro-benzoyl)-piperidin-1-yl]-ethyl}-cyclohexyl)-amide;
(1R,4R)-7,7-Dimethyl-2-oxo-bicyclo[2.2.1]heptane-1-carboxylic acid trans-(4-{2-[4-(4-fluoro-benzoyl)-piperidin-1-yl]-ethyl}-cyclohexyl)-amide;
4-Trifluoromethyl-cyclohexanecarboxylic acid trans-(4-{2-[4-(4-fluoro-benzoyl)-piperidin-1-yl]-ethyl}-cyclohexyl)-amide;
1-Methyl-cyclohexanecarboxylic acid trans-(4-{2-[4-(4-fluoro-benzoyl)-piperidin-1-yl]-ethyl}-cyclohexyl)-amide;
4-Methyl-cyclohexanecarboxylic acid trans-(4-{2-[4-(4-fluoro-benzoyl)-piperidin-1-yl]-ethyl}-cyclohexyl)-amide;
6-Hydroxy-bicyclo[2.2.2]octane-2-carboxylic acid trans-(4-{2-[4-(4-fluoro-benzoyl)-piperidin-1-yl]-ethyl}-cyclohexyl)-amide;
1-Trifluoromethyl-cyclopropanecarboxylic acid trans-(4-{2-[4-(4-fluoro-benzoyl)-piperidin-1-yl]-ethyl}-cyclohexyl)-amide;
3-Chloro-cyclobutanecarboxylic acid trans-(4-{2-[4-(4-fluoro-benzoyl)-piperidin-1-yl]-ethyl}-cyclohexyl)-amide;
1-Hydroxy-cyclopropanecarboxylic acid (trans-4-{2-[4-(4-fluoro-benzoyl)-piperidin-1-yl]-ethyl}-cyclohexyl)-amide;
Cyclobutanecarboxylic acid trans-(4-{2-[4-(4-fluoro-benzoyl)-piperidin-1-yl]-ethyl}-cyclohexyl)-amide;
4-Hydroxy-cyclohexanecarboxylic acid trans-(4-{2-[4-(4-fluoro-benzoyl)-piperidin-1-yl]-ethyl}-cyclohexyl)-amide;
2,2-Difluoro-cyclopropanecarboxylic acid trans-(4-{2-[4-(4-fluoro-benzoyl)-piperidin-1-yl]-ethyl}-cyclohexyl)-amide;
Cyclopropanecarboxylic acid (4-{2-[4-(2,4-difluoro-benzoyl)-piperidin-1-yl]-ethyl}-cyclohexyl)-amide;

Cyclobutanecarboxylic acid (4-{2-[4-(2,4-difluoro-benzoyl)-piperidin-1-yl]-ethyl}-cyclohexyl)-amide;
4-Trifluoromethyl-cyclohexanecarboxylic acid trans-(4-{2-[4-(2,4-difluoro-benzoyl)-piperidin-1-yl]-ethyl}-cyclohexyl)-amide;
Cyclopropanecarboxylic acid (4-{2-[4-(3,4-difluoro-benzoyl)-piperidin-1-yl]-ethyl}-cyclohexyl)-amide;
2,2-Difluoro-cyclopropanecarboxylic acid (4-{2-[4-(3,4-difluoro-benzoyl)-piperidin-1-yl]-ethyl}-cyclohexyl)-amide; and
Cyclopropanecarboxylic acid trans-(4-{2-[4-(2-chloro-4-fluoro-benzoyl)-piperidin-1-yl]-ethyl}-cyclohexyl)-amide.

In a particular embodiment, the compounds of formula (Ia) are those compounds wherein $R^1$ is 5 to 10 membered heterocycloalkyl optionally substituted by one or more $R^a$, for example the following compounds:
Tetrahydro-pyran-4-carboxylic acid trans-(4-{2-[4-(4-fluoro-benzoyl)-piperidin-1-yl]-ethyl}-cyclohexyl)-amide;
Tetrahydro-furan-3-carboxylic acid trans-(4-{2-[4-(4-fluoro-benzoyl)-piperidin-1-yl]-ethyl}-cyclohexyl)-amide;
Morpholine-4-carboxylic acid trans-(4-{2-[4-(4-fluoro-benzoyl)-piperidin-1-yl]-ethyl}-cyclohexyl)-amide;
3-Phenoxy-pyrrolidine-1-carboxylic acid trans-(4-{2-[4-(4-fluoro-benzoyl)-piperidin-1-yl]-ethyl}-cyclohexyl)-amide;
1,1-Dioxo-thiomorpholine-4-carboxylic acid trans-(4-{2-[4-(4-fluoro-benzoyl)-piperidin-1-yl]-ethyl}-cyclohexyl)-amide;
Tetrahydro-furan-3-carboxylic acid trans-(4-{2-[4-fluoro-4-(4-fluoro-benzoyl)-piperidin-1-yl]-ethyl}-cyclohexyl)-amide;
Tetrahydro-furan-3-carboxylic acid trans-(4-{2-[4-(2,4-difluoro-benzoyl)-piperidin-1-yl]-ethyl}-cyclohexyl)-amide;
(S)-Tetrahydro-furan-3-carboxylic acid (4-{2-[4-(2,4-difluoro-benzoyl)-piperidin-1-yl]-ethyl}-cyclohexyl)-amide
(R)-Tetrahydro-furan-3-carboxylic acid (4-{2-[4-(2,4-difluoro-benzoyl)-piperidin-1-yl]-ethyl}-cyclohexyl)-amide
4-Phenyl-piperazine-1-carboxylic acid trans-(4-{2-[4-(2,4-difluoro-benzoyl)-piperidin-1-yl]-ethyl}-cyclohexyl)-amide
Morpholine-4-carboxylic acid (4-{2-[4-(2,4-difluoro-benzoyl)-piperidin-1-yl]-ethyl}-cyclohexyl)-amide
Pyrrolidine-1-carboxylic acid (4-{2-[4-(2,4-difluoro-benzoyl)-piperidin-1-yl]-ethyl}-cyclohexyl)-amide
Tetrahydro-furan-3-carboxylic acid trans-(4-{2-[4-(3,4-difluoro-benzoyl)-piperidin-1-yl]-ethyl}-cyclohexyl)-amide
Tetrahydro-pyran-4-carboxylic acid (4-{2-[4-(3,4-difluoro-benzoyl)-piperidin-1-yl]-ethyl}-cyclohexyl)-amide
Tetrahydro-furan-3-carboxylic acid trans-(4-{2-[4-(2-chloro-4-fluoro-benzoyl)-piperidin-1-yl]-ethyl}-cyclohexyl)-amide;
Tetrahydro-pyran-4-carboxylic acid (4-{2-[4-(2-chloro-4-fluoro-benzoyl)-piperidin-1-yl]-ethyl}-cyclohexyl)-amide; and
Tetrahydro-pyran-4-carboxylic acid (trans-4-{2-[4-(4-chloro-benzoyl)-piperidin-1-yl]-ethyl}-cyclohexyl)-amide.

In a particular embodiment, the compounds of formula (Ia) are those compounds wherein $R^1$ is $C_{1-6}$-alkyl optionally substituted by one to five substituents selected from the group consisting of:
halo,
hydroxy,
$C_{1-6}$-alkyl,
—CO(O)—$C_{1-6}$-alkyl,
$C_{3-10}$-cycloalkyl,
$C_{1-6}$-alkoxy optionally substituted by one, two or three halo or substituted by aryl,
aryl optionally substituted by halo or $C_{1-6}$-alkoxy,
5 to 10 membered heteroaryl optionally substituted by $C_{1-6}$-alkyl, and
phenoxyl,
for example the following compounds:
N-trans (4-{2-[4-(4-Fluoro-benzoyl)-piperidin-1-yl]-ethyl}-cyclohexyl)-3-methoxy-propionamide;
2-(4-Chloro-phenyl)-N-trans (4-{2-[4-(4-fluoro-benzoyl)-piperidin-1-yl]-ethyl}-cyclohexyl)-isobutyramide;
3-Ethoxy-N-trans (4-{2-[4-(4-fluoro-benzoyl)-piperidin-1-yl]-ethyl}-cyclohexyl)-propionamide;
3,3,3-Trifluoro-N-trans (4-{2-[4-(4-fluoro-benzoyl)-piperidin-1-yl]-ethyl}-cyclohexyl)-propionamide;
N-trans (4-{2-[4-(4-Fluoro-benzoyl)-piperidin-1-yl]-ethyl}-cyclohexyl)-propionamide;
2,2,2-Trifluoro N-(4-{2-[4-(4-fluoro-benzoyl)-piperidin-1-yl]-ethyl}-cyclohexyl)-acetamide;
N-trans (4-{2-[4-(4-Fluoro-benzoyl)-piperidin-1-yl]-ethyl}-cyclohexyl)-butyramide;
N-trans (4-{2-[4-(4-Fluoro-benzoyl)-piperidin-1-yl]-ethyl}-cyclohexyl)-3-methoxy-butyramide;
N-(4-{2-[4-(4-Fluoro-benzoyl)-piperidin-1-yl]-ethyl}-cyclohexyl)-3-phenoxy-propionamide;
N-(4-{2-[4-(4-Fluoro-benzoyl)-piperidin-1-yl]-ethyl}-cyclohexyl)-3-hydroxy-2,2-dimethyl-propionamide;
2-Benzo[d]isoxazol-3-yl-N-(4-{2-[4-(4-fluoro-benzoyl)-piperidin-1-yl]-ethyl}-cyclohexyl)-acetamide;
N-trans (4-{2-[4-(4-Fluoro-benzoyl)-piperidin-1-yl]-ethyl}-cyclohexyl)-2-(3-methyl-isoxazol-5-yl)-acetamide;
2-(3,5-Dimethoxy-phenyl)-N-trans (4-{2-[4-(4-fluoro-benzoyl)-piperidin-1-yl]-ethyl}-cyclohexyl)-acetamide;
2-Benzo[1,3]dioxol-5-yl-N-trans (4-{2-[4-(4-fluoro-benzoyl)-piperidin-1-yl]-ethyl}-cyclohexyl)-acetamide;
Acetic acid trans-(4-{2-[4-(4-fluoro-benzoyl)-piperidin-1-yl]-ethyl}-cyclohexylcarbamoyl)-methyl ester;
N-trans-(4-{2-[4-(4-Fluoro-benzoyl)-piperidin-1-yl]-ethyl}-cyclohexyl)-acetamide;
N-trans (4-{2-[4-Fluoro-4-(4-fluoro-benzoyl)-piperidin-1-yl]-ethyl}-cyclohexyl)-acetamide;
N-trans (4-{2-[4-Fluoro-4-(4-fluoro-benzoyl)-piperidin-1-yl]-ethyl}-cyclohexyl)-3-methoxy-propionamide;
Trans N-(4-{2-[4-(4-Fluoro-benzoyl)-4-methyl-piperidin-1-yl]-ethyl}-cyclohexyl)-acetamide;
N-trans (4-{2-[4-(2,4-Difluoro-benzoyl)-piperidin-1-yl]-ethyl}-cyclohexyl)-3-methoxy-propionamide;
N trans-(4-{2-[4-(2,4-Difluoro-benzoyl)-piperidin-1-yl]-ethyl}-cyclohexyl)-propionamide;
N-trans (4-{2-[4-(2,4-Difluoro-benzoyl)-piperidin-1-yl]-ethyl}-cyclohexyl)-acetamide;
N-trans (4-{2-[4-(2,4-Difluoro-benzoyl)-piperidin-1-yl]-ethyl}-cyclohexyl)-2-(3-methyl-isoxazol-5-yl)-acetamide;
N-(4-{2-[4-(2,4-Difluoro-benzoyl)-piperidin-1-yl]-ethyl}-cyclohexyl)-2-hydroxy-acetamide;
(R)—N-Trans (4-{2-[4-(2,4-Difluoro-benzoyl)-piperidin-1-yl]-ethyl}-cyclohexyl)-2-methoxy-propionamide;
2-Benzyloxy-N-trans (4-{2-[4-(2,4-difluoro-benzoyl)-piperidin-1-yl]-ethyl}-cyclohexyl)-acetamide;
N-trans (4-{2-[4-(3,4-Difluoro-benzoyl)-piperidin-1-yl]-ethyl}-cyclohexyl)-butyramide;
2-Cyclopropyl-N-(4-{2-[4-(3,4-difluoro-benzoyl)-piperidin-1-yl]ethyl}-cyclohexyl)-acetamide;
N-trans (4-{2-[4-(3,4-Difluoro-benzoyl)-piperidin-1-yl]-ethyl}-cyclohexyl)-2-(3-methyl-isoxazol-5-yl)-acetamide;
2-Benzyloxy-N-trans (4-{2-[4-(2-chloro-4-fluoro-benzoyl)-piperidin-1-yl]-ethyl}-cyclohexyl)-acetamide;

N-trans (4-{2-[4-(2-Chloro-4-fluoro-benzoyl)-piperidin-1-yl]-ethyl}-cyclohexyl)-butyramide;
N-trans (4-{2-[4-(2-Chloro-4-fluoro-benzoyl)-piperidin-1-yl]-ethyl}-cyclohexyl)-2-cyclopropyl-acetamide;
N-trans (4-{2-[4-(2-Chloro-4-fluoro-benzoyl)-piperidin-1-yl]-ethyl}-cyclohexyl)-propionamide;
N-trans (4-{2-[4-(2-Chloro-4-fluoro-benzoyl)-piperidin-1-yl]-ethyl}-cyclohexyl)-3-methoxy-propionamide;
N-trans (4-{2-[4-(2-Chloro-4-fluoro-benzoyl)-piperidin-1-yl]-ethyl}-cyclohexyl)-acetamide;
N-trans (4-{2-[4-(2-Chloro-benzoyl)-piperidin-1-yl]-ethyl}-cyclohexyl)-acetamide;
N-Trans (4-{2-[4-(2,4-Dichloro-benzoyl)-piperidin-1-yl]-ethyl}-cyclohexyl)-acetamide;
N-Trans (4-{2-[4-(2,5-Dichloro-benzoyl)-piperidin-1-yl]-ethyl}-cyclohexyl)-acetamide;
N-Trans (4-{2-[4-(4-Fluoro-2-methyl-benzoyl)-piperidin-1-yl]-ethyl}-cyclohexyl)-acetamide;
N-{trans-4-[2-(4-Benzoyl-piperidin-1-yl)-ethyl]-cyclohexyl}-acetamide;
N-(trans-4-{2-[4-(3-Chloro-thiophene-2-carbonyl)-piperidin-1-yl]-ethyl}-cyclohexyl)-acetamide;
N-(trans-4-{2-[4-(5-Chloro-thiophene-2-carbonyl)-piperidin-1-yl]-ethyl}-cyclohexyl)-acetamide; and
N-(trans-4-{2-[4-(5-Fluoro-thiophene-2-carbonyl)-piperidin-1-yl]-ethyl}-cyclohexyl)-acetamide.

In a particular embodiment, the compounds of formula (Ia) are those compounds wherein $R^1$ is $C_{1-6}$-alkoxy, for example the following compounds:
Trans (4-{2-[4-(4-Fluoro-benzoyl)-piperidin-1-yl]-ethyl}-cyclohexyl)-carbamic acid methyl ester; and
4-Ethoxy-N-trans (4-{2-[4-fluoro-4-(4-fluoro-benzoyl)-piperidin-1-yl]-ethyl}-cyclohexyl)-benzamide.

In a particular embodiment, the compounds of formula (Ia) are those compounds wherein $R^1$ is $C_{2-}$-alkenyl or $C_{2-6}$-alkynyl substituted by aryl, for example the following compound:
3-Phenyl-propynoic acid (4-{2-[4-(4-fluoro-benzoyl)-piperidin-1-yl]-ethyl}-cyclohexyl)-amide.

Also encompassed by the compounds of formula (I) are the compounds of formula (Ib):

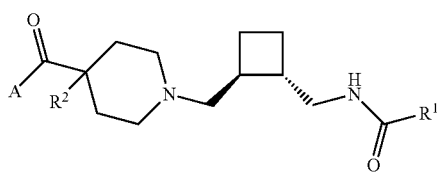

(Ib)

wherein A, $R^1$ and $R^2$ are as defined hereinabove for formula (I), for example the following compounds:
N-{Trans-2-[4-(4-Fluoro-benzoyl)-piperidin-1-ylmethyl]-cyclobutylmethyl}-3-(5-methyl-[1,2,4]oxadiazol-3-yl)-benzamide;
2-(4-Chloro-phenyl)-N-{Trans-2-[4-(4-fluoro-benzoyl)-piperidin-1-ylmethyl]-cyclobutylmethyl}-isobutyramide; and
1-(4-Chloro-phenyl)-3-{trans-2-[4-(4-fluoro-benzoyl)-piperidin-1-ylmethyl]-cyclobutylmethyl}-urea.

Also encompassed by the compounds of formula (I) are the compounds of formula (Ic):

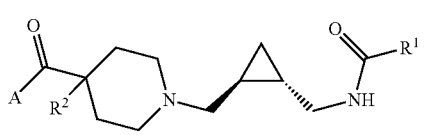

(Ic)

wherein A, $R^1$ and $R^2$ are as defined hereinabove for formula (I), for example the following compounds:
N-{Trans-2-[4-(4-Fluoro-benzoyl)-piperidin-1-ylmethyl]-cyclopropylmethyl}-3-(5-methyl-[1,2,4]oxadiazol-3-yl)-benzamide;
2-(4-Chloro-phenyl)-N-{Trans-2-[4-(4-fluoro-benzoyl)-piperidin-1-ylmethyl]-cyclopropylmethyl}-isobutyramide;
4-Chloro-N-{Trans-2-[4-(4-fluoro-benzoyl)-piperidin-1-ylmethyl]-cyclopropylmethyl}-benzamide; and
1-(4-Chloro-phenyl)-3-{Trans-2-[4-(4-fluoro-benzoyl)-piperidin-1-ylmethyl]-cyclopropylmethyl}-urea.

Also encompassed by the compounds of formula (I) are the compounds of formula (Id):

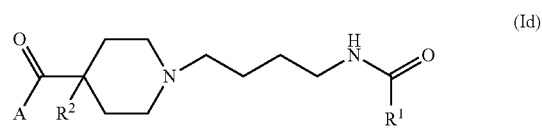

(Id)

wherein A, $R^1$ and $R^2$ are as defined hereinabove for formula (I), for example the following compounds:
4-Ethoxy-N-4-[4-(4-fluoro-benzoyl)-piperidin-1-yl]-butyl}-benzamide;
N-{4-[4-(4-Fluoro-benzoyl)-piperidin-1-yl]-butyl}-3-(5-methyl-[1,2,4]oxadiazol-3-yl)-benzamide;
Tetrahydro-furan-3-carboxylic acid {4-[4-(4-fluoro-benzoyl)-piperidin-1-yl]-butyl}-amide;
1-(4-Chloro-phenyl)-3-{4-[4-(4-fluoro-benzoyl)-piperidin-1-yl]-butyl}-urea; and
1-(4-Ethoxy-phenyl)-3-{4-[4-(4-fluoro-benzoyl)-piperidin-1-yl]-butyl}-urea.

A further aspect of the present invention is the process for the manufacture of compounds of formula (Ia) as defined above, which process comprises reacting a compound of the formula II:

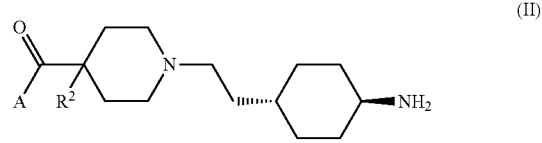

(II)

wherein A and $R^2$ are as defined hereinabove,
a) either with an acid of the formula III:

$$HOOCR^1 \quad \text{(III)}$$

in the presence of a coupling reagent such as O-benzotriazol-1-yl-N,N,N',N'-tetramethyluronium tetrafluoroborate (TBTU) in a suitable solvent like, e.g. dimethylformamide (DMF) or dioxane, in the presence of a base (e.g. triethylamine or diisopropylethylamine) to obtain a compound of the formula (Ia):

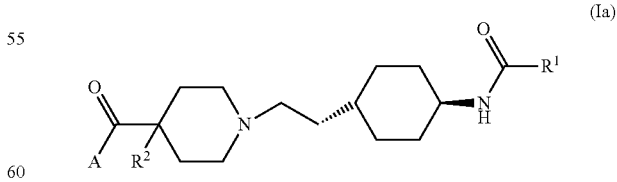

(Ia)

wherein:
$R^1$ is $C_{2-6}$-alkenyl or $C_{2-6}$-alkynyl substituted by aryl,
or is $C_{1-6}$-alkyl optionally substituted by one to five substituents selected from the group consisting of:
halo,
hydroxy, C$_{1-6}$-alkyl,
—CO(O)—C$_{1-6}$-alkyl,
C$_{3-10}$-cycloalkyl,
C$_{1-6}$-alkoxy optionally substituted by one, two or three halo or substituted by aryl,
aryl optionally substituted by halo or C$_{1-6}$-alkoxy,
5 to 10 membered heteroaryl optionally substituted by C$_{1-6}$-alkyl, and
phenoxyl,
or is C$_{1-6}$-alkoxy,
or is C$_{3-10}$-cycloalkyl optionally substituted by one or more R$^a$,
or is 5 to 10 membered heterocycloalkyl optionally substituted by one or more R$^a$,
or is aryl optionally substituted by one or more R$^a$,
or is 5 to 10 membered heteroaryl optionally substituted by one or more R$^a$,
b) or with an isocyanate or a reactive intermediate such as para nitrophenyl carbamate, in a suitable solvent like, e.g. dimethylformamide (DMF) or acetonitrile, in the presence of a base (e.g. triethylamine or diisopropylethylamine) to obtain a compound of the formula (Ia):

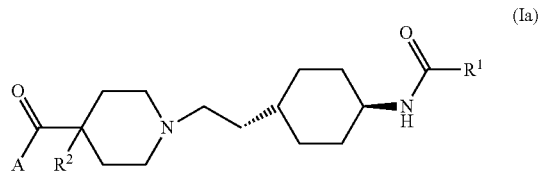

(Ia)

wherein
R$^1$ is —NR$^b$R$^c$, wherein R$^b$ is H or C$_{1-6}$-alkyl and wherein R$^c$ is H, C$_{1-6}$-alkyl or aryl optionally substituted by one or more R$^a$;
or is 5 to 10 membered heterocycloalkyl containing a nitrogen atom attached to the carbonyl group of (Ia) to which R$^1$ is attached, optionally substituted by one or more R$^a$,
or is 5 to 10 membered heteroaryl containing a nitrogen atom attached to the carbonyl group of (Ia) to which R$^1$ is attached, optionally substituted by one or more R$^a$ and if desired,
converting the compound obtained into a pharmaceutically acceptable acid addition salt.

The preparation of compounds of formula (I) of the present invention can be carried out in sequential or convergent synthetic routes. Syntheses of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the description or in the examples, or by methods known in the art.

In the following schemes, A, R$^1$ and R$^2$ are as described hereinabove.

Scheme 1

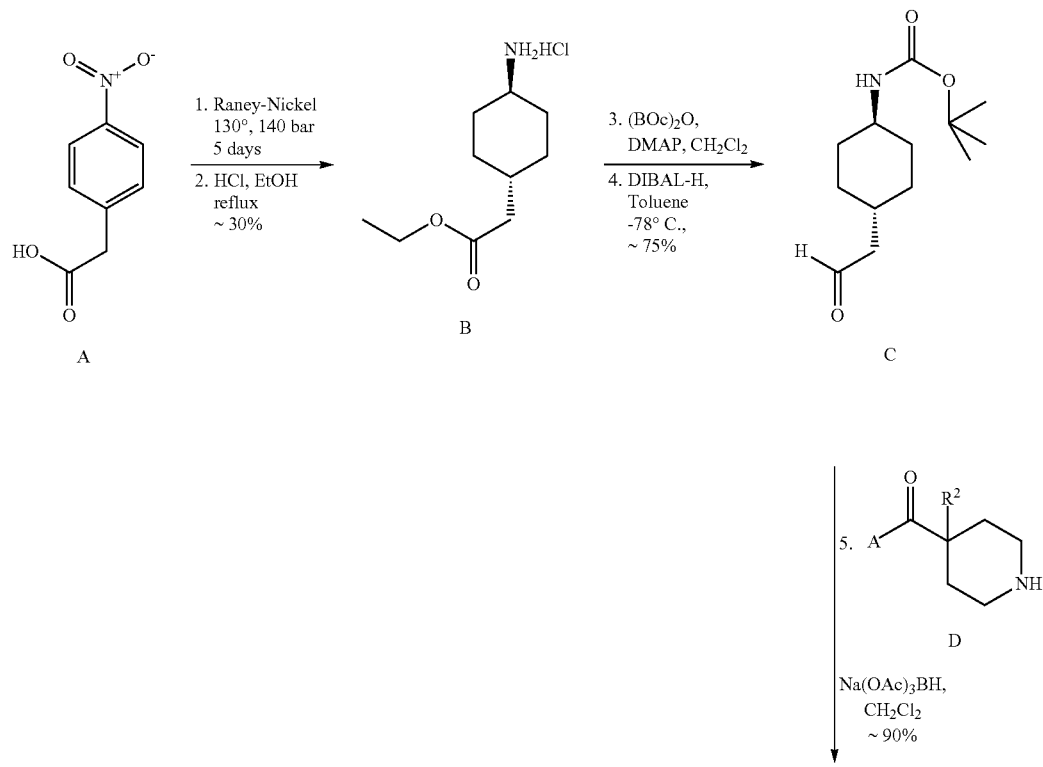

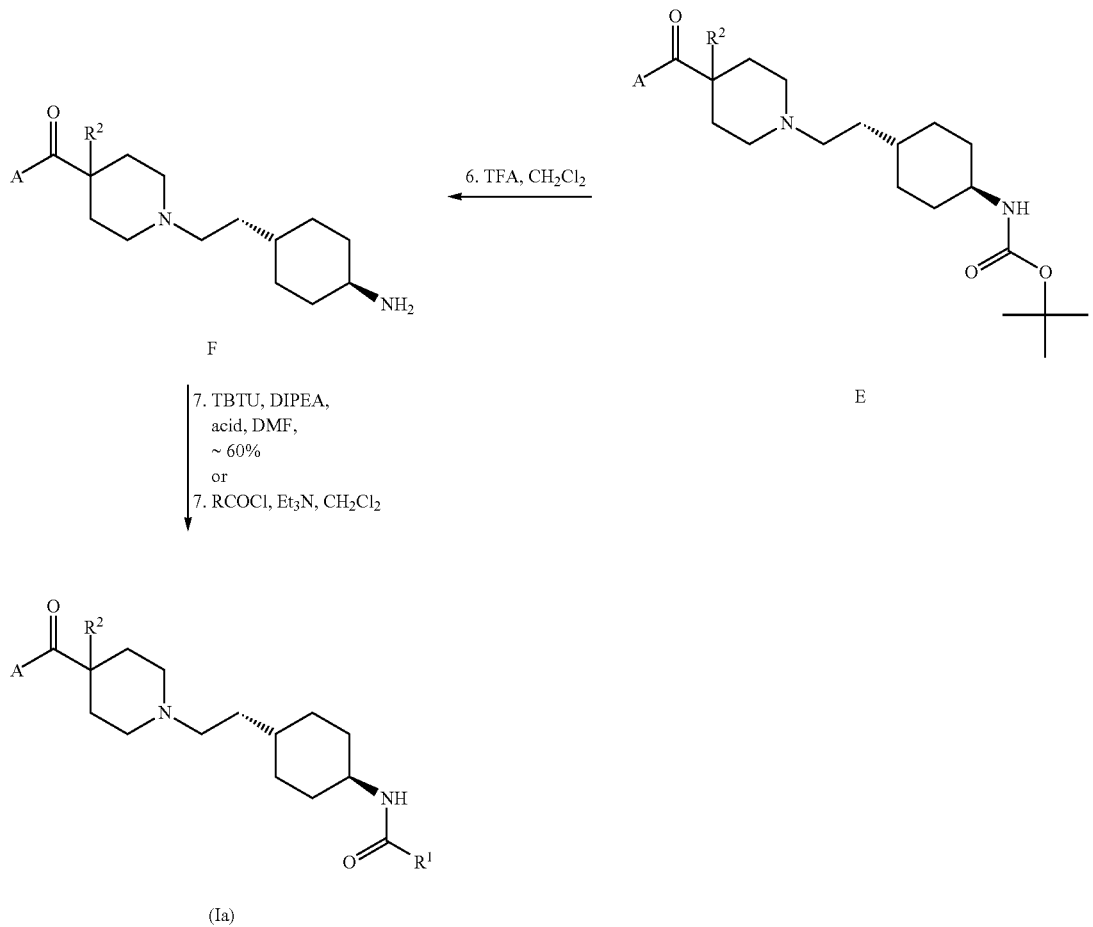

Heteroaryl or benzoyl-piperidin-1-yl trans-ethyl-cyclohexyl-amides or trans-1,4-cyclohexyl ethyl derivates of formula (Ia) can be prepared as depicted in scheme 1 starting from 4-nitro-phenylacetic acid that was hydrogenated using raney nickel as catalyst. The hydrogenation with nickel leads preferentially to the desired trans-isomer (according to Journal of Medicinal Chemistry, 1998, 41, 760-771). Preparing the ethyl ester according to methods known to those skilled in the art and described in the mentioned literature (e.g by treatment with ethanol on the presence of an acid such as HCl) and crystallizing the HCl salt resolves the cis/trans mixture and results in the isolation of the pure trans amino ester chloride B. Reaction with a protecting group such as tert-butyl dicarbonate on the presence of a base like triethylamine and a catalyst like dimethylaminopyridine and reduction with diisobutylaluminium hydride (DIBAL-H) in an appropriate solvent such as, e.g. toluene at −78° C. gives the aldehyde C which can be used without purification on the next step. Reductive amination of aldehyde C with a substituted phenyl or heteroaryl piperidin-4-yl-methanone D either commercially available or accessible by methods described in references by methods described in this patent or by methods known in the art in the presence of a solvent like dichloromethane or 1,2-dichlorethane and a reducing agent such as sodium triacetoxy borohydride yields intermediate E. Removal of the Boc protective group under acidic conditions such as trifluoroacetic acid or hydrochloric acid in a suitable solvent such as, e.g. THF, EtOAc or dichlormethane yields the trans-amino cyclohexyl ethyl intermediate F (usually the TFA or hydrochloride salt). The coupling of the amine intermediate F with carboxylic acids (either commercially available or accessible by methods described in references or by methods known in the art) is widely described in literature (e.g. Comprehensive Organic Transformations: A Guide to Functional Group Preparations, 2nd Edition, Richard C. Larock. John Wiley & Sons, New York, N.Y. 1999) and can be accomplished by employing the usage of coupling reagents such as, e.g. N,N'-carbonyldiimidazole (CDI) or O-benzotriazol-1-yl-N,N,N',N'-tetramethyluronium tetrafluoroborate (TBTU) in a suitable solvent like, e.g. dimethylformamide (DMF) or dioxane in the presence of a base (e.g. triethylamine or diisopropylethylamine) to yield compounds of formula (Ia). In other cases an acid chloride can also be used in the presence of a base (e.g. triethylamine or diisopropylethylamine) in a solvent like dichloromethane.

Scheme 2

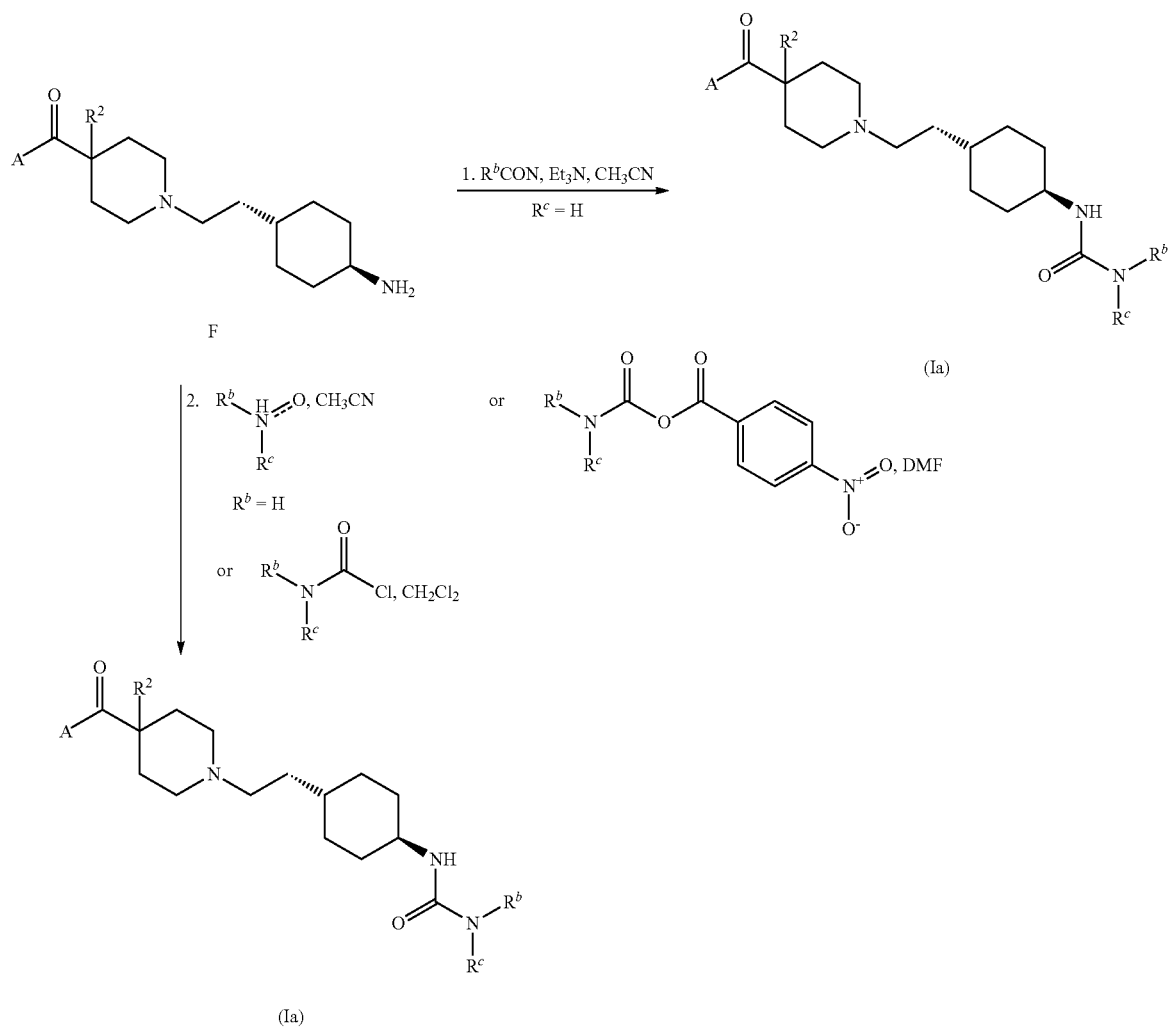

In other examples the intermediate F can also react with an isocyanate (when $R^c$=H) or a reactive intermediate ($R^c \neq H$) such as an appropriate commercial available acid chloride or a para nitro carbamate prepared by methods known in the art or using triphosgene in the presence of a suitable solvent like, e.g. acetonitrile or dichloromethane and of a base (e.g. triethylamine or diisopropylethylamine) to obtain a compound of the formula (Ia) as described on the scheme 2 above.

Scheme 3

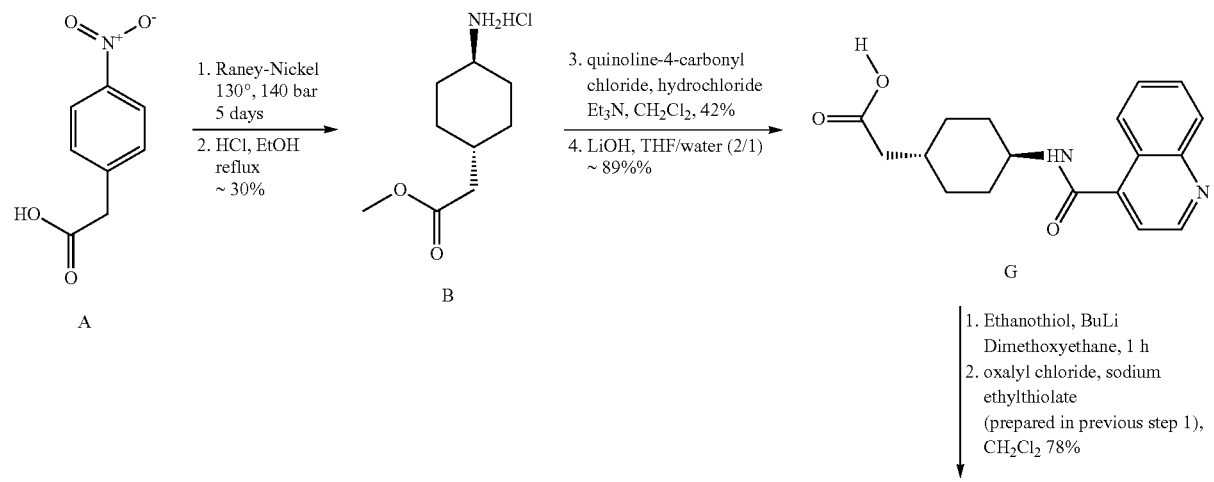

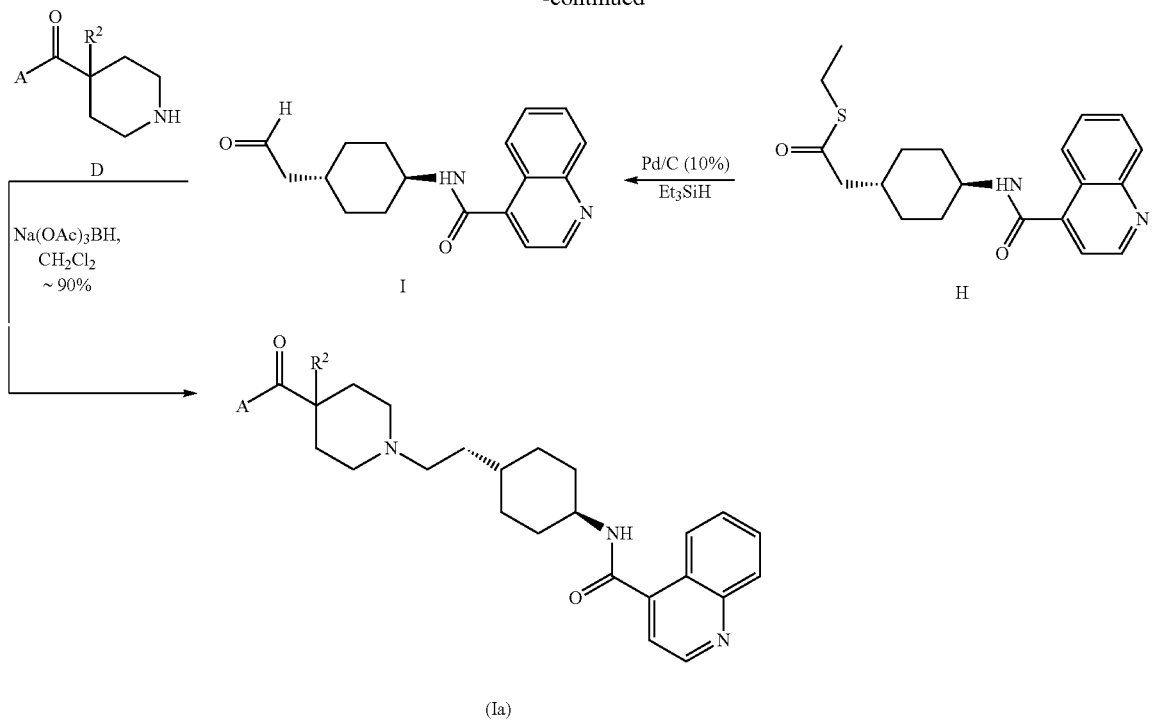

In some cases the phenyl or heteroaryl piperidin-4-yl-methanone D can be coupled in a reductive amination step with a more elaborated aldehyde I according to scheme 3. We used in some cases the quinoline-4-carboxylic acid [4-(2-oxo-ethyl)-cyclohexyl]-amide. The preparation of quinoline-4-carboxylic acid [4-(2-oxo-ethyl)-cyclohexyl]-amide I is described on scheme 2 starting from 4-nitro-phenylacetic acid A that was hydrogenated as already described on scheme 1 using raney nickel and preparing the trans-amino ethyl ester chloride B as already also described on scheme 1. In this case instead of performing the reaction with a protecting group installing reagent such as tert-butyl dicarbonate the amine or amine hydrochloride can reacted with quinoline-4-carbonyl chloride in the presence of a base such as triethylamine in solvent such as dichloromethane to obtain trans-{4-[(quinoline-4-carbonyl)-amino]-cyclohexyl}-acetic acid ethyl ester. Hydrolysis of the ester function under acid or basic conditions such as lithium hydroxide in a solvent mixture such as THF:water gives the corresponding acid G. The preparation of acid intermediates in order to make reductions is known in literature (e.g. T. Fukuyama et. al., Synthesis 2000, 8, 1121-1123). In this case reaction of the acid with sodium ethylthiolate prepared previously from ethanothiol and a base such as butyllithium in a solvent such as dimethoxyethane yields trans-{4-[(quinoline-4-carbonyl)-amino]-cyclohexyl}-thio-acetic acid S-ethyl ester (H) that can be reduced with palladium on charcoal and triethylsilane in a solvent like acetone/methylenchloride (1:1) mixture to obtain the desired trans-quinoline-4-carboxylic acid [4-(2-oxo-ethyl)-cyclohexyl]-amide (I) that can be used in a reductive amination using a reducing agent such as sodium triacetoxy borohydride in a solvent such as dichloromethane to obtain directly trans-quinoline-4-carboxylic acid (4-{2-[4-(4-fluoro-benzoyl)-piperidin-1-yl]-ethyl}-cyclohexyl)-amide (Ia).

Scheme 4

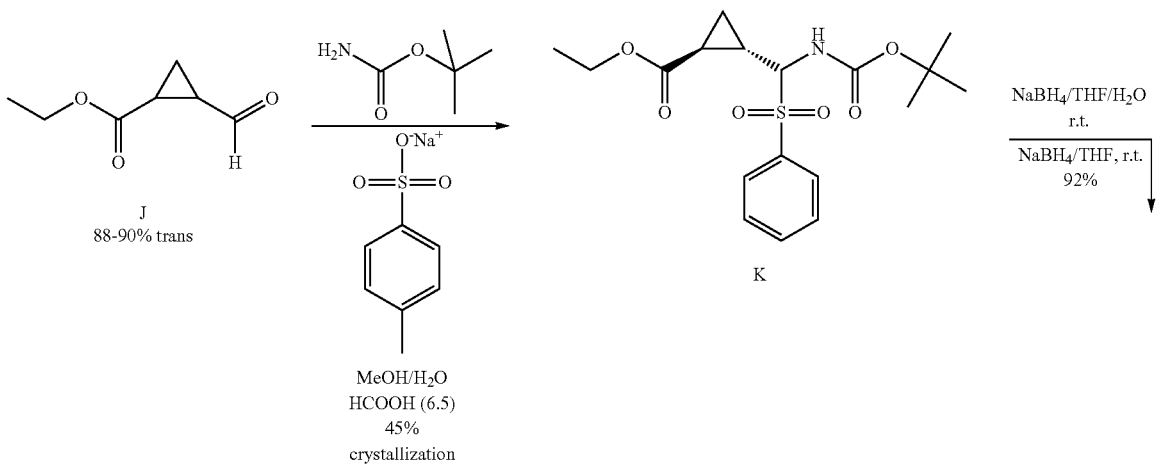

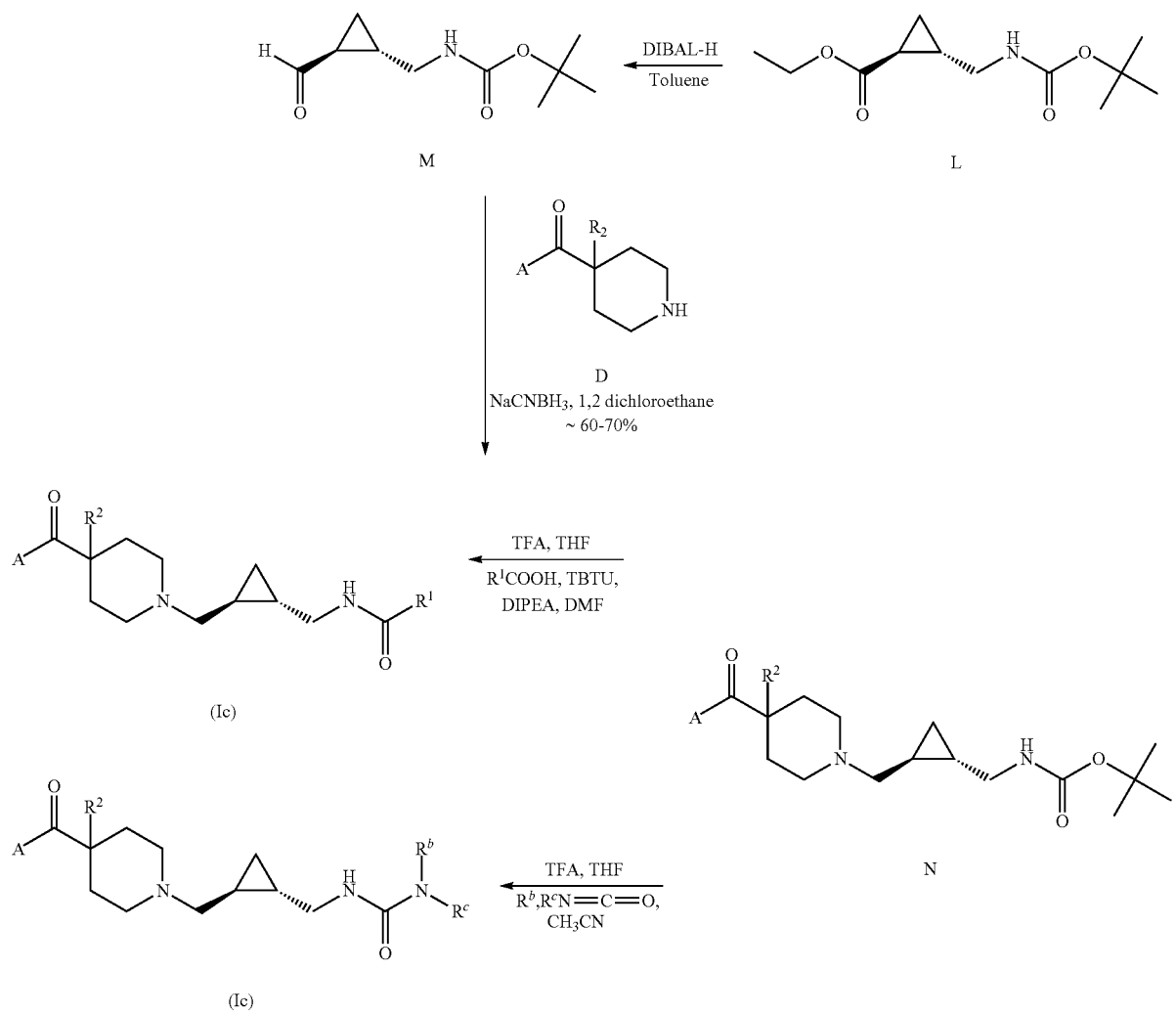

Compounds of the general formula (Ic) wherein $R^1$ is $NR^bR^c$ or different from $NR^bR^c$ can also be prepared according to scheme 4. In this case the intermediate N used on the reductive amination with the phenyl or heteroaryl piperidin-4-yl-methanone is prepared starting from ethyl 2-formyl-1-cyclopropanecarboxylate (88-90% trans isomer) that can react in a reductive BOC amination (known in literature e.g. Tetrahedron Letters 42 (2001), 5093-5094) through the formation of an α-amidoalkyl sulfone K using tert butyl carbamate and anhydrous sodium p-toluensulfinate in solvents like methanol and water. The α-amidoalkyl sulfone K is crystallized in a solvent like n-heptane to obtain only the trans isomer. Reaction of the α-amidoalkyl sulfone intermediate K with sodium borohydride in a solvent like tetrahydrofuran produces the trans-2-(tert-butoxycarbonylamino-methyl)-cyclopropanecarboxylic acid ethyl ester L through the formation of an imine as intermediate. Reduction of the ethyl ester M with a reducing agent such as diisobutylaluminium hydride (DIBAL-H) in an appropriate solvent such as, e.g. toluene at −78° C. gives the aldehyde M which can be used without purification on the next step. Reductive amination of the aldehyde with a substituted phenyl or heteroaryl piperidin-4-yl-methanone D in the presence of a solvent like 1,2-dichloromethane and a reducing agent such as sodium triacetoxy borohydride yields intermediate N. Removal of the Boc protective group under acidic conditions such as trifluoroacetic acid in a suitable solvent such as, e.g. THF yields an intermediate (usually as a salt) that as in scheme 1 can be coupled with carboxylic acids using a coupling agent such as O-benzotriazol-1-yl-N,N,N',N'-tetramethyluronium tetrafluoroborate (TBTU) in a suitable solvent like, e.g. dimethylformamide (DMF) or dioxane in the presence of a base (e.g. triethylamine or diisopropylethylamine) yielding compounds of formula (Ic) wherein $R^1$ is not $NR^bR^c$. In the cases where $R^1$ is $NR^bR^c$ the intermediate mentioned above could react with an isocyanate yielding the corresponding compounds of formula (Ic).

Scheme 5
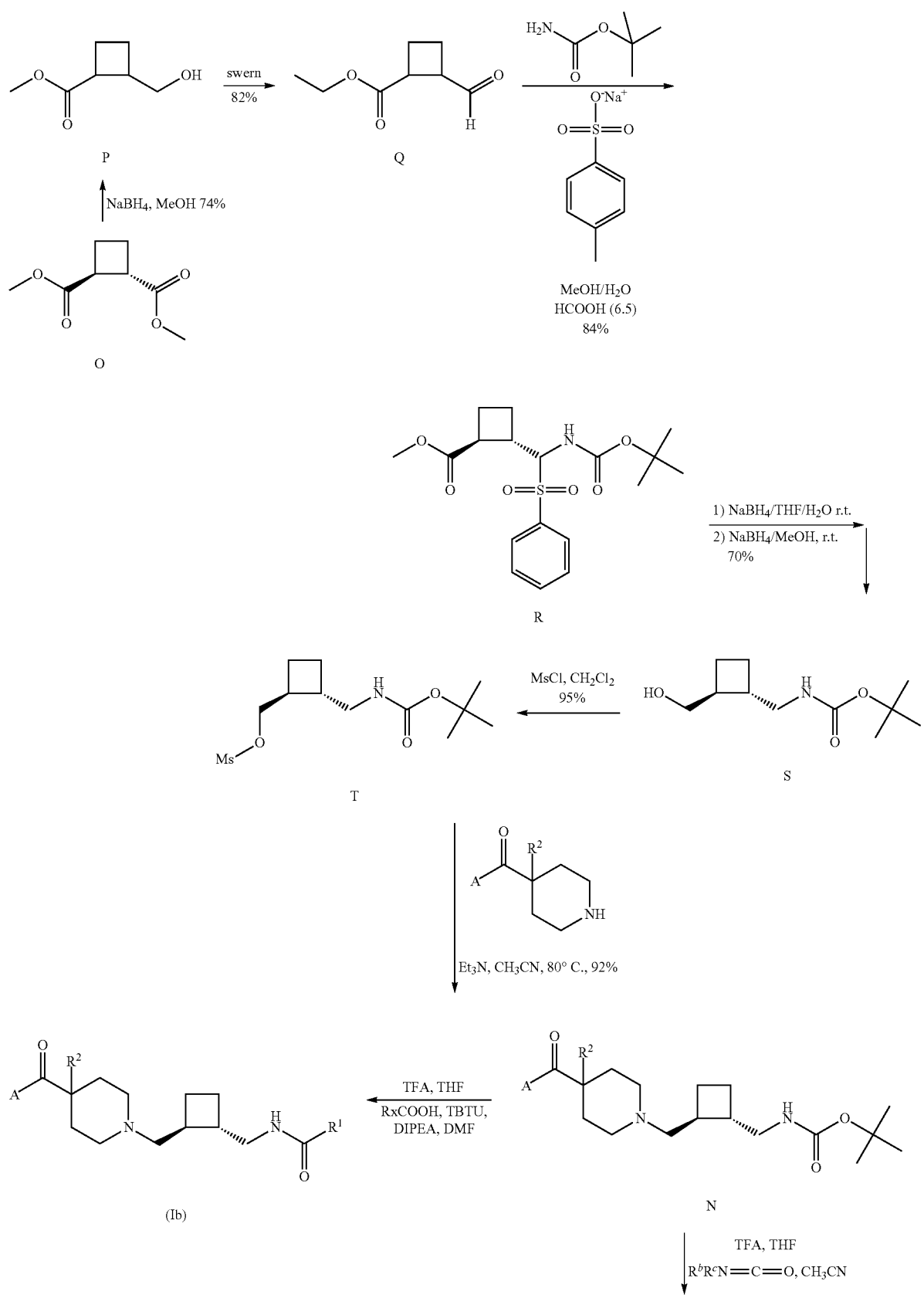

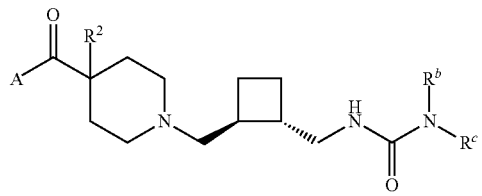

(Ib)

Compounds of the general formula (Ib) wherein $R^1$ is $NR^bR^c$ and (Ib) wherein $R^1$ is not $NR^bR^c$ and wherein can be also prepared according to scheme 5 through an alkylation step with an adequate good leaving group installed on the coupling partner. This coupling partner T (methanesulfonic acid trans-(tert-butoxycarbonylamino-methyl)cyclobutylmethyl ester) can be obtained from the commercial available trans-cyclobutanedicarboxylic acid dimethyl ester O that is reduced to the trans-2-hydroxymethyl-cyclobutanecarboxylic acid methyl ester P with the use of a reducing agent such as sodium borohydride in a solvent like methanol. Oxidation of the alcohol functionality according to methods known to those skilled in the art and described in literature (e.g. under Swern conditions using oxalyl chloride, dimethylsulfoxide and triethylamine in a solvent such as dichloromethane) yields intermediate Q that follows the same step of reductive BOC amination through the formation of an α-amidoalkyl sulfone intermediate already described on scheme 4. Reduction of the ethyl ester S to the alcohol T with a reducing agent such as sodium borohydride and conversion of the alcohol into a good leaving group (e.g. conversion to a mesylate T by reaction with methanosulphonyl chloride in the presence of a base such as N,N-diisopropylethylamine and in a solvent like dichloromethane) that reacts in an alkylation step with a substituted phenyl or heteroaryl piperidin-4-yl-methanone D in presence of a base (e.g N,N-diisopropylethylamine) under refluxing conditions gives intermediates of structure N. The last two steps (removal of the Boc protecting group and amide or urea formation) are the same that the ones already described for schemes 1, 2 and 4.

Scheme 6

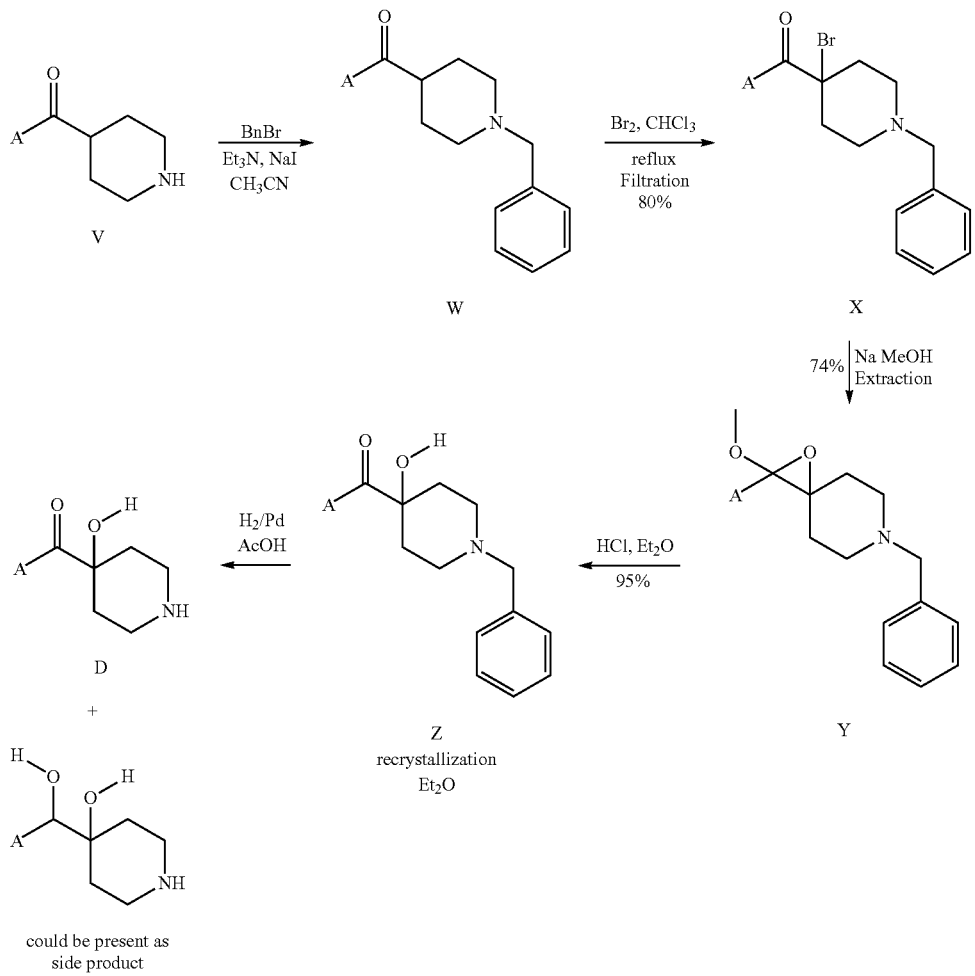

The phenyl or heteroaryl piperidin-4-yl-methanone D intermediates where R² signifies OH can be prepared according to scheme 6 and following a process also partially described in literature (e.g. patent DE 25365103). Introduction of a benzyl group using benzyl bromide in the presence of a base like triethylamine with or without a catalyst such as sodium iodide in a solvent like acetonitrile using a temperature such as 80° C. gave intermediate W. Introduction of bromide in alpha position to the ketone of (1-benzyl-piperidin-4-yl)-(4-fluoro-phenyl)-methanone can be accomplish using bromine under reflux. Treatment of the alpha bromo ketone X with sodium methanolate gave 6-benzyl-2-(4-fluoro-phenyl)-2-methoxy-1-oxa-6-aza-spiro[2.5]octane (Y) that can be hydrolyzed in a solvent like ether under chloridic acid treatment to yield (1-benzyl-4-hydroxy-piperidin-4-yl)-(4-fluoro-phenyl)-methanone (Z). Removal of the benzyl group can be performed under hydrogenation conditions using palladium as catalyst in a solvent like ethyl acetate and methanol to obtain the desired (1-benzyl-4-hydroxy-piperidin-4-yl)-(4-fluoro-phenyl)-methanone (intermediate D). On the last hydrogenation step the reduction of the ketone can also be observed and the diol compound can be formed as a side product.

pared according to scheme 7. The phenyl or heteroaryl piperidin-4-yl-methanone might be protected first with a suitable protective group such as a tert-butoxycarbonyl group which, after introduction of the fluorine atom, can be removed under conditions known to those skilled in the art (e.g. treatment with an acid such as trifluoroacetic acid in a suitable solvent such as dichloromethane). The introduction of fluor can be performed by deprotonation of the corresponding carbon in alpha position to the ketone by treatment with a base in a suitable solvent under anhydrous conditions (e.g. potassium ter-butoxide/t-butanol in DMF) in the presence of a fluorinating agent such as N-fluorobenzenesulphonimide at a temperature from 0° C. to room temperature to obtain after the three steps the aryl-(4-fluoro-piperidin-4-yl)-methanone or heteroaryl-(4-fluoro-piperidin-4-yl)-methanone D.

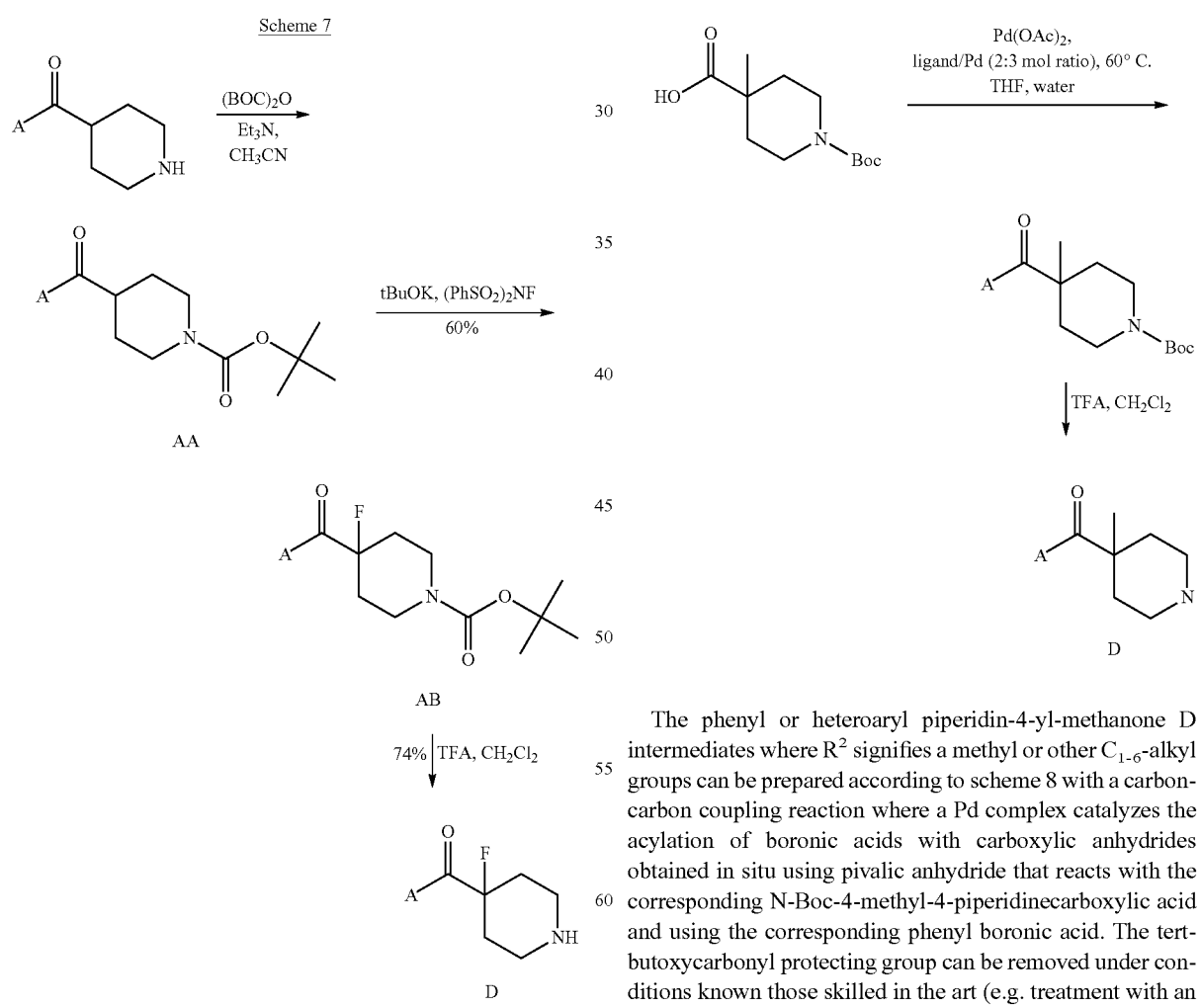

The phenyl or heteroaryl piperidin-4-yl-methanone D intermediates where R² signifies a fluorine atom can be pre- The phenyl or heteroaryl piperidin-4-yl-methanone D intermediates where R² signifies a methyl or other $C_{1-6}$-alkyl groups can be prepared according to scheme 8 with a carbon-carbon coupling reaction where a Pd complex catalyzes the acylation of boronic acids with carboxylic anhydrides obtained in situ using pivalic anhydride that reacts with the corresponding N-Boc-4-methyl-4-piperidinecarboxylic acid and using the corresponding phenyl boronic acid. The tert-butoxycarbonyl protecting group can be removed under conditions known those skilled in the art (e.g. treatment with an acid such as trifluoroacetic acid in a suitable solvent such as dichloromethane) to obtain after the three steps the aryl-(4-methyl-piperidin-4-yl)-methanone D.

Scheme 9

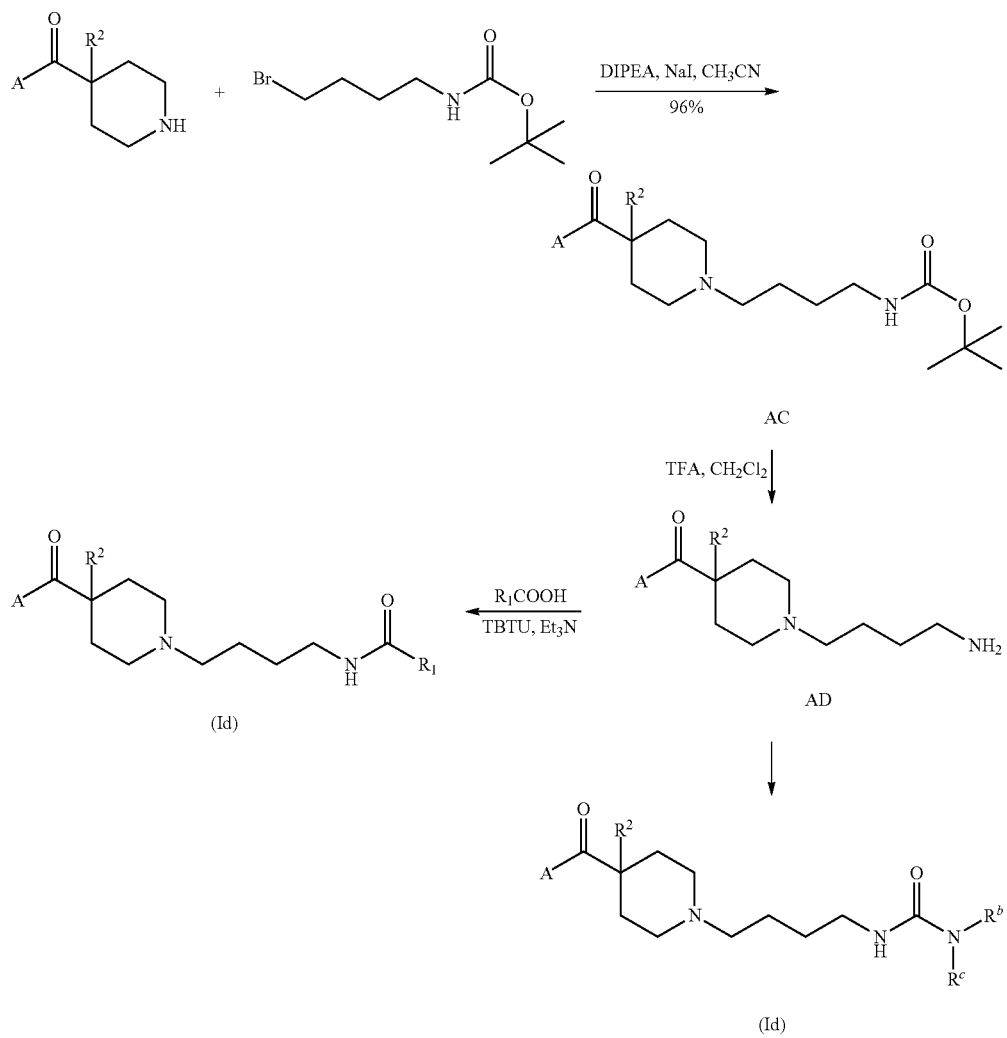

Compounds of the general formula (Id) wherein $R^1$ is $NR^bR^c$ and compounds of formula (Id) wherein $R^1$ is not $NR^bR^c$ can be prepared according to scheme 9 with a compound D phenyl or heteroaryl piperidin-4-yl-methanone that can be alkylated with 4-(Boc-amino)butyl bromide with the use of a base (e.g N,N-diisopropyl ethyl amine) in an appropriate solvent like acetonitrile under refluxing conditions. After removal of the amine protecting group (in our case the Boc group) using acidic conditions (e.g trifluoroacetic acid in a solvent such as dichloromethane) and as already described, the amine intermediate can be coupled with carboxylic acids using a coupling agent such as O-benzotriazol-1-yl-N,N,N', N'-tetramethyluronium tetrafluoroborate (TBTU) in a suitable solvent like, e.g. dimethylformamide (DMF) in presence of a base (e.g. triethylamine or diisopropylethylamine) yielding compounds of formula (Id) wherein $R^1$ is not $NR^bR^c$ or in other cases with an isocyanate yielding the corresponding compounds of formula (Id) wherein $R^1$ is $NR^bR^c$.

Scheme 10

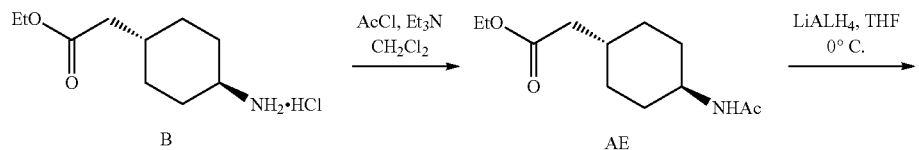

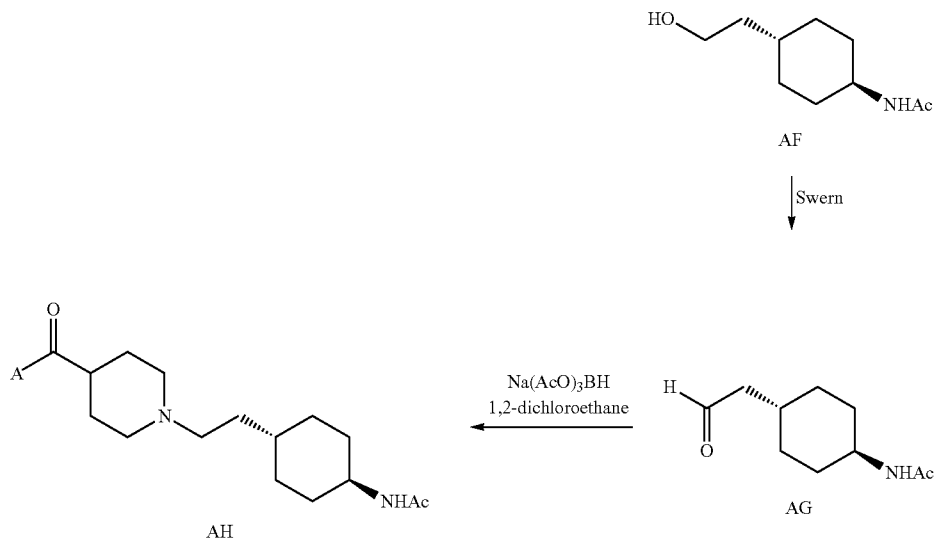

Acetic acid amide derivatives of structure AH can be conveniently prepared according to scheme 10 starting from compound B. The reaction sequence involves in a first step the treatment of compound B with AcCl in presence of a base such as Et$_3$N in a solvent such as CH$_2$Cl$_2$ to obtain a compound of formula AE. Reduction with a reagent such as LiAlH$_4$ in a solvent such as CH$_2$Cl$_2$ at 0° C. provides a compound of formula AF. Among several oxidation conditions known in the literature, the Swern oxidation (A. Mancuso, D. Swern, *Synthesis* 1981, 165-185) of alcohol AF provides intermediate AG. Reaction of aldehyde AG with an appropriate substituted piperidine in the presence of a reducing agent such as Na(AcO)$_3$BH in a solvent such as 1,2-dichloroethane provides compounds of formula AH.

Compounds of formula Ia where A is a substituted or unsubstituted thiophenyl group can be prepared as described in Scheme 1 using a piperidin-4-yl-thiophen-2-yl-methanone of formula AL as intermediate D. The preparation of intermediates of formula AL is depicted in Scheme 11. A thiophene of formula AI can be deprotonated with a base such as n-BuLi in a solvent such as THF and reacted with 4-formyl-piperidine-1-carboxylic acid tert-butyl ester to obtain an alcohol of formula AJ. Oxidation of an alcohol of formula AJ with reagents such as for example TPAP/NMO or MnO$_2$ in a solvent such as CH$_2$Cl$_2$ affords a ketone of formula AK. Treatment of a compound of formula AK with an acid such as HCl affords a compound of formula AL.

Scheme 11

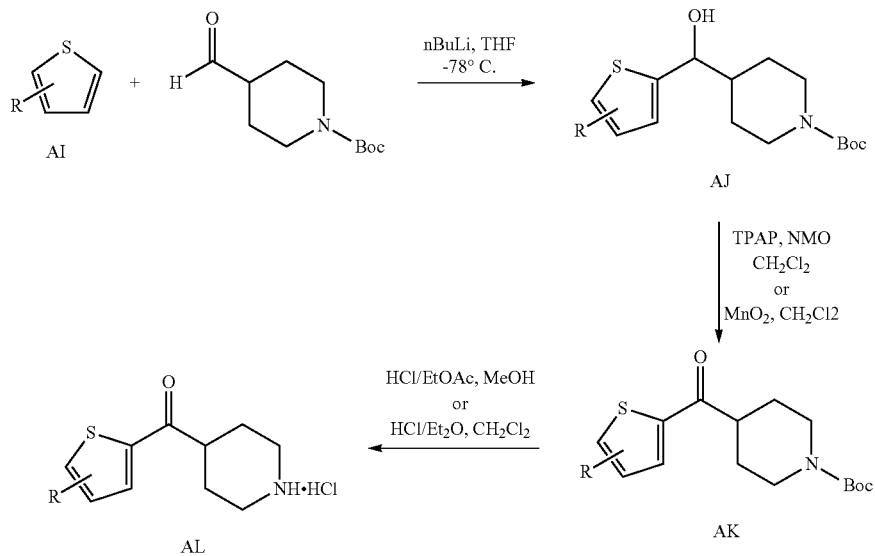

Scheme 12

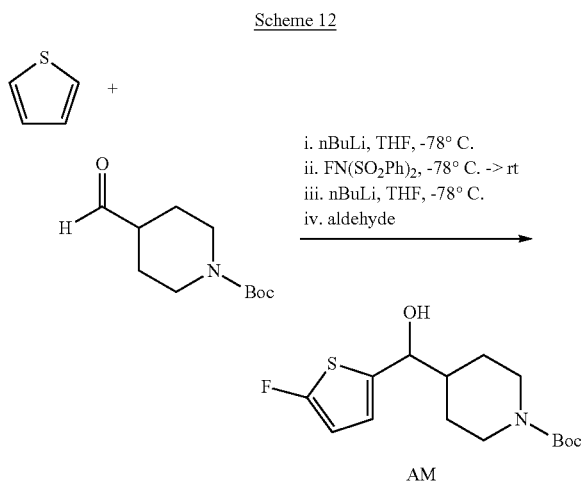

A compound of structure AL (Scheme 11) where R equals 5-fluoro can be prepared according to scheme 12. This method consists in the subsequent double deprotonation of thiophene with a base such as n-BuLi in a solvent such as THF and reaction with a fluorinating agent such as N-fluorodibenzenesulfonimide after the first deprotonation step and 4-formyl-piperidine-1-carboxylic acid tert-butyl ester after the second, to obtain an alcohol of formula AM.

The ability of the compounds to bind to the 5-HT$_{2A}$, D$_3$ and D$_2$ receptors was determined using radioligand binding to cloned receptors selectively expressed in HEK-293 EBNA cells.

Membrane Preparation for Human D$_2$, Human D$_3$ and Human 5-HT$_{2A}$ Receptors HEK-293 EBNA cells were transiently transfected with expression plasmids encoding for the human D$_2$ or D$_3$ dopamine- or for the human 5-HT$_{2A}$ serotonin receptor, respectively. The cells were harvested 48 h post-transfection, washed three times with cold PBS and stored at −80° C. prior to use. The pellet was suspended in cold 50 mM Tris-HCl buffer containing 10 mM EDTA (pH 7.4) and homogenized with a Polytron (Kinematica AG, Basel, Switzerland) for 20-30 sec at 12.000 rpm. After centrifugation at 48.000×g for 30 min at 4° C., the pellet was resuspended in cold 10 mM Tris-HCl buffer containing 0.1 mM EDTA (pH 7.4), homogenized, and centrifuged as above. This pellet was further resuspended in a smaller volume of ice cold 10 mM Tris-HCl buffer containing 0.1 mM EDTA (pH 7.4) and homogenized with a Polytron for 20-30 sec at 12.000 rpm. The protein content of this homogenate was determined with the Bio-Rad (Bradford) Protein Assay (Biorad Laboratories GmbH, München, Germany) according to the instructions of the manufacturer using gamma globulin as the standard. This homogenate was stored at −80° C. in aliquots and thawed immediately prior to use.

Radioligand Binding Assay Conditions

Aliquots of membrane preparations were thawed at RT, resupended in assay buffer (D$_2$) D$_3$: 50 mM Tris-HCl, 120 mM NaCl, 5 mM MgCl$_2$, 1 mM EDTA, 5 mM KCl, 1.5 mM CaCl$_2$, pH=7.4; 5-HT$_{2A}$: 50 mM Tris-HCl, 10 mM MgCl$_2$, 1 mM EGTA, pH=7.4), homogenized with a Polytron for 20-30 sec at 12.000 rpm and adjusted to a final concentration of approximately 7.5 μg protein/well (D$_2$, D$_3$) and 15 μg protein/well (5-HT$_{2A}$), respectively.

The binding affinity (Ki) of the compounds was determined using radioligand binding. Membranes were incubated in a total volume of 200 μl with a fixed concentration of radioligand (final concentration approximately 0.7 nM [$^3$H]-spiperone for D$_2$, 0.5 nM [$^3$H]-spiperone for D$_3$, and 1.1 nM [$^3$H]-ketanserin for 5-HT$_{2A}$) and ten concentrations of test compound in ranging between 10 μM-0.1 nM for 1 h at RT. At the end of the incubation, the reaction mixtures were filtered on to unifilter 96-well white microplates with bonded GF/C filters (Packard BioScience, Zürich, Switzerland; preincubated for 1 h in 0.1% polyethylenimine (PEI) in assay buffer) with a Filtermate 196 harvester (Packard BioScience) and washed 3 times with cold assay buffer. The nonspecific binding was determined with equally composed reaction mixtures in the presence of 10 μM unlabelled spiperone. Per well 45 μl of Microscint 40 (Perkin Elmer, Schwerzenbach, Switzerland) was added, plates for sealed, shaken for 20 min and counted for 3 min on a Topcount Microplate Scintillation Counter (Canberra Packard SA, Zürich, Switzerland) with quenching correction.

Data Calculation

The CPM value for each duplicate of a concentration of competing compound was averaged (y1), then the % specific binding was calculated according to the equation (((y1-nonspecific)/(total binding-non-specific))×100). Graphs were plotted with the % specific binding using XLfit, a curve fitting program that iteratively plots the data using Levenburg Marquardt algorithm. The single site competition analysis equation used was y=A+((B−A)/(1+((x/C)$^D$))), where y is the % specific binding, A is the minimum y, B is the maximum y, C is the IC$_{50}$, x is the log$_{10}$ of the concentration of the competing compound and D is the slope of the curve (the Hill Coefficient). From these curves the IC$_{50}$ (inhibition concentration at which 50% specific binding of the radioligand was displaced) and Hill coefficient were determined. The affinity constant (Ki) was calculated using the Cheng-Prusoff equation Ki=(IC$_{50}$/1+([L]/Kd), where [L] is the concentration of radioligand and Kd is the dissociation constant of the radioligand at the receptor as determined by the saturation isotherm.

The compounds of the present invention are selective dual modulators of the serotonin 5-HT$_{2A}$ and dopamine D$_3$ receptors as this is shown with the activity table hereinafter which gives the Ki values in nM for the serotonin 5-HT$_{2a}$, dopamine D$_3$ and dopamine D$_2$ receptors for some examples of the compounds of the present invention:

| Activity table | | | | |
|---|---|---|---|---|
| Example | 9 | 20 | 22 | 23 |
| Ki(nM) D$_3$/5HT$_{2A}$/D$_2$ | 6/2/106 | 18/5/586 | 15/4/149 | 72/5/73 |
| Example | 29 | 33 | 25 | 41 |
| Ki(nM) D$_3$/5HT$_{2A}$/D$_2$ | 32/8/450 | 110/65/1977 | 13/269/777 | 4/11/677 |
| Example | 46 | 50 | 57 | 58 |
| Ki(nM) D$_3$/5HT$_{2A}$/D$_2$ | 15/2/30 | 29/2/288 | 53/21/1334 | 19/80/3542 |
| Example | 61 | 64 | 70 | 72 |
| Ki(nM) D$_3$/5HT$_{2A}$/D$_2$ | 35/64/2895 | 4/26/3998 | 97/22/2714 | 39/26/2133 |
| Example | 14 | 26 | 29 | 30A25 |
| Ki(nM) D$_3$/5HT$_{2A}$/D$_2$ | 144/12/96 | 17/14/684 | 37/8/450 | 26/5/1285 |

-continued

Activity table

| Example | 30A27 | 30A28 | 30A29 | 30A36 |
|---|---|---|---|---|
| Ki(nM) $D_3$/$5HT_{2A}$/$D_2$ | 8/8/1117 | 9/5/470 | 207/25/1008 | 26/5/1285 |

| Example | 30A37 | 30A58 | 30A59 | 30A64 |
|---|---|---|---|---|
| Ki(nM) $D_3$/$5HT_{2A}$/$D_2$ | 29/11/2002 | 30/15/2070 | 19/5/888 | 19/13/625 |

| Example | 34 | 39 | 40 | 42 |
|---|---|---|---|---|
| Ki(nM) $D_3$/$5HT_{2A}$/$D_2$ | 23/6/192 | 2/3/1844 | 8/9/502 | 146/11/352 |

| Example | 42A7 | 63A14 | 65A11 |
|---|---|---|---|
| Ki(nM) $D_3$/$5HT_{2A}$/$D_2$ | 86/26/176 | 44/83/8539 | 71/38/1447 |

The present invention also provides pharmaceutical compositions containing compounds of the invention, for example compounds of formula I and their pharmaceutically suitable acid addition salts, and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acid or its salts and the like can be used, for example, as such as carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts and, if desired, one or more other therapeutically valuable substances into a galenical administration form together with one or more therapeutically inert carriers.

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The following examples are provided to further elucidate the invention. They should not be considered as limiting the scope of the invention, but merely as being representative thereof. Unless otherwise indicated, the following examples have been performed, regardless of the tense in which they are written.

EXPERIMENTAL PROCEDURES

Example 1

4-Chloro-N-trans-(4-{2-[4-(4-fluoro-benzoyl)-piperidin-1-yl]-ethyl}-cyclohexyl)-benzamide Intermediate B Trans-(4-Amino-cyclohexyl)-acetic acid ethyl ester Step 1

(4-Nitro-phenyl)-acetic acid (50 g, 276 mmol) was added to a stirred solution of 22.08 g of 50% sodium hydroxide solution in 450 mL deionizated water. The clear yellow solution is transferred into a high-pressure autoclave that it charged with 30 g (511 mmol) of water-wet sponge nickel catalyst. The autoclave is sealed, flushed with nitrogen and then pressurized to 115 bar with hydrogen. The reaction mixture is stirred and heated to 125° C. for 48 h. At that time the autoclave is cooled, vented and charged under nitrogen with another 30 g (511 mmol) of the sponge nickel catalyst. The autoclave is flushed again with nitrogen and then pressurized to 115 bar and the vessel is heated to 130° C. while stirring (a maximum pressure of 130 bars is observed). Hydrogenation is continued for 5 days to 130° C. The autoclave is then cooled, vented and flushed with nitrogen and the contents are removed and filtered through filter aid to remove catalyst. After removal of the solvent 74 g of crude material was obtained. The intermediated is used directly in the next step without purification. MS (m/e): 158.3 (M+H$^+$)

Step 2

A solution of the Trans-(4-amino-cyclohexyl)-acetic acid obtained (74 g, 476 mmol) was adjusted to pH 5 with 25% HCl. The mixture was evaporated to dryness and dried under vacuum overnight. The residue was suspended in 146 mL of a 6.5N ethanolic HCl solution and 0.6 L of ethanol was added to the mixture. After 4 h refluxing, the mixture was cooled and filtered and the filtrate was concentrated to dryness under vacuum. The residue was dissolved in ethanol, treated with ether and cooled overnight in the refrigerator. to give the Trans-(4-Amino-cyclohexyl)-acetic acid ethyl ester hydrochloride (19.7 g, 32% on the two steps) as a white solid which was filtered and dried under vacuum. MS (m/e): 186.1 (M+H$^+$)

Intermediate C

Step 1

Trans-(4-tert-Butoxycarbonylamino-cyclohexyl)-acetic acid ethyl ester

To a solution of Trans-(4-Amino-cyclohexyl)-acetic acid ethyl ester (1.28 g, 7 mmol), in dichloromethane (15 mL), di-tert-butyl-dicarbonate (2.26 g, 10 mmol), triethylamine (0.699 mL, 7 mmol) and 4-dimethylaminopyridine (0.042 mL, 0.35 mmol) were added. The mixture was stirred for 8 h until TLC indicated completion of the reaction. Water was added and the solution was extracted three times with dichloromethane. The combined organic layers were washed with water and brine, dried over magnesium sulfate, filtered and evaporated. The crude product was purified by flash-chromatography on silica gel with hexane:ethyl acetate (4:2 to 3:2) to give 1.2 g (60%) of the product as a white solid. MS (m/e): 284.4 (M–H$^+$).

Step 2

Trans-[4-(2-Oxo-ethyl)-cyclohexyl]-carbamic acid tert-butyl ester

To a solution of trans-(4-tert-Butoxycarbonylamino-cyclohexyl)-acetic acid ethyl ester (1.04 g, 4 mmol), in toluene (10 mL) at −78° C. a 1.2M solution of DIBAL-H (5.1 mL, 6 mmol) in toluene was added. The mixture was stirred at −78° C. until TLC after 0.5 h indicated completion of the reaction. Water was added and the solution was extracted three times with dichloromethane. The combined organic layers were washed with water and brine, dried over magnesium sulfate, filtered and evaporated. The crude product was used without purification on the next step. MS (m/e): 242.3 (M+H$^+$).

Intermediate E

Trans-(4-{2-[4-(4 Fluoro-benzoyl)-piperidin-1-yl]-ethyl}-cyclohexyl)-carbamic acid tert-butyl ester A mixture of 4-(4-fluorobenzoyl)piperidine (0.850 g, 3.4 mmol), Trans-[4-(2-Oxo-ethyl)-cyclohexyl]-carbamic acid tert-butyl ester (0.926 g, 4 mmol), in 1, 2 dichloroethane (10 mL) was stirred for 4 h at room temperature and sodium triacetoxyborohydride (1.33 g, 6 mmol) was added and the resulting solution was stirred for 12 hours until the TLC indicated completion of the reaction. The mixture was filtrated and concentrated to dryness and purified with column chromatography on silica gel using $CH_2Cl_2$-$CH_2Cl_2$/MeOH (1-9:1). The product fractions were concentrated to give 1.4 g (3.25 mmol, 93.2% yield) of a light yellow solid. MS (m/e): 433.4 (M+H$^+$).

Intermediate F

Trans-{1-[2-(4-Amino-cyclohexyl)-ethyl]-piperidin-4-yl}-(4-fluoro-phenyl)-methanone (Could be Obtained as the Trifluoroacetic Acid Salt)

1.4 g (3.25 mmol) of (4-{2-[4-(4-Fluoro-benzoyl)-piperidin-1-yl]-ethyl}-cyclohexyl)-carbamic acid tert-butyl ester is solved in dichloromethane (30 mL) and trifluoroacetic acid is added at 0° C. (1.98 mL, 26 mmol) and the mixture is stirred at room temperature overnight. $NaHCO_3$ is slowly added until pH 9 and the mixture extracted with 3 times with dichloromethane and ethyl acetate. The solvent was evaporated to yield 0.812 g (24.4 mmol, 75.5%) of a white solid that was used without purification on the next steps. MS (m/e): 333.2 (M+H$^+$).

4-Chloro-N-trans-(4-{2-[4-(4-fluoro-benzoyl)-piperidin-1-yl]-ethyl}-cyclohexyl)-benzamide 4-chloro benzoic acid (0.014 g, 0.09 mmol), 2-(1H-benzotriazol-1-yl)-1,1,3,3-tetramethyl uronium tetrafluoroborate (0.029 g, 0.09 mmol) and (0.06 mL, 0.270 mmol) of N-ethyldiisopropylamine were stirred in 0.3 mL of DMF for 0.5 h at room temperature and Trans-{1-[2-(4-Amino-cyclohexyl)-ethyl]-piperidin-4-yl}-(4-fluoro-phenyl)-methanone (trifluoro acetic acid salt) (0.030 g, 0.09 mmol) was added. The mixture was stirred for 12 hours at room temperature. The mixture was concentrated to dryness and the residue was taken up on methanol and purified with preparative HPLC on reversed phase eluting with acetonitrile/water. The combined produced fractions were evaporated under reduced pressure to yield 0.015 g of a off-white solid (0.032 mmol, 36%). MS (m/e): 471.3 (M+H$^+$).

According to the procedure described for the synthesis of example 1 further derivatives have been synthesized from the respective Trans-{1-[2-(4-Amino-cyclohexyl)-ethyl]-piperidin-4-yl}-(4-fluoro-phenyl)-methanone and the corresponding acid. They comprise examples 1 to 30A63.

| Ex. No | Systematic name | MW | Starting materials | MW found (M + H)$^+$ |
|---|---|---|---|---|
| 1 | 4-Chloro-N-trans (4-{2-[4-(4-fluoro-benzoyl)-piperidin-1-yl]-ethyl}-cyclohexyl)-benzamide | 471.0 | Trans-{1-[2-(4-Amino-cyclohexyl)-ethyl]-piperidin-4-yl}-(4-fluoro-phenyl)-methanone (trifluoro acetic acid salt) and 4-chloro benzoic acid | 471.3 |
| 2 | Cyclopropanecarboxylic acid trans (4-{2-[4-(4-fluoro-benzoyl)-piperidin-1-yl]-ethyl}-cyclohexyl)-amide | 400.5 | Trans-{1-[2-(4-Amino-cyclohexyl)-ethyl]-piperidin-4-yl}-(4-fluoro-phenyl)-methanone (trifluoro acetic acid salt) and Cyclopropanecarboxylic acid | 401.3 |
| 3 | 4-(3,5-Dimethyl-isoxazol-4-ylmethoxy)-N-trans (4-{2-[4-(4-fluoro-benzoyl)-piperidin-1-yl]-ethyl}-cyclohexyl)-benzamide | 561.7 | Trans-{1-[2-(4-Amino-cyclohexyl)-ethyl]-piperidin-4-yl}-(4-fluoro-phenyl)-methanone (trifluoro acetic acid salt) and 4-(3,5-Dimethyl-isoxazol-4-ylmethoxy)-benzoic acid | 562.3 |
| 4 | Tetrahydro-pyran-4-carboxylic acid trans-(4-{2-[4-(4-fluoro-benzoyl)-piperidin-1-yl]-ethyl}-cyclohexyl)-amide | 444.59 | Trans-{1-[2-(4-Amino-cyclohexyl)-ethyl]-piperidin-4-yl}-(4-fluoro-phenyl)-methanone (trifluoro acetic acid salt) and Tetrahydro-pyran-4-carboxylic acid | 445.3 |

-continued

| Ex. No | Systematic name | MW | Starting materials | MW found (M + H)+ |
|---|---|---|---|---|
| 5 | N-trans-(4-{2-[4-(4-Fluoro-benzoyl)-piperidin-1-yl]-ethyl}-cyclohexyl)-4-trifluoromethyl-benzamide | 504.57 | Trans-{1-[2-(4-Amino-cyclohexyl)-ethyl]-piperidin-4-yl}-(4-fluoro-phenyl)-methanone (trifluoro acetic acid salt) and 4-(trifluoromethyl) benzoic acid | 505.2 |
| 6 | N-trans (4-{2-[4-(4-Fluoro-benzoyl)-piperidin-1-yl]-ethyl}-cyclohexyl)-3-methoxy-propionamide | 418.55 | Trans-{1-[2-(4-Amino-cyclohexyl)-ethyl]-piperidin-4-yl}-(4-fluoro-phenyl)-methanone (trifluoro acetic acid salt) and 3-methoxy-propionic acid | 419.3 |
| 7 | N-trans (4-{2-[4-(4-Fluoro-benzoyl)-piperidin-1-yl]-ethyl}-cyclohexyl)-4-morpholin-4-yl-benzamide | 521.68 | Trans-{1-[2-(4-Amino-cyclohexyl)-ethyl]-piperidin-4-yl}-(4-fluoro-phenyl)-methanone (trifluoro acetic acid salt) and 4-morpholino benzoic acid | 522.5 |
| 8 | N-trans (4-{2-[4-(4-Fluoro-benzoyl)-piperidin-1-yl]-ethyl}-cyclohexyl)-3-(5-methyl-[1,2,4]oxadiazol-3-yl)-benzamide | 518.3 | Trans-{1-[2-(4-Amino-cyclohexyl)-ethyl]-piperidin-4-yl}-(4-fluoro-phenyl)-methanone (trifluoro acetic acid salt) and 3-(5-methyl-1,2,4-oxadiazol-3-yl)-benzoic acid | 519.4 |
| 9 | N-trans (4-{2-[4-(4-Fluoro-benzoyl)-piperidin-1-yl]-ethyl}-cyclohexyl)-4-pyrrol-1-yl-benzamide | 501.65 | Trans-{1-[2-(4-Amino-cyclohexyl)-ethyl]-piperidin-4-yl}-(4-fluoro-phenyl)-methanone (trifluoro acetic acid salt) and 4-(1H-pyrrol-1yl) benzoic acid | 502.1 |
| 10 | 4-Ethoxy-N-trans (4-{2-[4-(4-fluoro-benzoyl)-piperidin-1-yl]-ethyl}-cyclohexyl)-benzamide | 480.62 | Trans-{1-[2-(4-Amino-cyclohexyl)-ethyl]-piperidin-4-yl}-(4-fluoro-phenyl)-methanone (trifluoro acetic acid salt) and 4-Ethoxybenzoic acid | 481.4 |
| 11 | Tetrahydro-furan-3-carboxylic acid trans (4-{2-[4-(4-fluoro-benzoyl)-piperidin-1-yl]-ethyl}-cyclohexyl)-amide | 430.56 | Trans-{1-[2-(4-Amino-cyclohexyl)-ethyl]-piperidin-4-yl}-(4-fluoro-phenyl)-methanone (trifluoro acetic acid salt) and Tetrahydro-furan-3-carboxylic acid | 431.4 |
| 12 | 4-Acetylamino-N-trans (4-{2-[4-(4-fluoro-benzoyl)-piperidin-1-yl]-ethyl}-cyclohexyl)-benzamide | 493.2 | Trans-{1-[2-(4-Amino-cyclohexyl)-ethyl]-piperidin-4-yl}-(4-fluoro-phenyl)-methanone (trifluoro acetic acid salt) and 4-Acetylamino benzoic acid | 494.1 |
| 13 | 2-Methyl-2H-indazole-3-carboxylic acid trans (4-{2-[4-(4-fluoro-benzoyl)-piperidin-1-yl]-ethyl}-cyclohexyl)-amide | 490.62 | Trans-{1-[2-(4-Amino-cyclohexyl)-ethyl]-piperidin-4-yl}-(4-fluoro-phenyl)-methanone (trifluoro acetic acid salt) and 2-Methyl-2H-indazole-3-carboxylic acid | 491.4 |
| 14 | 2-(4-Chloro-phenyl)-N-trans (4-{2-[4-(4-fluoro-benzoyl)-piperidin-1-yl]-ethyl}-cyclohexyl)-isobutyramide | 513.1 | Trans-{1-[2-(4-Amino-cyclohexyl)-ethyl]-piperidin-4-yl}-(4-fluoro-phenyl)-methanone (trifluoro acetic acid salt) and 4-chloro-alpha, alpha-dimethylphenyl acetic acid | 514.5 |
| 15 | N-trans-(4-{2-[4-(4-Fluoro-benzoyl)-piperidin-1-yl]-ethyl}-cyclohexyl)-4-(3-methyl-5-oxo-4,5-dihydro-pyrazol-1-yl)-benzamide | 532.6 | Trans-{1-[2-(4-Amino-cyclohexyl)-ethyl]-piperidin-4-yl}-(4-fluoro-phenyl)-methanone (trifluoro acetic acid salt) and 4-4-(3-methyl-5-oxo-4,5-dihydro-pyrazol-1-yl)-benzoic acid | 533.2 |
| 16 | 6-Chloro-2-methyl-quinoline-3-carboxylic acid trans-(4-{2-[4-(4-fluoro-benzoyl)-piperidin-1-yl]-ethyl}-cyclohexyl)-amide | 536.09 | Trans-{1-[2-(4-Amino-cyclohexyl)-ethyl]-piperidin-4-yl}-(4-fluoro-phenyl)-methanone (trifluoro acetic acid salt) and 6-Chloro-2-methyl-quinoline-3-carboxylic acid | 536.2 |
| 17 | 5-Chloro-1-(3,4-dichloro-benzyl)-6-oxo-1,6-dihydro-pyridine-3-carboxylic | 647.02 | Trans-{1-[2-(4-Amino-cyclohexyl)-ethyl]-piperidin-4-yl}-(4-fluoro-phenyl)-methanone (trifluoro acetic acid salt) and | 648.1 |

| Ex. No | Systematic name | MW | Starting materials | MW found (M + H)+ |
|---|---|---|---|---|
| | acid trans-(4-{2-[4-(4-fluoro-benzoyl)-piperidin-1-yl]-ethyl}-cyclohexyl)-amide | | 5-Chloro-1-(3,4-dichloro-benzyl)-6-oxo-1,6-dihydro-pyridine-3-carboxylic acid | |
| 18 | N-trans (4-{2-[4-(4-Fluoro-benzoyl)-piperidin-1-yl]-ethyl}-cyclohexyl)-6-methyl-nicotinamide | 451.59 | Trans-{1-[2-(4-Amino-cyclohexyl)-ethyl]-piperidin-4-yl}-(4-fluoro-phenyl)-methanone (trifluoro acetic acid salt) and 6-methylnicotinic acid | 452.7 |
| 19 | 4-Cyano-N-trans (4-{2-[4-(4-fluoro-benzoyl)-piperidin-1-yl]-ethyl}-cyclohexyl)-benzamide | 461.58 | Trans-{1-[2-(4-Amino-cyclohexyl)-ethyl]-piperidin-4-yl}-(4-fluoro-phenyl)-methanone (trifluoro acetic acid salt) and 4-Cyanobenzoic acid | 462.2 |
| 20 | [1,8]Naphthyridine-4-carboxylic acid trans-(4-{2-[4-(4-fluoro-benzoyl)-piperidin-1-yl]-ethyl}-cyclohexyl)-amide | 488.61 | Trans-{1-[2-(4-Amino-cyclohexyl)-ethyl]-piperidin-4-yl}-(4-fluoro-phenyl)-methanone (trifluoro acetic acid salt) and [1,8]Naphthyridine-4-carboxylic acid trans | 489.2 |
| 21 | N-trans (4-{2-[4-(4-Fluoro-benzoyl)-piperidin-1-yl]-ethyl}-cyclohexyl)-4-pyrazol-1-yl-benzamide | 502.6 | Trans-{1-[2-(4-Amino-cyclohexyl)-ethyl]-piperidin-4-yl}-(4-fluoro-phenyl)-methanone (trifluoro acetic acid salt) and 4-(1H-pyrazol-1-yl-benzoic acid | 503.1 |
| 22 | 2,4-Dichloro-N-trans (4-{2-[4-(4-fluoro-benzoyl)-piperidin-1-yl]-ethyl}-cyclohexyl)-benzamide | 505.46 | Trans-{1-[2-(4-Amino-cyclohexyl)-ethyl]-piperidin-4-yl}-(4-fluoro-phenyl)-methanone (trifluoro acetic acid salt) and 2,4-Dichlorobenzoic acid | 507.1 |
| 23 | 4-(4-Chloro-benzenesulfonyl)-N-trans (4-{2-[4-(4-fluoro-benzoyl)-piperidin-1-yl]-ethyl}-cyclohexyl)-benzamide | 611.18 | Trans-{1-[2-(4-Amino-cyclohexyl)-ethyl]-piperidin-4-yl}-(4-fluoro-phenyl)-methanone (trifluoro acetic acid salt) and 4-(4-4-(4-Chloro-benzenesulfonyl)-benzoic acid | 611.8 |
| 24 | N-trans (4-{2-[4-(4-Fluoro-benzoyl)-piperidin-1-yl]-ethyl}-cyclohexyl)-4-trifluoromethoxy-benzamide | 520.5 | Trans-{1-[2-(4-Amino-cyclohexyl)-ethyl]-piperidin-4-yl}-(4-fluoro-phenyl)-methanone (trifluoro acetic acid salt) and 4-trifluoromethoxy-benzoic acid | 521.3 |
| 25 | 3-Ethoxy-N-trans (4-{2-[4-(4-fluoro-benzoyl)-piperidin-1-yl]-ethyl}-cyclohexyl)-propionamide | 432.5 | Trans-{1-[2-(4-Amino-cyclohexyl)-ethyl]-piperidin-4-yl}-(4-fluoro-phenyl)-methanone (trifluoro acetic acid salt) and 3-Ethoxy-propionic acid | 433.3 |
| 26 | 3,3,3-Trifluoro-N-trans-(4-{2-[4-(4-fluoro-benzoyl)-piperidin-1-yl]-ethyl}-cyclohexyl)-propionamide | 442.5 | Trans-{1-[2-(4-Amino-cyclohexyl)-ethyl]-piperidin-4-yl}-(4-fluoro-phenyl)-methanone (trifluoro acetic acid salt) and 3,3,3-Trifluoro-propionic acid | 443.1 |
| 27 | N-trans-(4-{2-[4-(4-Fluoro-benzoyl)-piperidin-1-yl]-ethyl}-cyclohexyl)-4-(1,1,2,2-tetrafluoro-ethoxy)-benzamide | 552.5 | Trans-{1-[2-(4-Amino-cyclohexyl)-ethyl]-piperidin-4-yl}-(4-fluoro-phenyl)-methanone (trifluoro acetic acid salt) and 4-(1,1,2,2-tetrafluoro-ethoxy)-benzoic acid | 553.2 |
| 28 | N-trans-(4-{2-[4-(4-Fluoro-benzoyl)-piperidin-1-yl]-ethyl}-cyclohexyl)-propionamide | 388.5 | Trans-{1-[2-(4-Amino-cyclohexyl)-ethyl]-piperidin-4-yl}-(4-fluoro-phenyl)-methanone (trifluoro acetic acid salt) and propionic acid | 389.3 |
| 29 | Cyclohexanecarboxylic acid trans-(4-{2-[4-(4-fluoro-benzoyl)-piperidin-1-yl]-ethyl}-cyclohexyl)-amide | 442.6 | Trans-{1-[2-(4-Amino-cyclohexyl)-ethyl]-piperidin-4-yl}-(4-fluoro-phenyl)-methanone (trifluoro acetic acid salt) and cyclohexanecarboxylic acid | 443.5 |
| 30 | Adamantane-1-carboxylic acid trans-(4-{2-[4-(4-fluoro-benzoyl)-piperidin-1-yl]-ethyl}-cyclohexyl)-amide | 494.7 | Trans-{1-[2-(4-Amino-cyclohexyl)-ethyl]-piperidin-4-yl}-(4-fluoro-phenyl)-methanone (trifluoro acetic acid salt) and Adamantane-1-carboxylic acid | 495.4 |

-continued

| Ex. No | Systematic name | MW | Starting materials | MW found $(M + H)^+$ |
|---|---|---|---|---|
| 30A1 | 2,2,2-Trifluoro-N-trans (4-{2-[4-(4-fluoro-benzoyl)-piperidin-1-yl]-ethyl}-cyclohexyl)-acetamide | 450.9 | Trans-{1-[2-(4-Amino-cyclohexyl)-ethyl]-piperidin-4-yl}-(4-fluoro-phenyl)-methanone (trifluoro acetic acid salt) and trifluoroacetic acid | 453.0 |
| 30A2 | 5-Fluoro-1H-indole-2-carboxylic acid trans (4-{2-[4-(4-fluoro-benzoyl)-piperidin-1-yl]-ethyl}-cyclohexyl)-amide | 493.6 | Trans-{1-[2-(4-Amino-cyclohexyl)-ethyl]-piperidin-4-yl}-(4-fluoro-phenyl)-methanone (trifluoro acetic acid salt) and 5-Fluoro-1H-indole-2-carboxylic acid | 494.0 |
| 30A3 | 5-Trifluoromethoxy-1H-indole-2-carboxylic acid (4-{2-[4-(4-fluoro-benzoyl)-piperidin-1-yl]-ethyl}-cyclohexyl)-amide | 559.6 | Trans-{1-[2-(4-Amino-cyclohexyl)-ethyl]-piperidin-4-yl}-(4-fluoro-phenyl)-methanone (trifluoro acetic acid salt) 5-Trifluoromethoxy-1H-indole-2-carboxylic acid | 560 |
| 30A4 | 5-Methoxy-1H-indole-2-carboxylic acid trans (4-{2-[4-(4-fluoro-benzoyl)-piperidin-1-yl]-ethyl}-cyclohexyl)-amide | 505.3 | Trans-{1-[2-(4-Amino-cyclohexyl)-ethyl]-piperidin-4-yl}-(4-fluoro-phenyl)-methanone (trifluoro acetic acid salt) and 5-Methoxy-1H-indole-2-carboxylic acid | 506.0 |
| 30A5 | 2-Cyclopropyl-N-trans (4-{2-[4-(4-fluoro-benzoyl)-piperidin-1-yl]-ethyl}-cyclohexyl)-acetamide | 414.5 | Trans-{1-[2-(4-Amino-cyclohexyl)-ethyl]-piperidin-4-yl}-(4-fluoro-phenyl)-methanone (trifluoro acetic acid salt) and 2-Cyclopropyl acid | 416 |
| 30A6 | N-trans (4-{2-[4-(4-Fluoro-benzoyl)-piperidin-1-yl]-ethyl}-cyclohexyl)-butyramide | 402.5 | Trans-{1-[2-(4-Amino-cyclohexyl)-ethyl]-piperidin-4-yl}-(4-fluoro-phenyl)-methanone (trifluoro acetic acid salt) and butyric acid | 403.0 |
| 30A7 | Thiophene-2-carboxylic acid trans (4-{2-[4-(4-fluoro-benzoyl)-piperidin-1-yl]-ethyl}-cyclohexyl)-amide | 442.6 | Trans-{1-[2-(4-Amino-cyclohexyl)-ethyl]-piperidin-4-yl}-(4-fluoro-phenyl)-methanone (trifluoro acetic acid salt) and Thiophene-2-carboxylic acid | 443.2 |
| 30A8 | 3H-Imidazo[4,5-b]pyridine-6-carboxylic acid (4-{2-[4-(4-fluoro-benzoyl)-piperidin-1-yl]-ethyl}-cyclohexyl)-amide | 477.5 | Trans-{1-[2-(4-Amino-cyclohexyl)-ethyl]-piperidin-4-yl}-(4-fluoro-phenyl)-methanone (trifluoro acetic acid salt) and 3H-Imidazo[4,5-b]pyridine-6-carboxylic acid | 478.3 |
| 30A9 | 2-Methyl-cyclopropanecarboxylic acid trans (4-{2-[4-(4-fluoro-benzoyl)-piperidin-1-yl]-ethyl}-cyclohexyl)-amide | 414.5 | Trans-{1-[2-(4-Amino-cyclohexyl)-ethyl]-piperidin-4-yl}-(4-fluoro-phenyl)-methanone (trifluoro acetic acid salt) and 2-Methyl-cyclopropanecarboxylic acid | 415.4 |
| 30A10 | 5-Methanesulfonyl-thiophene-2-carboxylic acid trans (4-{2-[4-(4-fluoro-benzoyl)-piperidin-1-yl]-ethyl}-cyclohexyl)-amide | 520.6 | Trans-{1-[2-(4-Amino-cyclohexyl)-ethyl]-piperidin-4-yl}-(4-fluoro-phenyl)-methanone (trifluoro acetic acid salt) and 5-Methanesulfonyl-thiophene-2-carboxylic acid | 521.3 |
| 30A11 | 6-Fluoro-N-trans (4-{2-[4-(4-fluoro-benzoyl)-piperidin-1-yl]-ethyl}-cyclohexyl)-nicotinamide | 455.5 | Trans-{1-[2-(4-Amino-cyclohexyl)-ethyl]-piperidin-4-yl}-(4-fluoro-phenyl)-methanone (trifluoro acetic acid salt) and 6-Fluoro nicotinic acid | 456.2 |
| 30A12 | 4-Methoxy-cyclohexanecarboxylic acid trans (4-{2-[4-(4-fluoro-benzoyl)-piperidin-1-yl]-ethyl}-cyclohexyl)-amide | 472.6 | Trans-{1-[2-(4-Amino-cyclohexyl)-ethyl]-piperidin-4-yl}-(4-fluoro-phenyl)-methanone (trifluoro acetic acid salt) and 4-Methoxy-cyclohexanecarboxylic acid | 473.3 |
| 30A13 | 4-Hydroxy-cyclohexanecarboxylic acid trans (4-{2-[4-(4-fluoro-benzoyl)-piperidin-1-yl]-ethyl}-cyclohexyl)-amide | 458.6 | Trans-{1-[2-(4-Amino-cyclohexyl)-ethyl]-piperidin-4-yl}-(4-fluoro-phenyl)-methanone (trifluoro acetic acid salt) and 4-Hydroxy-cyclohexanecarboxylic acid | 459.5 |

| Ex. No | Systematic name | MW | Starting materials | MW found (M + H)+ |
|---|---|---|---|---|
| 30A14 | N-trans (4-{2-[4-(4-Fluoro-benzoyl)-piperidin-1-yl]-ethyl}-cyclohexyl)-3-methoxy-butyramide | 432.6 | Trans {1-[2-(4-Amino-cyclohexyl)-ethyl]-piperidin-4-yl}-(4-fluoro-phenyl)-methanone and 3-methoxy-butyric acid (obtained by saponification of the ester) | 433.5 |
| 30A15 | N-trans (4-{2-[4-(4-Fluoro-benzoyl)-piperidin-1-yl]-ethyl}-cyclohexyl)-4-pyridin-3-yl-benzamide | 513.7 | Trans {1-[2-(4-amino-cyclohexyl)-ethyl]-piperidin-4-yl}-(4-fluoro-phenyl)-methanone and 4-pyridin-3-yl-benzoic acid | 514.1 |
| 30A16 | N-trans (4-{2-[4-(4-Fluoro-benzoyl)-piperidin-1-yl]-ethyl}-cyclohexyl)-4-pyridin-4-yl-benzamide | 513.7 | Trans {1-[2-(4-amino-cyclohexyl)-ethyl]-piperidin-4-yl}-(4-fluoro-phenyl)-methanone and 4-pyridin-4-yl-benzoic acid | 514.1 |
| 30A17 | N-trans (4-{2-[4-(4-Fluoro-benzoyl)-piperidin-1-yl]-ethyl}-cyclohexyl)-4-pyridin-2-yl-benzamide | 513.7 | Trans {1-[2-(4-amino-cyclohexyl)-ethyl]-piperidin-4-yl}-(4-fluoro-phenyl)-methanone and 4-pyridin-2-yl-benzoic acid | 514.1 |
| 30A18 | N-trans (4-{2-[4-(4-Fluoro-benzoyl)-piperidin-1-yl]-ethyl}-cyclohexyl)-4-(4-methyl-piperazin-1-yl)-benzamide | 534.7 | Trans {1-[2-(4-amino-cyclohexyl)-ethyl]-piperidin-4-yl}-(4-fluoro-phenyl)-methanone and 4-(4-methylpiperazino) benzoic acid | 535.1 |
| 30A19 | N-trans (4-{2-[4-(4-Fluoro-benzoyl)-piperidin-1-yl]-ethyl}-cyclohexyl)-6-morpholin-4-yl-nicotinamide | 522.6 | Trans {1-[2-(4-amino-cyclohexyl)-ethyl]-piperidin-4-yl}-(4-fluoro-phenyl)-methanone and 4-(4-methylpiperazino)benzoic acid | 523.7 |
| 30A20 | N-trans (4-{2-[4-(4-Fluoro-benzoyl)-piperidin-1-yl]-ethyl}-cyclohexyl)-4-phthalazin-1-yl-benzamide | 564.7 | Trans {1-[2-(4-amino-cyclohexyl)-ethyl]-piperidin-4-yl}-(4-fluoro-phenyl)-methanone and 4-phthalazin-1-yl-benzoic acid | 565.0 |
| 30A21 | N-trans (4-{2-[4-(4-Fluoro-benzoyl)-piperidin-1-yl]-ethyl}-cyclohexyl)-3-methoxy-4-pyridin-2-yl-benzamide | 543.7 | Trans {1-[2-(4-amino-cyclohexyl)-ethyl]-piperidin-4-yl}-(4-fluoro-phenyl)-methanone and 3-methoxy-4-pyridin-2-yl-benzoic acid | 544.0 |
| 30A22 | Biphenyl-4-carboxylic acid trans (4-{2-[4-(4-fluoro-benzoyl)-piperidin-1-yl]-ethyl}-cyclohexyl)-amide | 512.7 | Trans {1-[2-(4-amino-cyclohexyl)-ethyl]-piperidin-4-yl}-(4-fluoro-phenyl)-methanone and 4-diphenylcarbonic acid | 513.5 |
| 30A23 | 3-Methyl-chroman-3-carboxylic acid trans (4-{2-[4-(4-fluoro-benzoyl)-piperidin-1-yl]-ethyl}-cyclohexyl)-amide | 506.7 | Trans {1-[2-(4-amino-cyclohexyl)-ethyl]-piperidin-4-yl}-(4-fluoro-phenyl)-methanone and 3-methyl-chroman-3-carboxylic acid (prepared as described on WO200386288) | 507.3 |
| 30A24 | 2-Morpholin-4-yl-pyrimidine-5-carboxylic acid (4-{2-[4-(4-fluoro-benzoyl)-piperidin-1-yl]-ethyl}-cyclohexyl)-amide | 523.6 | Trans {1-[2-(4-amino-cyclohexyl)-ethyl]-piperidin-4-yl}-(4-fluoro-phenyl)-methanone and 2-Morpholin-4-yl-pyrimidine-5-carboxylic acid | 524.2 |
| 30A25 | 6-Morpholin-4-yl-pyridazine-3-carboxylic acid trans (4-{2-[4-(4-fluoro-benzoyl)-piperidin-1-yl]-ethyl}-cyclohexyl)-amide | 523.6 | Trans {1-[2-(4-amino-cyclohexyl)-ethyl]-piperidin-4-yl}-(4-fluoro-phenyl)-methanone and 6-Morpholin-4-yl-pyridazine-3-carboxylic acid | 524.0 |
| 30A26 | 5-Morpholin-4-yl-pyrazine-2-carboxylic acid trans (4-{2-[4-(4-fluoro-benzoyl)-piperidin-1-yl]-ethyl}-cyclohexyl)-amide | 523.6 | Trans {1-[2-(4-amino-cyclohexyl)-ethyl]-piperidin-4-yl}-(4-fluoro-phenyl)-methanone and 5-Morpholin-4-yl-pyrazine-2-carboxylic acid | 524.2 |

| Ex. No | Systematic name | MW | Starting materials | MW found (M + H)+ |
|---|---|---|---|---|
| 30A27 | N-trans (4-{2-[4-(4-Fluoro-benzoyl)-piperidin-1-yl]-ethyl}-cyclohexyl)-3-phenoxy-propionamide | 480.6 | Trans {1-[2-(4-amino-cyclohexyl)-ethyl]-piperidin-4-yl}-(4-fluoro-phenyl)-methanone and 3-phenoxypropionic acid | 481.2 |
| 30A28 | 3-Phenyl-propynoic acid trans (4-{2-[4-(4-fluoro-benzoyl)-piperidin-1-yl]-ethyl}-cyclohexyl)-amide | 460.6 | Trans {1-[2-(4-amino-cyclohexyl)-ethyl]-piperidin-4-yl}-(4-fluoro-phenyl)-methanone and phenylpropiolic acid | 461.2 |
| 30A29 | N-trans (4-{2-[4-(4-Fluoro-benzoyl)-piperidin-1-yl]-ethyl}-cyclohexyl)-3-hydroxy-2,2-dimethyl-propionamide | 432.6 | Trans {1-[2-(4-amino-cyclohexyl)-ethyl]-piperidin-4-yl}-(4-fluoro-phenyl)-methanone and 2,2-dimethyl-3-hydroxypropionic acid | 433.4 |
| 30A30 | 2-Fluoro-N-trans (4-{2-[4-(4-fluoro-benzoyl)-piperidin-1-yl]-ethyl}-cyclohexyl)-4-morpholin-4-yl-benzamide | 539.7 | Trans {1-[2-(4-amino-cyclohexyl)-ethyl]-piperidin-4-yl}-(4-fluoro-phenyl)-methanone and 2-fluoro-4-morpholin-4-yl-benzoic acid (prepared according to Biorganical and Medicinal chemistry letters (2005), 15(5), 1529-1534. | 540.1 |
| 30A31 | Benzo[1,3]dioxole-5-carboxylic acid trans (4-{2-[4-(4-fluoro-benzoyl)-piperidin-1-yl]-ethyl}-cyclohexyl)-amide | 480.57 | Trans {1-[2-(4-amino-cyclohexyl)-ethyl]-piperidin-4-yl}-(4-fluoro-phenyl)-methanone and 2-fluoro-4-morpholin-4-yl-benzoic acid | 481.1 |
| 30A32 | 3-Methyl-isoxazole-5-carboxylic acid trans (4-{2-[4-(4-fluoro-benzoyl)-piperidin-1-yl]-ethyl}-cyclohexyl)-amide | 441.5 | Trans {1-[2-(4-amino-cyclohexyl)-ethyl]-piperidin-4-yl}-(4-fluoro-phenyl)-methanone and 3-Methyl-isoxazole-5-carboxylic acid | 442.5 |
| 30A33 | 4-(3,3-Dimethyl-2-oxo-azetidin-1-yl)-N-trans (4-{2-[4-(4-fluoro-benzoyl)-piperidin-1-yl]-ethyl}-cyclohexyl)-benzamide | 533.7 | Trans {1-[2-(4-amino-cyclohexyl)-ethyl]-piperidin-4-yl}-(4-fluoro-phenyl)-methanone and 4-(3,3-Dimethyl-2-oxo-azetidin-1-yl)-benzoic acid | 534.2 |
| 30A34 | N-trans (4-{2-[4-(4-Fluoro-benzoyl)-piperidin-1-yl]-ethyl}-cyclohexyl)-4-morpholin-4-ylmethyl-benzamide | 535.7 | Trans {1-[2-(4-amino-cyclohexyl)-ethyl]-piperidin-4-yl}-(4-fluoro-phenyl)-methanone and 4-(Morpholinomethyl) benzoic acid | 536.2 |
| 30A35 | 2-Benzo[d]isoxazol-3-yl-N-(4-{2-[4-(4-fluoro-benzoyl)-piperidin-1-yl]-ethyl}-cyclohexyl)-acetamide | 491.6 | Trans {1-[2-(4-amino-cyclohexyl)-ethyl]-piperidin-4-yl}-(4-fluoro-phenyl)-methanone and 2-(1,2-benzisozaxol-3-yl) acetic acid | 492.4 |
| 30A36 | N-trans (4-{2-[4-(4-Fluoro-benzoyl)-piperidin-1-yl]-ethyl}-cyclohexyl)-2-(3-methyl-isoxazol-5-yl)-acetamide | 455.6 | Trans {1-[2-(4-amino-cyclohexyl)-ethyl]-piperidin-4-yl}-(4-fluoro-phenyl)-methanone and 3-Methyl-5-isoxazoleacetic acid | 456.3 |
| 30A37 | 2-(3,5-Dimethoxy-phenyl)-N-trans (4-{2-[4-(4-fluoro-benzoyl)-piperidin-1-yl]-ethyl}-cyclohexyl)-acetamide | 510.6 | Trans {1-[2-(4-amino-cyclohexyl)-ethyl]-piperidin-4-yl}-(4-fluoro-phenyl)-methanone and 3,5-diemthoxyphenylacetic acid | 511.5 |
| 30A38 | 2-Benzo[1,3]dioxol-5-yl-N-trans (4-{2-[4-(4-fluoro-benzoyl)-piperidin-1-yl]-ethyl}-cyclohexyl)-acetamide | 494.6 | Trans {1-[2-(4-amino-cyclohexyl)-ethyl]-piperidin-4-yl}-(4-fluoro-phenyl)-methanone and 3,4-methylenedioxyphenylacetic acid | 495.4 |

| Ex. No | Systematic name | MW | Starting materials | MW found (M + H)+ |
|---|---|---|---|---|
| 30A39 | Trans N-(4-{2-[4-(4-Fluoro-benzoyl)-piperidin-1-yl]-ethyl}-cyclohexyl)-2-methoxy-isonicotinamide | 467.5 | Trans {1-[2-(4-amino-cyclohexyl)-ethyl]-piperidin-4-yl}-(4-fluoro-phenyl)-methanone and 2-methoxy-isonicotinic acid | 468.4 |
| 30A40 | 4-tert-Butoxy-N-trans (4-{2-[4-(4-fluoro-benzoyl)-piperidin-1-yl]-ethyl}-cyclohexyl)-benzamide | 508.6 | Trans {1-[2-(4-amino-cyclohexyl)-ethyl]-piperidin-4-yl}-(4-fluoro-phenyl)-methanone and 4-tert-Butoxy benzoic acid | 509.5 |
| 30A41 | 4-Dimethylamino-N-trans (4-{2-[4-(4-fluoro-benzoyl)-piperidin-1-yl]-ethyl}-cyclohexyl)-benzamide | 479.6 | Trans {1-[2-(4-amino-cyclohexyl)-ethyl]-piperidin-4-yl}-(4-fluoro-phenyl)-methanone and 4-Dimethylamino benzoic acid | 480.3 |
| 30A42 | 4-(1,1-Dioxo-6-thiomorpholin-4-yl)-N-trans (4-{2-[4-(4-fluoro-benzoyl)-piperidin-1-yl]-ethyl}-cyclohexyl)-benzamide | 569.7 | Trans {1-[2-(4-amino-cyclohexyl)-ethyl]-piperidin-4-yl}-(4-fluoro-phenyl)-methanone and 4-(1,1-Dioxo-4-thiazinan-4-yl) benzenecarboxylic acid | 570.4 |
| 30A43 | 3-Fluoro-N-trans (4-{2-[4-(4-fluoro-benzoyl)-piperidin-1-yl]-ethyl}-cyclohexyl)-4-morpholin-4-yl-benzamide | 539.7 | Trans {1-[2-(4-amino-cyclohexyl)-ethyl]-piperidin-4-yl}-(4-fluoro-phenyl)-methanone and 3-fluoro-4-morpholin-4-yl-benzoic acid | 540.1 |
| 30A44 | N-trans (4-{2-[4-(4-Fluoro-benzoyl)-piperidin-1-yl]-ethyl}-cyclohexyl)-4-(3-hydroxy-pyrrolidin-1-yl)-benzamide | 521.7 | Trans {1-[2-(4-amino-cyclohexyl)-ethyl]-piperidin-4-yl}-(4-fluoro-phenyl)-methanone and 4-(3-hydroxy-pyrrolidin-1-yl)-benzoic acid (prepared according to Biorganic and Medicinal Chemistry Letters (2005), 15(5), 1529) | 522.5 |
| 30A45 | N-trans (4-{2-[4-(4-Fluoro-benzoyl)-piperidin-1-yl]-ethyl}-cyclohexyl)-4-(4-hydroxy-piperidin-1-yl)-benzamide | 535.7 | Trans {1-[2-(4-amino-cyclohexyl)-ethyl]-piperidin-4-yl}-(4-fluoro-phenyl)-methanone and 4-(4-hydroxy-piperidin-1-yl)-benzoic acid (prepared according to Biorganic and Medicinal Chemistry Letters (2005), 15(5), 1529). | 536.4 |
| 30A46 | N-trans (4-{2-[4-(4-Fluoro-benzoyl)-piperidin-1-yl]-ethyl}-cyclohexyl)-4-thiomorpholin-4-yl-benzamide | 537.8 | Trans {1-[2-(4-amino-cyclohexyl)-ethyl]-piperidin-4-yl}-(4-fluoro-phenyl)-methanone and 4-thiomorpholin-4-yl-benzoic acid (prepared according to Biorganic and Medicinal Chemistry Letters (2005), 15(5), 1529) | 538.4 |
| 30A47 | N-trans (4-{2-[4-(4-Fluoro-benzoyl)-piperidin-1-yl]-ethyl}-cyclohexyl)-4-piperidin-1-yl-benzamide | 519.7 | Trans {1-[2-(4-amino-cyclohexyl)-ethyl]-piperidin-4-yl}-(4-fluoro-phenyl)-methanone and 4-piperidine-1-yl-benzoic acid | 520.3 |
| 30A48 | N-trans (4-{2-[4-(4-Fluoro-benzoyl)-piperidin-1-yl]-ethyl}-cyclohexyl)-6-morpholin-4-yl-nicotinamide | 522.6 | Trans {1-[2-(4-amino-cyclohexyl)-ethyl]-piperidin-4-yl}-(4-fluoro-phenyl)-methanone and 4-morpholinonicotinic acid | 523.7 |
| 30A49 | 2,3-Dihydro-benzo[1,4]dioxine-2-carboxylic acid trans (4-{2-[4-(4-fluoro-benzoyl)-piperidin-1-yl]-ethyl}-cyclohexyl)-amide | 494.6 | Trans {1-[2-(4-amino-cyclohexyl)-ethyl]-piperidin-4-yl}-(4-fluoro-phenyl)-methanone and 1,4-benzodioxan-2-carboxylic acid | 495.3 |

-continued

| Ex. No | Systematic name | MW | Starting materials | MW found (M + H)+ |
|---|---|---|---|---|
| 30A50 | (1S,4R)-Bicyclo[2.2.1]heptane-2-carboxylic acid trans (4-{2-[4-(4-fluoro-benzoyl)-piperidin-1-yl]-ethyl}-cyclohexyl)-amide | 494.6 | Trans {1-[2-(4-amino-cyclohexyl)-ethyl]-piperidin-4-yl}-(4-fluoro-phenyl)-methanone and (1S,4R)-Bicyclo[2.2.1]heptane-2-carboxylic acid | 495.3 |
| 30A51 | (1R,4R)-7,7-Dimethyl-2-oxo-bicyclo[2.2.1]heptane-1-carboxylic acid trans (4-{2-[4-(4-fluoro-benzoyl)-piperidin-1-yl]-ethyl}-cyclohexyl)-amide | 496.6 | Trans {1-[2-(4-amino-cyclohexyl)-ethyl]-piperidin-4-yl}-(4-fluoro-phenyl)-methanone and (1R,4R)-7,7-Dimethyl-2-oxo-bicyclo[2.2.1]heptane-1-carboxylic acid | 497.4 |
| 30A52 | 4-Trifluoromethyl-cyclohexanecarboxylic acid trans (4-{2-[4-(4-fluoro-benzoyl)-piperidin-1-yl]-ethyl}-cyclohexyl)-amide | 510.62 | Trans {1-[2-(4-amino-cyclohexyl)-ethyl]-piperidin-4-yl}-(4-fluoro-phenyl)-methanone and 4-Trifluoromethyl-cyclohexanecarboxylic acid | 511.5 |
| 30A53 | 1-Methyl-cyclohexanecarboxylic acid trans (4-{2-[4-(4-fluoro-benzoyl)-piperidin-1-yl]-ethyl}-cyclohexyl)-amide | 456.6 | Trans {1-[2-(4-amino-cyclohexyl)-ethyl]-piperidin-4-yl}-(4-fluoro-phenyl)-methanone and 1-Methyl-cyclohexanecarboxylic acid | 457.5 |
| 30A54 | 4-Methyl-cyclohexanecarboxylic acid trans (4-{2-[4-(4-fluoro-benzoyl)-piperidin-1-yl]-ethyl}-cyclohexyl)-amide | 456.6 | Trans {1-[2-(4-amino-cyclohexyl)-ethyl]-piperidin-4-yl}-(4-fluoro-phenyl)-methanone and 4-Methyl-cyclohexanecarboxylic acid | 457.5 |
| 30A55 | 6-Hydroxy-bicyclo[2.2.2]octane-2-carboxylic acid trans (4-{2-[4-(4-fluoro-benzoyl)-piperidin-1-yl]-ethyl}-cyclohexyl)-amide | 484.6 | Trans {1-[2-(4-amino-cyclohexyl)-ethyl]-piperidin-4-yl}-(4-fluoro-phenyl)-methanone and 6-Hydroxy-bicyclo[2.2.2]octane-2-carboxylic acid | 485.4 |
| 30A56 | 1-Trifluoromethyl-cyclopropanecarboxylic acid trans (4-{2-[4-(4-fluoro-benzoyl)-piperidin-1-yl]-ethyl}-cyclohexyl)-amide | 456.6 | Trans {1-[2-(4-amino-cyclohexyl)-ethyl]-piperidin-4-yl}-(4-fluoro-phenyl)-methanone and 1-Trifluoromethyl-cyclopropanecarboxylic acid | 457.5 |
| 30A57 | 3-Chloro-cyclobutanecarboxylic acid trans (4-{2-[4-(4-fluoro-benzoyl)-piperidin-1-yl]-ethyl}-cyclohexyl)-amide | 449.01 | Trans {1-[2-(4-amino-cyclohexyl)-ethyl]-piperidin-4-yl}-(4-fluoro-phenyl)-methanone and 3-Chloro-cyclobutanecarboxylic acid | 449.5 |
| 30A58 | Acetic acid trans (4-{2-[4-(4-fluoro-benzoyl)-piperidin-1-yl]-ethyl}-cyclohexylcarbamoyl)-methyl ester | 432.5 | Trans {1-[2-(4-amino-cyclohexyl)-ethyl]-piperidin-4-yl}-(4-fluoro-phenyl)-methanone and acetoxyacetic acid | 433.4 |
| 30A59 | 1-Hydroxy-cyclopropanecarboxylic acid (trans-4-{2-[4-(4-fluoro-benzoyl)-piperidin-1-yl]-ethyl}-cyclohexyl)-amide | 416.5 | Trans {1-[2-(4-amino-cyclohexyl)-ethyl]-piperidin-4-yl}-(4-fluoro-phenyl)-methanone and 1-hydroxy-cyclopropanecarboxylic acid | 417.4 |
| 30A60 | Cyclobutanecarboxylic acid trans (4-{2-[4-(4-fluoro-benzoyl)-piperidin-1-yl]-ethyl}-cyclohexyl)-amide | 414.6 | Trans {1-[2-(4-amino-cyclohexyl)-ethyl]-piperidin-4-yl}-(4-fluoro-phenyl)-methanone and Cyclobutanecarboxylic acid | 415.5 |
| 30A61 | 4-Hydroxy-cyclohexanecarboxylic acid trans (4-{2-[4-(4-fluoro-benzoyl)-piperidin-1-yl]-ethyl}-cyclohexyl)-amide | 458.6 | Trans {1-[2-(4-amino-cyclohexyl)-ethyl]-piperidin-4-yl}-(4-fluoro-phenyl)-methanone and 4-Hydroxy-cyclohexanecarboxylic acid | 459.4 |

| Ex. No | Systematic name | MW | Starting materials | MW found (M + H)+ |
|---|---|---|---|---|
| 30A62 | 2,2-Difluoro-cyclopropanecarboxylic acid trans (4-{2-[4-(4-fluoro-benzoyl)-piperidin-1-yl]-ethyl}-cyclohexyl)-amide | 436.5 | Trans {1-[2-(4-amino-cyclohexyl)-ethyl]-piperidin-4-yl}-(4-fluoro-phenyl)-methanone and 2,2-Difluoro-cyclopropanecarboxylic acid | 437.2 |
| 30A63 | N-trans (4-{2-[4-(4-Fluoro-benzoyl)-piperidin-1-yl]-ethyl}-cyclohexyl)-2-morpholin-4-yl-benzamide | 522.4 | Trans {1-[2-(4-amino-cyclohexyl)-ethyl]-piperidin-4-yl}-(4-fluoro-phenyl)-methanone and 2-morpholino benzoic acid | 521.6 |

Example 30A64

Trans-(4-{2-[4-(4-Fluoro-benzoyl)-piperidin-1-yl]-ethyl}-cyclohexyl)-carbamic acid methyl ester Trans-{1-[2-(4-Amino-cyclohexyl)-ethyl]-piperidin-4-yl}-(4-fluoro-phenyl)-methanone (trifluoro acetic acid salt) (30 mg, 0.082 mmol) was dissolved in 1 ml dichlormethan. The reaction was cold down to 0° C. Dimethylpyrocarbonate (10.9 mg, 0.082 mmol) and triethylamine (8.3 mg, 0.082 mmol) were added. The reaction mixture was stirred over night at r.t. Aqueous solution of sodium bicarbonate was added until pH 8 and the water phase was extracted with dichloromethane. Chromatographic with dichloromethan/Methanol (1/0 to 8/2) yield the desired compound as a white solid (24 mg, 69.1%).

Example 30A65

5-(4-Methyl-piperazin-1-yl)-pyridine-2-carboxylic acid (4-{2-[4-(4-fluoro-benzoyl)-piperidin-1-yl]-ethyl}-cyclohexyl)-amide Step 1: 5-Bromo-pyridine-2-carboxylic acid (4-{2-[4-(4-fluoro-benzoyl)-piperidin-1-yl]-ethyl}-cyclohexyl)-amide The title compound, MS: m/e=515.9/517.9 (M+H+), was prepared according to the procedure described for the synthesis of example 1 from the respective trans-{1-[2-(4-amino-cyclohexyl)-ethyl]-piperidin-4-yl}-(4-fluoro-phenyl)-methanone (example 1, intermediate F) and 5-bromo-2-carboxy pyridine.

Step 2: 5-(4-Methyl-piperazin-1-yl)-pyridine-2-carboxylic acid (4-{2-[4-(4-fluoro-benzoyl)-piperidin-1-yl]-ethyl}-cyclohexyl)-amide 5-Bromo-pyridine-2-carboxylic acid (4-{2-[4-(4-fluoro-benzoyl)-piperidin-1-yl]-ethyl}-cyclohexyl)-amide (80 mg, 0.15 mmol) and 1-methylpiperazine (31 µl, 0.28 mmol) were dissolved in 2 ml dioxane. 4,5-bis(diphenylphosphino)-9,9-dimethylxanthene (9 mg, 0.016 mmol), cesium carbonate (76 mg, 0.23 mmol), water (1 µl, 0.078 mmol) and tri(dibenzylideneacetone)dipalladium chloroform complex (8 mg, 0.008 mmol) were added and the reaction mixture was stirred for 16 hrs at 110° C. The reaction mixture was then evaporated and purified by flash chromatography on silica gel (dichloromethane/methanol 100:0->90:10 gradient). The desired product was obtained as a light red solid (33 mg, 40%), MS: m/e=536.0 (M+H+).

Example 30A66

5-Morpholin-4-yl-pyridine-2-carboxylic acid (4-{2-[4-(4-fluoro-benzoyl)-piperidin-1-yl]-ethyl}-cyclohexyl)-amide The title compound, MS: m/e=523.2 (M+H+), was prepared in accordance with the general method of example 30A65, step 2 from 5-bromo-pyridine-2-carboxylic acid (4-{2-[4-(4-fluoro-benzoyl)-piperidin-1-yl]-ethyl}-cyclohexyl)-amide and morpholine.

Example 30A67

5-Phenyl-pyridine-2-carboxylic acid (4-{2-[4-(4-fluoro-benzoyl)-piperidin-1-yl]-ethyl}-cyclohexyl)-amide 5-Bromo-pyridine-2-carboxylic acid (4-{2-[4-(4-fluoro-benzoyl)-piperidin-1-yl]-ethyl}-cyclohexyl)-amide (example 30A66, step 1) (80 mg, 0.155 mmol) and phenylboronic acid (27 mg, 0.22 mmol) were dissolved under argon in 0.4 ml 2M sodium carbonate and 1.6 ml 1,2-dimethoxyethane. Triphenylphosphine (16 mg, 0.062 mmol) and Pd(II) acetate (7 mg, 0.03 mmol) were added and the mixture stirred at 85° C. for 16 hrs. The reaction mixture was extracted with water and two times dichloromethane. The organic extracts were washed with water and brine, dried with sodium sulfate, filtered and evaporated. The crude product was purified by flash chromatography on silica gel (dichloromethane/methanol 100:0->90:10 gradient). The desired compound was obtained as a brown solid (36 mg, 45%), MS: m/e=514.1 (M+H+).

Example 31

Quinoline-4-carboxylic acid (4-{2-[4-(4-fluoro-benzoyl)-piperidin-1-yl]-ethyl}-cyclohexyl)-amide Intermediate B Trans-(4-Amino-cyclohexyl)-acetic acid ethyl ester Step 1

(4-Nitro-phenyl)-acetic acid (0.005 g, 276 mmol) was added to a stirred solution of 22.08 g of 50% sodium hydroxide solution in 450 mL deionizated water. The clear yellow solution was transferred into a high-pressure autoclave that it charged with 30 g (511 mmol) of water-wet sponge nickel catalyst. The autoclave was sealed, flushed with nitrogen and then pressurized to 115 bar with hydrogen. The reaction mixture was stirred and heated to 125° C. for 48 h. At that time the autoclave was cooled, vented and charged under nitrogen with another 30 g (511 mmol) of the sponge nickel catalyst. The autoclave was flushed again with nitrogen and then pressurized to 115 bar and the vessel is heated to 130° C. while stirring (a maximum pressure of 130 bars is observed). Hydrogenation is continued for 5 days to 130° C. The autoclave is then cooled, vented and flushed with nitrogen and the contents are removed and filtered through filter aid to remove catalyst. After removal of the solvent a crude was obtained. The intermediated is used directly in the next step without purification. MS (m/e): 158.3 (M+H$^+$)

Step 2

A solution of the Trans-(4-amino-cyclohexyl)-acetic acid obtained (74 g, 476 mmol) was adjusted to pH 5 with 25% HCl. The mixture was evaporated to dryness and dried under vacuum overnight. The residue was suspended in 146 mL of a 6.5N ethanolic HCl solution and 0.6 L of ethanol was added to the mixture. After 4 h refluxing, the mixture was cooled, filtered and the filtrate was concentrated to dryness under vacuum. The residue was dissolved in ethanol, treated with ether and cooled overnight in the refrigerator. to give the Trans-(4-Amino-cyclohexyl)-acetic acid ethyl ester hydrochloride (19.7 g, 32% on the two steps) as a white solid which was filtered and dried under vacuum. MS (m/e): 186.1 (M+H$^+$)

Intermediate G

Step 1

{Trans-4-[(Quinoline-4-carbonyl)-amino]-cyclohexyl}-acetic acid ethyl ester hydrochloride salt A mixture of Trans-(4-Amino-cyclohexyl)-acetic acid ethyl ester hydrochloride (3.63 g, 17 mmol) is solved in dichloromethane (115 mL) and quinoline-4-carbonyl chloride hydrochloride is added (4.184 g, 18 mmol) followed by the slow addition of triethylamine (11.3 mL, 81 mmol) at 0° C. The mixture is stirred at room temperature overnight and the salts obtained are removed by filtration and the filtrate is extracted. The organic layer is washed with NaHCO3 and brine. The organic phases are dried and concentrated to obtain 3.8 g of a crude. After a flash chromatography with heptane/AcOEt 4:1 to AcOEt a solid was obtained that was recrystallized with EtOAc and n-heptane to obtain the title compound as a pink solid (2.72 g, 42% yield). MS (m/e): 341.3 (M+H$^+$).

Step 2

Trans-{4-[(Quinoline-4-carbonyl)-amino]-cyclohexyl}-acetic acid

4-[(Quinoline-4-carbonyl)-amino]-cyclohexyl}-acetic acid ethyl ester hydrochloride salt (2.7 g, 8 mmol) was reacted with lithium hydroxide monohydrate (3.33 g, 79 mmol) in a mixture of water (65 mL) and THF (130 mL) and the mixture was heated at reflux for 5 hours. A ⅔ of the mixture was evaporated and HCl 37% was added until pH 7. The mixture is then evaporated to dryness and 30 mL of water is added and the suspension is filtered to obtain a solid that was recrystallized on toluene (2.2 g, 88.6% yield). MS (m/e): 313.1 (M+H$^+$).

Intermediate H

Trans-{4-[(Quinoline-4-carbonyl)-amino]-cyclohexyl}-thioacetic acid S-ethyl ester 2.19 g of Trans-{4-[(Quinoline-4-carbonyl)-amino]-cyclohexyl}-acetic acid (7 mmol) was added in 1300 mL of dichloromethane. Then 1.8 mL of oxalyl chloride is added (21 mmol). The suspension was heated to reflux for 3 hours and then the cloudy mixture is concentrated under vacuum. The residue is taken up in 500 mL of dichloromethane as a suspension and (1.28 g, 21 mmol) sodium ethylthiolate freshly prepared from 1.45 mL of ethanothiol and 12.07 mL of Butyl lithium (1.6 M in toluene) at 0° C. and by stirring in dimethoxyethane (20 mL) for 1 h at room temperature. The reaction mixture was stirred overnight. NaHCO$_3$ was added and the organic phase was extracted three times with dichloromethane. The organic phases were dried and concentrated and the residue was chromatographied with heptane/AcOEt 1:1 to AcOEt to yield the title compound as a solid (1.97 g, 78.9% yield). MS (m/e): 357.3 (M+H$^+$).

Intermediate I

Quinoline-4-carboxylic acid trans-[4-(2-oxo-ethyl)-cyclohexyl]-amide

Trans-{4-[(Quinoline-4-carbonyl)-amino]-cyclohexyl}-thioacetic acid S-ethyl ester (1.87 g, 5 mmol) was solved in acetone/methylene chloride (40/40 mL), 0.8 g of molecular sieves were added to the mixture and the solution was stirred for 0.5 h. Then 0.558 g (1 mmol) of palladium on active charcoal 10% was added followed by 1.25 mL (8 mmol) of triethyl-silane. The reaction was stirred for 1.5 h at room temperature and additional 0.558 g (1 mmol) of palladium on active charcoal 10% and 1.25 mL (8 mmol) of triethyl-silane were added and the stirring was continued for another hour. The mixture was filtrated through celite and the mother liquid was concentrated to obtain after chromatography using heptane/AcOEt 1:1 to AcOEt 1.1 (37.1 mmol, 70.8% yield) of the final compound. MS (m/e): 297.3 (M+H$^+$)

Quinoline-4-carboxylic acid trans-(4-{2-[4-(4-fluoro-benzoyl)-piperidin-1-yl]-ethyl}-cyclohexyl)-amide 4-(4-fluorobenzoyl)piperidine (trifluoro-acetic acid salt) (0.020 g, 0.062 mmol) was solved in 1,2-dichloromethane (0.300 mL) and Quinoline-4-carboxylic acid trans-[4-(2-oxo-ethyl)-cyclohexyl]-amide (0.020 g, 0.067 mmol) was added. Methanol (0.200 mL) was added to the mixture and it was stirred overnight. Sodium triacetoxyborohydride (0.024, 0.11 mmol) was added to the clear solution that was stirred 10 hours at room temperature. The mixture was concentrated to dryness and the residue was taken up on methanol and purified with preparative HPLC on reversed phase eluting with acetonitrile/water. The combined producted fractions were evaporated under reduced pressure to yield 0.03 g of a white solid (0.06 mmol, 99%). MS (m/e): 488.3 (M+H$^+$)

According to the procedure described for the synthesis of example 31 further derivatives have been synthesized from the respective Quinoline-4-carboxylic acid trans-[4-(2-oxo-ethyl)-cyclohexyl]-amide and the corresponding phenyl or heteroaryl piperidin-4-yl-methanone (commercial availables, obtained by methods known on the art or by methods described on this patent).

| Ex. No | Systematic name | MW | Starting materials | MW found (M + H)+ |
|---|---|---|---|---|
| 31 | Quinoline-4-carboxylic acid trans-(4-{2-[4-(4-fluoro-benzoyl)-piperidin-1-yl]-ethyl}-cyclohexyl)-amide | 487.6 | Quinoline-4-carboxylic acid trans-[4-(2-oxo-ethyl)-cyclohexyl]-amide and 4-(4-fluorobenzoyl) piperidine (trifluoro-acetic acid salt) | 488.3 |
| 32 | Quinoline-4-carboxylic acid trans-(4-{2-[4-(4-methoxy-benzoyl)-piperidin-1-yl]-ethyl}-cyclohexyl)-amide | 499.6 | Quinoline-4-carboxylic acid trans-[4-(2-oxo-ethyl)-cyclohexyl]-amide and (4-methoxyphenyl)(4-piperidyl) methanone hydrochloride | 500.3 |
| 33 | Quinoline-4-carboxylic acid trans-{4-[2-(4-benzoyl-4-hydroxy-piperidin-1-yl)-ethyl]-cyclohexyl}-amide | 485.6 | Quinoline-4-carboxylic acid trans-[4-(2-oxo-ethyl)-cyclohexyl]-amide and 4-hydroxy-4-piperidyl phenyl ketone hydrochloride | 486.4 |
| 34 | Quinoline-4-carboxylic acid trans-{4-[2-(4-benzoyl-4-fluoro-piperidin-1-yl)-ethyl]-cyclohexyl}-amide | 487.6 | Quinoline-4-carboxylic acid trans-[4-(2-oxo-ethyl)-cyclohexyl]-amide and (4-Fluoro-piperidin-4-yl)-phenyl-methanone (trifluoro-acetic acid salt) | 488.4 |
| 35 | Quinoline-4-carboxylic acid trans-(4-{2-[4-(3,4-dichloro-benzoyl)-piperidin-1-yl]-ethyl}-cyclohexyl)-amide | 538.52 | Quinoline-4-carboxylic acid trans-[4-(2-oxo-ethyl)-cyclohexyl]-amide and (3,4-Dichloro-phenyl)-piperidin-4-yl-methanone | 538.4 |

Example 36

N-trans-(4-{2-[4-(4-Fluoro-benzoyl)-piperidin-1-yl]-ethyl}-cyclohexyl)-acetamide Trans-{1-[2-(4-Amino-cyclohexyl)-ethyl]-piperidin-4-yl}-(4-fluoro-phenyl)-methanone (intermediate F, example 1) (0.03 g, 0.09 mmol) is suspended in dichloromethane (0.300 mL) and triethylamine is added (0.01 mL, 0.094 mmol) followed by acetylchloride (0.010 mL, 0.094 mmol) and the mixture was stirred for 2 hours at room temperature until TLC indicated the end of the reaction. The solvent was removed and DMF (0.8 mL) was added and the solution was purified with preparative HPLC on reversed phase eluting with acetonitrile/water (0.05% Et$_3$N). The combined producted fractions were evaporated under reduced pressure to yield 0.008 g of a off-white solid (0.02 mmol, 22.2%). MS (m/e): 375.3 (M+H$^+$)

According to the procedure described for the synthesis of example 36 further derivatives have been synthesized from the Trans-{1-[2-(4-Amino-cyclohexyl)-ethyl]-piperidin-4-yl}-(4-fluoro-phenyl)-methanone and the corresponding acyl chlorides. They comprise examples 36 and 37.

| Ex. No | Systematic name | MW | Starting materials | MW found (M + H)+ |
|---|---|---|---|---|
| 36 | N-trans-(4-{2-[4-(4-Fluoro-benzoyl)-piperidin-1-yl]-ethyl}-cyclohexyl)-acetamide | 374.5 | Trans-{1-[2-(4-Amino-cyclohexyl)-ethyl]-piperidin-4-yl}-(4-fluoro-phenyl)-methanone and acetylchloride | 375.2 |
| 37 | Morpholine-4-carboxylic acid trans (4-{2-[4-(4-fluoro-benzoyl)-piperidin-1-yl]-ethyl}-cyclohexyl)-amide | 445.5 | Trans-{1-[2-(4-Amino-cyclohexyl)-ethyl]-piperidin-4-yl}-(4-fluoro-phenyl)-methanone and 4-morpholinylcarbonyl chloride | 446.3 |

Example 38

Trans-1-(2,4-Dichloro-phenyl)-3-(4-{2-[4-(4-fluoro-benzoyl)-piperidin-1-yl]-ethyl}-cyclohexyl)-urea Trans-{1-[2-(4-Amino-cyclohexyl)-ethyl]-piperidin-4-yl}-(4-fluoro-phenyl)-methanone (example 1, intermediate F) (0.03 g, 0.09 mmol) was suspended in acetonitrile (0.300 mL) and 2,4-Dichlorophenyl isocyanate was added (0.019 g, 0.1 mmol) and the mixture was stirred for 2 hours at room temperature until TLC indicated the end of the reaction. The solvent was removed and the crude was purified with chromatography eluting with dichloromethane/methanol (1/0 to 9/1). The combined product fractions were evaporated under reduced pressure to yield 0.001 g of a white solid (0.019 mmol, 21%). MS (m/e): 375.3 (M+H$^+$)

According to the procedure described for the synthesis of example 38 further derivatives have been synthesized from the respective Trans-{1-[2-(4-Amino-cyclohexyl)-ethyl]-piperidin-4-yl}-(4-fluoro-phenyl)-methanone and the corresponding isocyanate. They comprise examples 38 to 41.

| Ex. No | Systematic name | MW | Starting materials | MW found (M + H)+ |
|---|---|---|---|---|
| 38 | Trans-1-(2,4-Dichloro-phenyl)-3-(4-{2-[4-(4-fluoro-benzoyl)-piperidin-1-yl]-ethyl}-cyclohexyl)-urea | 520.4 | Trans-{1-[2-(4-Amino-cyclohexyl)-ethyl]-piperidin-4-yl}-(4-fluoro-phenyl)-methanone and 2,4-Dichlorophenyl isocyanate | 520.5 |
| 39 | Trans-1-(4-Chloro-phenyl)-3-(4-{2-[4-(4-fluoro-benzoyl)-piperidin-1-yl]-ethyl}-cyclohexyl)-urea | 520.4 | Trans-{1-[2-(4-Amino-cyclohexyl)-ethyl]-piperidin-4-yl}-(4-fluoro-phenyl)-methanone and 4-Chlorophenyl isocyanate | 520.5 |
| 40 | Trans-1-(4-Ethoxy-phenyl)-3-(4-{2-[4-(4-fluoro-benzoyl)-piperidin-1-yl]-ethyl}-cyclohexyl)-urea | 486.03 | Trans-{1-[2-(4-Amino-cyclohexyl)-ethyl]-piperidin-4-yl}-(4-fluoro-phenyl)-methanone and 4-Ethoxyphenyl isocyanate | 486.5 |
| 41 | Trans-1-(4-{2-[4-(4-Fluoro-benzoyl)-piperidin-1-yl]-ethyl}-cyclohexyl)-3-p-tolyl-urea | 465.6 | Trans-{1-[2-(4-Amino-cyclohexyl)-ethyl]-piperidin-4-yl}-(4-fluoro-phenyl)-methanone and p-tolyl isocyanate | 466.1 |

Example 42

Trans-1-(4-Chloro-phenyl)-3-(4-{2-[4-(4-fluoro-benzoyl)-piperidin-1-yl]-ethyl}-cyclohexyl)-1-methyl-urea Trans-{1-[2-(4-Amino-cyclohexyl)-ethyl]-piperidin-4-yl}-(4-fluoro-phenyl)-methanone (example 1, intermediate F) (0.05 g, 0.1 mmol) is suspended in acetonitrile (1 mL) and (4-chloro-phenyl)methyl carbamic acid 4-nitro-phenyl ester (prepared from 4-chloro-N-methylaniline and 4-nitrophenyl chloroformate with triethylamine in dichloromethane stirring at room temperature) was added (0.034 g, 0.1 mmol) followed by N,N-diisopropyl ethyl amine (0.04 mL, 0.2 mmol) and the mixture was stirred for 24 hours at 75° C. until TLC indicated the end of the reaction. The solvent was removed and crude was purified with chromatography eluting with dichloromethane/methanol (1/0 to 9/1). The combined product fractions were evaporated under reduced pressure to yield 0.02 g of a white solid (0.04 mmol, 40%). MS (m/e): 501.2 (M+H$^+$).

| Ex. No | Systematic name | MW | Starting materials | MW found (M + H)+ |
|---|---|---|---|---|
| 42 | Trans-1-(4-Chloro-phenyl)-3-(4-{2-[4-(4-fluoro-benzoyl)-piperidin-1-yl]-ethyl}-cyclohexyl)-1-methyl-urea | 500.1 | Trans-{1-[2-(4-Amino-cyclohexyl)-ethyl]-piperidin-4-yl}-(4-fluoro-phenyl)-methanone and (4-chloro-phenyl) methyl carbamic acid 4-nitro-phenyl ester | 501.2 |

Example 42A1

2,3-Dihydro-indole-1-carboxylic acid (4-{2-[4-(4-fluoro-benzoyl)-piperidin-1-yl]-ethyl}-cyclohexyl)-amide Trans {1-[2-(4-amino-cyclohexyl)-ethyl]-piperidin-4-yl}-(4-fluoro-phenyl)-methanone (example 1, intermediate F) (80 mg, 0.24 mmol) was dissolved in 1.5 ml dichloromethane and N-ethyldiisopropylamine (0.33 ml, 1.93 mmol) was added. Triphosgene (79 mg, 0.27 mmol) was added carefully and the solution stirred for 30 minutes at room temperature. Indoline (32 mg, 0.27 mmol) was added and stirred for 30 minutes at room temperature. The reaction mixture was extracted with sat. NaHCO$_3$-solution and dichloromethane. The organic extracts were washed with brine, dried with sodium sulfate, filtered and evaporated. The crude product was purified by flash chromatography on silica gel (dichloromethane/methanol 100:0->90:10 gradient). The desired compound was obtained as a white solid (51 mg, 44%), MS: m/e=478.2 (M+H$^+$).

According to the procedure described for the synthesis of example 42A1 further derivatives have been synthesized from the respective Trans-{1-[2-(4-Amino-cyclohexyl)-ethyl]-piperidin-4-yl}-(4-fluoro-phenyl)-methanone (example 1, intermediate F) and the corresponding amine. They comprise examples 42A2 to 42A7.

Example 43

N-{(Trans-2-[4-(4-Fluoro-benzoyl)-piperidin-1-ylmethyl]-cyclopropylmethyl}-3-(5-methyl-[1,2,4]oxadiazol-3-yl)-benzamide

Intermediate K

Trans-2-[tert-Butoxycarbonylamino-(toluene-4-sulfonyl)-methyl]-cyclopropanecarboxylic acid ethyl ester 2-Formyl-cyclopropanecarboxylic acid ethyl ester (88-90% trans isomer) (2.9 g, 20.4 mmol) is solved in methanol and 2.4 g (20.49 mmol) of tert-butylcarbamate was added followed by sodium p-toluensulfinate in water (40 mL). After stirring at room temperature 5 mL (132.5 mmol) of formic acid was added and the mixture is stirred for 70 minutes until the product precipitated. The solid was filtrated and washed with water and heptane and dried under high vacuum to obtain 3.6 g. (44.5% yield) of the title compound (only the trans isomer) as a white solid. MS (m/e): 384.5 (M+H$^+$)

Intermediate L

Trans-2-(tert-Butoxycarbonylamino-methyl)-cyclopropanecarboxylic acid ethyl ester Sodium Borohydride (2.3 g, 58.55 mol) was suspended in tetrahydrofuran (150 mL) and 4 mL of water was added. (13.3 g, 33.46 mmol) of trans-2-[tert-Butoxycarbonylamino-(tolu-

| Ex. No | Systematic name | MW | Starting materials | MW found (M + H)+ |
|---|---|---|---|---|
| 42A2 | 6-Trifluoromethyl-2,3-dihydro-indole-1-carboxylic acid trans (4-{2-[4-(4-fluoro-benzoyl)-piperidin-1-yl]-ethyl}-cyclohexyl)-amide | 545.6 | Trans-{1-[2-(4-Amino-cyclohexyl)-ethyl]-piperidin-4-yl}-(4-fluoro-phenyl)-methanone and 6-(trifluoromethyl)indoline | 546.2 |
| 42A3 | 1,3-Dihydro-isoindole-2-carboxylic acid trans (4-{2-[4-(4-fluoro-benzoyl)-piperidin-1-yl]-ethyl}-cyclohexyl)-amide | 477.6 | Trans {1-[2-(4-amino-cyclohexyl)-ethyl]-piperidin-4-yl}-(4-fluoro-phenyl)-methanone and isoinoline | 478.2 |
| 42A4 | 3,4-Dihydro-1H-isoquinoline-2-carboxylic acid trans (4-{2-[4-(4-fluoro-benzoyl)-piperidin-1-yl]-ethyl}-cyclohexyl)-amide | 491.7 | Trans {1-[2-(4-amino-cyclohexyl)-ethyl]-piperidin-4-yl}-(4-fluoro-phenyl)-methanone and 1,2,3,4-tetrahydroisoquinoline | 492.1 |
| 42A5 | 3-Phenoxy-pyrrolidine-1-carboxylic acid trans (4-{2-[4-(4-fluoro-benzoyl)-piperidin-1-yl]-ethyl}-cyclohexyl)-amide | 521.7 | Trans {1-[2-(4-amino-cyclohexyl)-ethyl]-piperidin-4-yl}-(4-fluoro-phenyl)-methanone and (RS)-3-phenoxy-pyrrolidine | 522.2 |
| 42A6 | 1,1-Dioxo-thiomorpholine-4-carboxylic acid (4-{2-[4-(4-fluoro-benzoyl)-piperidin-1-yl]-ethyl}-cyclohexyl)-amide | 493.6 | Trans {1-[2-(4-amino-cyclohexyl)-ethyl]-piperidin-4-yl}-(4-fluoro-phenyl)-methanone and (1,1-Dioxo-thiomorpholine-4-carboxylic acid | 494.4 |
| 42A7 | Trans-3-(4-{2-[4-(4-Fluoro-benzoyl)-piperidin-1-yl]-ethyl}-cyclohexyl)-1,1-dimethyl-urea | 403.5 | Trans {1-[2-(4-amino-cyclohexyl)-ethyl]-piperidin-4-yl}-(4-fluoro-phenyl)-methanone and dimethyl amine | 404.4 | ene-4-sulfonyl)-methyl]-cyclopropanecarboxylic acid ethyl ester was added portionwise (0.8 g portions) and the temperature was kept to 18-30° C. After 1.5 h water (4 mL) and 0.4 g (10.15 mmol) of sodium borohydride were added again. The resulting mixture was quenched with ammonium chloride 2M (300 mL) and 100 mL of 1M $K_2CO_3$ and stirring was continued for 0.5 h. The organic layer was separated and the aqueous phase was extracted with ethyl acetate (300 mL) and the combined organic layers were dried over $MgSO_4$ and concentrated to dryness under vacuum and purified with column chromatography on silica with heptane/AcOEt (9/1) to obtain 7.5 g (92.1% yield) of the title compound. as a white solid. MS (m/e): 244.1 (M+H$^+$)

Intermediate M

Trans-(2-Formyl-cyclopropylmethyl)-carbamic acid tert-butyl ester

To a solution of Trans-2-(tert-Butoxycarbonylamino-methyl)-cyclopropanecarboxylic acid ethyl ester (0.320 g, 1.3 mmol), in toluene (5 mL) at −78° C. a 1.2M solution of DIBAL-H (1.86 mL, 2.2 mmol) in toluene was added. The mixture was stirred at −78° C. until TLC after 0.5 h indicated completion of the reaction. A saturated solution of sodium tartrate was added and the water was extracted three times with dichloromethane. The combined organic layers were washed with water and brine, dried over magnesium sulfate, filtered and evaporated. The crude product was used without purification on the next step. MS (m/e): 200.3 (M+H$^+$)

Intermediate N

{Trans-2-[4-(4-Fluoro-benzoyl)-piperidin-1-ylmethyl]-cyclopropylmethyl}-carbamic acid tert-butyl ester A mixture of 4-(4-fluorobenzoyl)piperidine (0.300 g, 1.2 mmol), Trans-(2-Formyl-cyclopropylmethyl)-carbamic acid tert-butyl ester (0.294 g, 1.2 mmol), in 1, 2 dichloroethane (2 mL) was stirred for 4 h at room temperature and sodium triacetoxyborohydride (0.470 g, 2.2 mmol) was added and the resulting solution was stirred for 12 hours until the TLC indicated completion of the reaction. The mixture was filtrated and concentrated to dryness and purified with column chromatography on silica gel using $CH_2Cl_2$-$CH_2Cl_2$/MeOH (1-9:1). The product fractions were concentrated to give 0.288 g (0.74 mmol, 60% yield) of a white solid. MS (m/e): 391.3 (M+H$^+$).

[1-(Trans-2-Aminomethyl-cyclopropylmethyl)-piperidin-4-yl]-(4-fluoro-phenyl)-methanone; trifluoro-acetic acid salt 0.288 g (0.74 mmol) of {trans-2-[4-(4-Fluoro-benzoyl)-piperidin-1-ylmethyl]-cyclopropylmethyl}-carbamic acid tert-butyl ester is solved in dichloromethane (5 mL) and trifluoroacetic acid is added at 0° C. (0.757 mL, 6.6 mmol) and the mixture is stirred at room temperature overnight. $NaHCO_3$ is slowly added until pH 9 and the mixture extracted with 3 times with dichloromethane and ethyl acetate. The solvent was evaporated to yield 0.308 g (0.76 mmol, 100%) of a white solid that was used without purification on the next steps. MS (m/e): 291.2 (M+H$^+$).

N-{(Trans-2-[4-(4-Fluoro-benzoyl)-piperidin-1-ylmethyl]-cyclopropylmethyl}-3-(5-methyl-[1,2,4]oxadiazol-3-yl)-benzamide 3-(5-methyl-1,2,4-oxadiazol-3-yl)benzoic acid (0.015 g, 0.074 mmol), 2-(1H-benzotriazol-1-yl)-1,1,3,3-tetramethyl uronium tetrafluoroborate (0.024 g, 0.074 mmol) and (0.04 mL, 0.224 mmol) of N-ethyldiisopropylamine were stirred in 0.3 mL of DMF for 0.5 h at room temperature and [1-(Trans-2-Aminomethyl-cyclopropylmethyl)-piperidin-4-yl]-(4-fluoro-phenyl)-methanone; trifluoro-acetic acid salt (0.030 g, 0.074 mmol) was added. The mixture was stirred for 12 hours at room temperature. The mixture was concentrated to dryness and the residue was purified with chromatography using dichloromethane and methanol (9:1). The combined producted fractions were evaporated under reduced pressure to yield 0.02 g of a light brown solid (0.04 mmol, 56.6%). MS (m/e): 477.0 (M+H$^+$).

According to the procedure described for the synthesis of example 43 further amide derivates were synthesized from [1-(Trans-2-Aminomethyl-cyclopropylmethyl)-piperidin-4-yl]-(4-fluoro-phenyl)-methanone (trifluoroacetic acid salt) and the respective commercially available acid. The purification was performed with preparative HPLC on reversed phase column material eluting with a gradient formed from acetonitrile/water (0.05% $Et_3N$). The evaporation of the product fractions yielded the respective amides which comprise examples 43 to example 45.

| Ex. No | Systematic name | MW | Starting materials | MW found (M + H)+ |
|---|---|---|---|---|
| 43 | N-{Trans-2-[4-(4-Fluoro-benzoyl)-piperidin-1-ylmethyl]-cyclopropylmethyl}-3-(5-methyl-[1,2,4]oxadiazol-3-yl)-benzamide | 476.5 | [1-(Trans-2-Aminomethyl-cyclopropylmethyl)-piperidin-4-yl]-(4-fluoro-phenyl)-methanone; trifluoro-acetic acid salt and 3-(5-methyl-1,2,4-oxadiazol-3-yl) benzoic acid | 477.0 |
| 44 | 2-(4-Chloro-phenyl)-N-{Trans-2-[4-(4-fluoro-benzoyl)-piperidin-1-ylmethyl]-cyclopropylmethyl}-isobutyramide | 471.02 | [1-(Trans-2-Aminomethyl-cyclopropylmethyl)-piperidin-4-yl]-(4-fluoro-phenyl)-methanone; trifluoro-acetic acid salt and 4-chloro-alpha, alpha-dimethylphenyl acetic acid | 471.3 |
| 45 | 4-Chloro-N-{Trans-2-[4-(4-fluoro-benzoyl)-piperidin-1-ylmethyl]-cyclopropylmethyl}-benzamide | 428.9 | [1-(Trans-2-Aminomethyl-cyclopropylmethyl)-piperidin-4-yl]-(4-fluoro-phenyl)-methanone; trifluoro-acetic acid salt and 4-Chlorobenzoic acid | 429.5 |

Example 46

1-(4-Chloro-phenyl)-3-{Trans-2-[4-(4-fluoro-benzoyl)-piperidin-1-ylmethyl]-cyclopropylmethyl}-urea The title compound was synthesized from [1-(Trans-2-Aminomethyl-cyclopropylmethyl)-piperidin-4-yl]-(4- fluoro-phenyl)-methanone, trifluoroacetic acid salt and 4-chlorophenyl isocyanate in acetonitrile according to the procedure described for example 21. MS (m/e): 444.0 (M+H⁺)

| Ex. No | Systematic name | MW | Starting materials | MW found (M + H)+ |
|---|---|---|---|---|
| 46 | 1-(4-Chloro-phenyl)-3-{Trans-2-[4-(4-fluoro-benzoyl)-piperidin-1-ylmethyl]-cyclopropylmethyl}-urea | 443.95 | [1-(Trans-2-Aminomethyl-cyclopropylmethyl)-piperidin-4-yl]-(4-fluoro-phenyl)-methanone, trifluoroacetic acid salt and and 4-chlorophenyl isocyanate | 444.0 |

Example 47

2-(4-Chloro-phenyl)-N-{trans-2-[4-(4-fluoro-benzoyl)-piperidin-1-ylmethyl]-cyclobutylmethyl}-isobutyramide Intermediate P Trans-2-Hydroxymethyl-cyclobutanecarboxylic acid methyl ester Trans-Cyclobutan-1,2-carboxylic acid dimethylester (24.6 g, 142.9 mmol), was solved in 310 mL of methanol and sodium borohydride was added. (12.7 g, 322 mmol) in 5 portions each 40 minutes keeping the temperature at 0° C. After the last addition the mixture was stirred for 2 hours. 2M aqueous ammonium chloride (500 mL) and sulfuric acid 2M (76 mL) were added until pH 7. The aqueous phase was extracted 3 times with 150 mL of dichloromethane and the organic layers were purified with column chromatography using a mixture of dichloromethane and TBME (4+1) to obtain 15.3 g of the title compound (106 mmol, 74% yield) as a colourless liquid. MS (m/e): 167.2 (M+Na⁺)

Intermediate Q

Trans-2-Formyl-cyclobutanecarboxylic acid methyl ester

At −78° C., oxalyl Chloride (9.2 mL, 106.5 mmol) was solved in dichloromethane (250 mL) and (15.5 mL, 218 mmol) of dimethylsulfoxide in 20 mL of dichloromethane was added. After 15 minutes of stirring at −78° C., Trans-2-Hydroxymethyl-cyclobutanecarboxylic acid methyl ester (14 g, 95.17 mmol) was added in 78 mL of dichloromethane and 10 minutes later triethylamine (67 mL, 479 mmol) was added and the mixture was stirred for 2 h at −78° C. 150 mL of dichloromethane added and 200 mL of water were added and the aqueous phase was extracted with 200 mL of dichloromethane and the combined organic phases were purified with column chromatography on silica using n-heptane/AcOEt (4+1) to yield 11.1 g, (78 mmol, 82% yield) of the title compound as a colourless liquid. MS (m/e): 165.2 (M+Na⁺)

Intermediate R

Trans-2-[tert-Butoxycarbonylamino-(toluene-4-sulfonyl)-methyl]-cyclobutanecarboxylic acid methyl ester According to the synthesis of Trans-2-[tert-Butoxycarbonylamino-(toluene-4-sulfonyl)-methyl]-cyclopropanecarboxylic acid ethyl ester (intermediate K, example 43) the title compound was prepared from Trans-2-Formyl-cyclobutanecarboxylic acid methyl ester, (11.1 g, 73.4 mmol), tert-butylcarbamate (12.4 g, 105.8 mmol), sodium p-toluensulfinate in water (19.1 g, 104.6 mmol) and formic acid (24 mL, 636.1 mol) and 29.17 g, (73.4 mmol, 84.3% yield) was obtained. MS (m/e): 384.5 (M+H⁺)

Intermediate S

Trans-(2-Hydroxymethyl-cyclobutylmethyl)-carbamic acid tert-butyl ester

Step 1

Trans-2-(tert-Butoxycarbonylamino-methyl)-cyclobutanecarboxylic acid methyl ester According to the synthesis of Trans-2-(tert-Butoxycarbonylamino-methyl)-cyclopropanecarboxylic acid ethyl ester (intermediate L, example 43), the title compound was prepared from Trans-2-[tert-Butoxycarbonylamino-(toluene-4-sulfonyl)-methyl]-cyclobutanecarboxylic acid methyl ester (17.7 g, 44.53 mmol), sodium borohydride (3.3 g, 83.74 mmol) and 8.2 g, (33.7 mmol, 73.4% yield) was obtained. MS (m/e): 244.0 (M+H⁺).

Step 2

Trans-(2-Hydroxymethyl-cyclobutylmethyl)-carbamic acid tert-butyl ester

To a solution of Trans-2-(tert-Butoxycarbonylamino-methyl)-cyclobutanecarboxylic acid methyl ester (4.1 g, 16.8 mmol) in methanol (20 mL) at 0° C., sodium Borohydride (1.3 g, 33.6 mmol) was added portionwise. The mixture was stirred 4 h until TLC after TLC indicated completion of the reaction. A saturated solution of ammonium chloride was added, the methanol was removed under vacuum and the water was extracted three times with dichloromethane. The combined organic layers were washed with water and brine, dried over magnesium sulfate, filtered, evaporated and purified with column chromatography on silica gel using n-Heptane-EtOAc (1:1). The product fractions were concentrated to give 2.8 g (16.8 mmol, 80% yield) of the title compound as a white solid. MS (m/e): 216.3 (M+H⁺)

Intermediate T

Methanesulfonic acid trans-2-(tert-butoxycarbonylamino-methyl)-cyclobutylmethyl ester At 0° C. trans-(2-Hydroxymethyl-cyclobutylmethyl)-carbamic acid tert-butyl ester (1 g, 4.6 mmol), was solved in 10 mL of dichloromethane and methanosulfonylchloride (0.585 g, 4.6 mmol) was added followed by (1.19 mL, 7 mmol) of N,N-diisopropylethylamine. The mixture was stirred 1 h at 0°

C. and aqueous solution of ammonium chloride was added and the aqueous phase was extracted with 200 mL of dichloromethane and the combined organic phases were purified with column chromatography on silica using n-heptane/AcOEt (1/1) to yield 1.27 g, (4.4 mmol, 94.5% yield) of the title compound as a light yellow liquid. MS (m/e): 294.2 (M+H$^+$).

Intermediate N

Trans-2-[4-(4-Fluoro-benzoyl)-piperidin-1-ylmethyl]-cyclobutylmethyl}-carbamic acid tert-butyl ester A mixture of 4-(4-fluorobenzoyl)piperidine (0.500 g, 2.0 mmol), methanesulfonic acid trans-2-(tert-butoxycarbonylamino-methyl)-cyclobutylmethyl ester (0.662 g, 2.2 mmol), and triethylamine (0.71 mL, 5 mol) in acetonitrile (4 mL) was stirred for 12 h at 80° C. The mixture was concentrated to dryness, extracted with 10 mL dichloromethane and purified with column chromatography on silica using dichloromethane-methanol (9:1). The product fractions were concentrated to give 0.759 g (1.9 mmol, 91.5% yield) of a light brown solid. MS (m/e): 405.5 (M+H$^+$).

[1-(Trans-2-Aminomethyl-cyclobutylmethyl)-piperidin-4-yl]-(4-fluoro-phenyl)-methanone; trifluoro-acetic acid salt According to the synthesis of [1-(Trans-2-Aminomethyl-cyclopropylmethyl)-piperidin-4-yl]-(4-fluoro-phenyl)-methanone; trifluoro-acetic acid salt (from example 43), the title compound was prepared from Trans-2-[4-(4-Fluoro-benzoyl)-piperidin-1-ylmethyl]-cyclobutylmethyl}-carbamic acid tert-butyl ester and trifluoroacetic acid. MS (m/e): 291.2 (M+H$^+$).

Example 47

N-{(Trans-2-[4-(4-Fluoro-benzoyl)-piperidin-1-ylmethyl]-cyclopropylmethyl}-3-(5-methyl-[1,2,4]oxadiazol-3-yl)-benzamide According to the procedure described for the synthesis of N-{(trans-2-[4-(4-Fluoro-benzoyl)-piperidin-1-ylmethyl]-cyclopropylmethyl}-3-(5-methyl-[1,2,4]oxadiazol-3-yl)-benzamide (example 43), the title compound was prepared from [1-(trans-2-Aminomethyl-cyclobutylmethyl)-piperidin-4-yl]-(4-fluoro-phenyl)-methanone; trifluoro-acetic acid salt and 3-(5-methyl-[1,2,4]oxadiazol-3-yl)-benzoic acid. (m/e): 491.2 (M+H$^+$).

Further amide derivates were synthesized from [1-(trans-2-Aminomethyl-cyclobutylmethyl)-piperidin-4-yl]-(4-fluoro-phenyl)-methanone; trifluoro-acetic acid salt, 2-(1H-benzotriazol-1-yl)-1,1,3,3-tetramethyl uronium tetrafluoroborate, N-ethyldiisopropylamine and the respective commercially available acid listed in table C. The purification was performed with preparative HPLC on reversed phase column material eluting with a gradient formed from acetonitrile/water (0.05% Et$_3$N). The evaporation of the product fractions yielded the respective amides which comprise examples 47 to example 48.

| Ex. No | Systematic name | MW | Starting materials | MW found (M + H)$^+$ |
|---|---|---|---|---|
| 47 | N-{Trans-2-[4-(4-Fluoro-benzoyl)-piperidin-1-ylmethyl]-cyclobutylmethyl}-3-(5-methyl-[1,2,4]oxadiazol-3-yl)-benzamide | 490.5 | [1-(trans-2-Aminomethyl-cyclobutylmethyl)-piperidin-4-yl]-(4-fluoro-phenyl)-methanone; trifluoro-acetic acid salt and 3-(5-methyl-[1,2,4]oxadiazol-3-yl)-benzoic acid | 491.2 |
| 48 | 2-(4-Chloro-phenyl)-N-{Trans-2-[4-(4-fluoro-benzoyl)-piperidin-1-ylmethyl]-cyclobutylmethyl}-isobutyramide | 485.04 | [1-(trans-2-Aminomethyl-cyclobutylmethyl)-piperidin-4-yl]-(4-fluoro-phenyl)-methanone; trifluoro-acetic acid salt and 4-chloro-alpha,alpha-dimethylphenyl acetic acid | 485.4 |

Example 49

1-(4-Chloro-phenyl)-3-{trans-2-[4-(4-fluoro-benzoyl)-piperidin-1-ylmethyl]-cyclobutylmethyl}-urea The title compound was synthesized from 1-(Trans-2-Aminomethyl-cyclobutylmethyl)-piperidin-4-yl]-(4-fluoro-phenyl)-methanone; trifluoro-acetic acid salt and 4-chlorophenyl isocyanate in acetonitrile according to the procedure described for example 38. MS (m/e): 458.1 (M+H$^+$)

| Ex. No | Systematic name | MW | Starting materials | MW found (M + H)+ |
|---|---|---|---|---|
| 49 | 1-(4-Chloro-phenyl)-3-{trans-2-[4-(4-fluoro-benzoyl)-piperidin-1-ylmethyl]-cyclobutylmethyl}-urea | 457.9 | 1-(Trans-2-Aminomethyl-cyclobutylmethyl)-piperidin-4-yl]-(4-fluoro-phenyl)-methanone; trifluoro-acetic acid salt and 4-Chlorophenyl isocyanate | 458.1 |

Example 50

N-trans-(4-{2-[4-Fluoro-4-(4-fluoro-benzoyl)-piperidin-1-yl]-ethyl}-cyclohexyl)-3-methoxy-propionamide Intermediate AA 4-(4-Fluoro-benzoyl)-piperidine-1-carboxylic acid tert-butyl ester 4-(4-fluorobenzoyl)piperidine hydrochloride (1.5 g, 6.16 mmol) was suspended in acetonitrile (30 mL) and triethylamine (0.940 mL, 6.8 mmol), dimethylaminopyridine (0.150 g, 1.2 mmol) and Di-tert.-butyl-dicarbonate (1.6 g, 7.4 mmol) were added at 0° C. and the mixture was stirred at room temperature for 3 h. The solvent was evaporated and aqueous 1M HCl is added (20 mL) and the water was extracted with ethyl acetate (100 mL). and purified with column chromatography on silica using n-heptane-EtOAc (1:1). The product fractions were concentrated to give 1.87 g (6.08 mmol, 99% yield) of a white solid. MS (m/e): 307.3 (M+H$^+$).

Intermediate AB

4-Fluoro-4-(4-fluoro-benzoyl)-piperidine-1-carboxylic acid tert-butyl ester 4-(4-Fluoro-benzoyl)-piperidine-1-carboxylic acid tert-butyl ester in 0.5 mL of DMF was added to a solution at 0° C. containing 0.5 mL of tBuOH, (0.109 mg, 0.651 mmol) tBuOK and 2 mL of DMF. After 20 min stirring at 0° C., N-Fluorobenzenesulfonimide (0.246 g, 0.781 mmol) was added portionwise. The reaction was stirred at 0° C. during 45 min. and (0.55 g, 0.33 mmol) of tBuOK were added at 0° C. and 10 min later (0.123 g, 0.390 mmol) of N-Fluorobenzenesulfonimide. Each 0.5 h two more additions of (0.55 g, 0.33 mmol) tBuOK and (0.123 g, 0.390 mmol) N-Fluorobenzenesulfonimide were repited. 1 h later of the last addition the reaction was quenched with 4 mL of water and the DMF was removed under vacuum. The water was extracted with ethyl acetate and the combined organic phases were purified with column chromatography on silica using n-heptane-EtOAc (3:1). The product fractions were concentrated to give 0.122 g (0.375 mmol, 58% yield) of a yellow oil. MS (m/e): 326.1 (M+H$^+$).

Intermediate D

4-Fluoro-4-(4-fluoro-benzoyl)-piperidine

4-Fluoro-4-(4-fluoro-benzoyl)-piperidine-1-carboxylic acid tert-butyl ester (0.122 g, 0.375 mmol) was solved in dichloromethane (2 mL) and trifluoroacetic acid (0.258 mL, 3.37 mmol) was added at 0° C. Aqueous NaHCO$_3$ is slowly added until pH 9 and the mixture extracted with 3 times with dichloromethane and ethyl acetate. The solvent was evaporated to yield g (0. mmol, 100%) of a white solid that was used without purification on the next steps. MS (m/e): 226.1 (M+H$^+$).

Intermediate E

Trans-4-{2-[4-Fluoro-4-(4-fluoro-benzoyl)-piperidin-1-yl]-ethyl}-cyclohexyl)-carbamic acid tert-butyl ester The title compound was prepared from 4-Fluoro-4-(4-fluoro-benzoyl)-piperidine and Trans-[4-(2-Oxo-ethyl)-cyclohexyl]-carbamic acid tert-butyl ester according to the procedure described for the synthesis of Trans-(4-{2-[4-(4-Fluoro-benzoyl)-piperidin-1-yl]-ethyl}-cyclohexyl)-carbamic acid tert-butyl ester (intermediate E, example 1) in 1,2 dichloroethane using triacetoxyborohydride. MS (m/e): 451.1 (M+H$^+$).

Intermediate F

Trans-{1-[2-(4-Amino-cyclohexyl)-ethyl]-4-fluoro-piperidin-4-yl}-(4-fluoro-phenyl)-methanone; trifluoro-acetic acid salt The title compound was prepared from Trans-4(4-{2-[4-Fluoro-4-(4-fluoro-benzoyl)-piperidin-1-yl]-ethyl}-cyclohexyl)-carbamic acid tert-butyl ester and trifluoroacetic acid according to the procedure described for the synthesis of trans-{1-[2-(4-Amino-cyclohexyl)-ethyl]-piperidin-4-yl}-(4-fluoro-phenyl)-methanone; trifluorocetic acid salt (intermediate F, example 1). MS (m/e): 351.3 (M+H$^+$).

N-trans-(4-{2-[4-Fluoro-4-(4-fluoro-benzoyl)-piperidin-1-yl]-ethyl}-cyclohexyl)-3-methoxy-propionamide According to the procedure described for the synthesis of 4-Chloro-N-trans (4-{2-[4-(4 fluoro-benzoyl)-piperidin-1-yl]-ethyl}-cyclohexyl)-benzamide (example 1) the title compound was synthesized from Trans-{1-[2-(4-Amino-cyclohexyl)-ethyl]-4-fluoro-piperidin-4-yl}-(4-fluoro-phenyl)-methanone; trifluoro-acetic acid salt, 2-(1H-benzotriazol-1-yl)-1,1,3,3-tetramethyl uronium tetrafluoroborate, N-ethyldiisopropylamine and 3-methoxy-propionic acid. MS (m/e): 437.0 (M+H$^+$).

Further amide derivates were synthesized from Trans-{1-[2-(4-Amino-cyclohexyl)-ethyl]-4-fluoro-piperidin-4-yl}-(4-fluoro-phenyl)-methanone; trifluoro-acetic acid salt, 2-(1H-benzotriazol-1-yl)-1,1,3,3-tetramethyl uronium tetrafluoroborate, N-ethyldiisopropylamine and the respective commercially available acid listed in table D. The purification was performed with preparative HPLC on reversed phase column material eluting with a gradient formed from acetonitrile/water (0.05% Et$_3$N). The evaporation of the product fractions yielded the respective amides which comprise example 50 to example 53.

| Ex. No | Systematic name | MW | Starting materials | MW found (M + H)+ |
|---|---|---|---|---|
| 50 | N-trans (4-{2-[4-Fluoro-4-(4-fluoro-benzoyl)-piperidin-1-yl]-ethyl}-cyclohexyl)-3-methoxy-propionamide | 436.5 | Trans-{1-[2-(4-Amino-cyclohexyl)-ethyl]-4-fluoro-piperidin-4-yl}-(4-fluoro-phenyl)-methanone; trifluoro-acetic acid salt and 3-methoxy-propionic acid | 437.0 |
| 51 | 4-Ethoxy-N-trans (4-{2-[4-fluoro-4-(4-fluoro-benzoyl)-piperidin-1-yl]-ethyl}-cyclohexyl)-benzamide | 498.6 | Trans-{1-[2-(4-Amino-cyclohexyl)-ethyl]-4-fluoro-piperidin-4-yl}-(4-fluoro-phenyl)-methanone; trifluoro-acetic acid salt and 4-Ethoxybenzoic acid | 499.0 |
| 52 | Tetrahydro-furan-3-carboxylic acid trans-(4-{2-[4-fluoro-4-(4-fluoro-benzoyl)-piperidin-1-yl]-ethyl}-cyclohexyl)-amide | 448.5 | Trans-{1-[2-(4-Amino-cyclohexyl)-ethyl]-4-fluoro-piperidin-4-yl}-(4-fluoro-phenyl)-methanone; trifluoro-acetic acid salt and Tetrahydro-furan-3-carboxylic acid | 449.0 |

-continued

| Ex. No | Systematic name | MW | Starting materials | MW found (M + H)+ |
|---|---|---|---|---|
| 53 | N-trans (4-{2-[4-Fluoro-4-(4-fluoro-benzoyl)-piperidin-1-yl]-ethyl}-cyclohexyl)-acetamide | 392.4 | Trans-{1-[2-(4-Amino-cyclohexyl)-ethyl]-4-fluoro-piperidin-4-yl}-(4-fluoro-phenyl)-methanone; trifluoro-acetic acid salt and acetic acid | 393.2 |

Example 54

1-(4-Chloro-phenyl)-3-(4-{2-[4-fluoro-4-(4-fluoro-benzoyl)-piperidin-1-yl]-ethyl}-cyclohexyl)-urea The title compound was synthesized from Trans-{1-[2-(4-Amino-cyclohexyl)-ethyl]-4-fluoro-piperidin-4-yl}-(4-fluoro-phenyl)-methanone; trifluoro-acetic acid salt 4-chlorophenyl isocyanate in acetonitrile according to the procedure described for example 38. MS (m/e): 504.3 (M+).

According to the procedure described for the synthesis of example 54, further urea derivates were synthesized from {1-[2-(4-Amino-cyclohexyl)-ethyl]-4-fluoro-piperidin-4-yl}-(4-fluoro-phenyl)-methanone; trifluoro-acetic acid salt and the respective commercially available isocyanate. The purification was performed with preparative HPLC on reversed phase column material eluting with a gradient formed from acetonitrile/water (0.05% Et$_3$N). The evaporation of the product fractions yielded the respective ureas which comprise examples 54 and example 55.

| Ex. No | Systematic name | MW | Starting materials | MW found (M + H)+ |
|---|---|---|---|---|
| 54 | 1-(4-Chloro-phenyl)-3-trans (4-{2-[4-fluoro-4-(4-fluoro-benzoyl)-piperidin-1-yl]-ethyl}-cyclohexyl)-urea | 504.0 | {1-[2-(4-Amino-cyclohexyl)-ethyl]-4-fluoro-piperidin-4-yl}-(4-fluoro-phenyl)-methanone; trifluoro-acetic acid salt and 4-chlorophenyl isocyanate | 504.3 |
| 55 | 1-(4-Ethoxy-phenyl)-3-trans (4-{2-[4-fluoro-4-(4-fluoro-benzoyl)-piperidin-1-yl]-ethyl}-cyclohexyl)-urea | 513.6 | {1-[2-(4-Amino-cyclohexyl)-ethyl]-4-fluoro-piperidin-4-yl}-(4-fluoro-phenyl)-methanone; trifluoro-acetic acid salt and 4-Ethoxyphenyl isocyanate | 514.5 |

Example 56

Quinoline-4-carboxylic acid (4-{2-[4-(4-fluoro-benzoyl)-4-hydroxy-piperidin-1-yl]-ethyl}-cyclohexyl)-amide Intermediate W (1-Benzyl-piperidin-4-yl)-(4-fluoro-phenyl)-methanone (3 g, 12.3 mmol) of 4-(4-fluorobenzoyl)piperidine hydrochloride was suspended in acetonitrile (60 mL) and triethylamine (4.29 mL, 31 mmol), benzylbromide (1.61 mL, 14 mmol) and sodium iodide (2.8 g, 18 mol) were added. The mixture was stirred at 80° C. overnight and after cooling the mixture was filtrated, water was added and the aqueous phase was extracted with 100 mL of dichloromethane. The combined organic phases were dried with magnesium sulfate, filtrated concentrated and purified with column chromatography on silica using dichloromethane/Methanol (95/0.5) to yield 3.6 g, (12 mmol, 99% yield) of the title compound as a brown solid. MS (m/e): 298.4 (M+H+).

Intermediate X (1-Benzyl-4-bromo-piperidin-4-yl)-(4-fluoro-phenyl)-methanone (Benzyl-piperidin-4-yl)-(4-fluoro-phenyl)-methanone (2 g, 6.73 mmol) is solved in 500 mL of chloroform, bromo is added (2.14 g, 13.4 mmol) and the mixture is refluxed for 1 h and let to stir overnight. When it is cool the mixture is filtrated to obtain 1.4 g of the title compound as a white solid (3.83 mol, 3.8 mmol). MS (m/e): 376.1 (M+).

Intermediate Y

6-Benzyl-2-(4-fluoro-phenyl)-2-methoxy-1-oxa-6-aza-spiro[2.5]octane

Benzyl-4-bromo-piperidin-4-yl)-(4-fluoro-phenyl)-methanone (1 g, 2.66 mmol) is solved in methanol (11 mL), sodium (0.300 g, 13.04 mmol) was added and the mixture was refluxed for 2 h. Water was added, the methanol was concentrated under vacuum and the aqueous phase was extracted with ethyl acetate (50 mL). The combined organic phases were dried with magnesium sulfate, filtrated and concentrated to yield 0.644 g, (2 mmol, 75% yield) of the title compound as a yellow oil that was used without purification on the next step. MS (m/e): 328.4 (M+H+).

Intermediate Z (1-Benzyl-4-hydroxy-piperidin-4-yl)-(4-fluoro-phenyl)-methanone

6-Benzyl-2-(4-fluoro-phenyl)-2-methoxy-1-oxa-6-aza-spiro[2.5]octane (0.600 g, 1.83 mmol) was solved in ether (6 mL), 0.6 mL of aqueous HCl was added (37%) and the reaction mixture was stirred at room temperature. After 0.5 h the reaction was finished and water was added and the product precipitate. The mixture was filtrated and the solid was recrystallized ethanol/ether to yield the title compound as a white solid (0.550 g, 1.76 mmol, 96%). MS (m/e): 314.0 (M+H+).

Intermediate D (4-Fluoro-phenyl)-(4-hydroxy-piperidin-4-yl)-methanone (0.550 g, 1.76 mmol) of (1-Benzyl-4-hydroxy-piperidin-4-yl)-(4-fluoro-phenyl)-methanone was hydrogenated in 4 mL of ethyl acetate and 2 mL of methanol using 0.065 g, (0.61 mmol) of Palladium on charcoal. to yield 0.392 g of the title compound (1.76 mmol, 100% yield) as a off-white solid after filtration of the catalyst and removal of the solvent under vacuum. MS (m/e): 314.0 (M+H$^+$).

Intermediate E (4-{2-[4-(4-Fluoro-benzoyl)-4-hydroxy-piperidin-1-yl]-ethyl}-cyclohexyl)-carbamic acid tert-butyl ester The title compound was prepared from ((4-Fluoro-phenyl)-(4-hydroxy-piperidin-4-yl)-methanone and trans-[4-(2-Oxo-ethyl)-cyclohexyl]-carbamic acid tert-butyl ester according to the procedure described for the synthesis of (4-{2-Trans-[4-(4-Fluoro-benzoyl)-piperidin-1-yl]-ethyl}-cyclohexyl)-carbamic acid tert-butyl ester (intermediate E, example 1) in 1,2 dichloroethane using triacetoxyborohydride. MS (m/e): 451.1 (M+H$^+$).

Intermediate F

Trans-{1-[2-(4-Amino-cyclohexyl)-ethyl]-4-hydroxy-piperidin-4-yl}-(4-fluoro-phenyl)-methanone; trifluoro-acetic acid salt The title compound was prepared from (4-{2-[4-(4-Fluoro-benzoyl)-4-hydroxy-piperidin-1-yl]-ethyl}-cyclohexyl)-carbamic acid tert-butyl ester and trifluoroacetic acid according to the procedure described for the synthesis of trans-{1-[2-(4-Amino-cyclohexyl)-ethyl]-piperidin-4-yl}-(4-fluoro-phenyl)-methanone; trifluorocetic acid salt (intermediate F, example 1). MS (m/e): 351.3 (M+H$^+$).

Quinoline-4-carboxylic acid trans-(4-{2-[4-(4-fluoro-benzoyl)-4-hydroxy-piperidin-1-yl]-ethyl}-cyclohexyl)-amide According to the procedure described for the synthesis of N-Trans-Chloro-N-(4-{2-[4-(4-fluoro-benzoyl)-piperidin-1-yl]-ethyl}-cyclohexyl)-benzamide (example 1) the title compound was synthesized from Trans-{1-[2-(4-Amino-cyclohexyl)-ethyl]-4-hydroxy-piperidin-4-yl}-(4-fluoro-phenyl)-methanone; trifluoro-acetic acid salt and Quinoline-4-carboxylic acid using 2-(1H-benzotriazol-1-yl)-1,1,3,3-tetramethyl uronium tetrafluoroborate, N-ethyldiisopropylamine in DMF. MS (m/e): 504.2 (M+H$^+$).

Further amide derivates were synthesized from {1-[2-(4-Amino-cyclohexyl)-ethyl]-4-hydroxy-piperidin-4-yl}-(4-fluoro-phenyl)-methanone; trifluoro-acetic acid salt and the respective commercially available acid. The purification was performed with preparative HPLC on reversed phase column material eluting with a gradient formed from acetonitrile/water (0.05% Et$_3$N). The evaporation of the product fractions yielded the respective amides which comprise examples 56 to example 57.

| Ex. No | Systematic name | MW | Starting materials | MW found (M + H)+ |
|---|---|---|---|---|
| 56 | Quinoline-4-carboxylic acid trans (4-{2-[4-(4-fluoro-benzoyl)-4-hydroxy-piperidin-1-yl]-ethyl}-cyclohexyl)-amide | 503.6 | Trans-{1-[2-(4-Amino-cyclohexyl)-ethyl]-4-hydroxy-piperidin-4-yl}-(4-fluoro-phenyl)-methanone; trifluoro-acetic acid salt and Quinoline-4-carboxylic acid | 504.2 |
| 57 | N-trans (4-{2-[4-(4-Fluoro-benzoyl)-4-hydroxy-piperidin-1-yl]-ethyl}-cyclohexyl)-3-(5-methyl-[1,2,4]oxadiazol-3-yl)-benzamide | 534.6 | Trans-{1-[2-(4-Amino-cyclohexyl)-ethyl]-4-hydroxy-piperidin-4-yl}-(4-fluoro-phenyl)-methanone; trifluoro-acetic acid salt and 3-(5-methyl-[1,2,4]oxadiazol-3-yl)-benzoic acid | 535.2 |

Example 57A1

Trans N-(4-{2-[4-(4-Fluoro-benzoyl)-4-methyl-piperidin-1-yl]-ethyl}-cyclohexyl)-acetamide Intermediate D (4-Fluoro-phenyl)-(4-methyl-piperidin-4-yl)-methanone Step 1

N-boc-4-methyl-4-piperidinecarboxylic acid (4 g, 16 mol), 4-Fluorobenzeneboronic acid (2.7 g, 20 mol), Pivalic anhydride (4.6 g, 25 mmol), Pd(OAc)$_2$(0.111 g, 0.4 mol), 1,1'-Bis(diphenylphosphino)ferrocene (0.319 g, 0.1 mol) and (0.7 mL, 41 mmol) of water are mixed together in 20 mL of tetrahydrofuran and the mixture heated at 60° C. overnight. The reaction mixture was filtrated and the solvent was removed under vacuum. The residue was purified with column chromatography on silica using n-heptane-EtOAc (4:1) to yield 0.216 g (5%) of the title compound. MS (m/e): 322.0 (M+H$^+$).

(4-Fluoro-phenyl)-(4-methyl-piperidin-4-yl)-methanone; compound with trifluoro-acetic acid The title compound was synthesized from (4-Fluoro-phenyl)-(4-methyl-piperidin-4-yl)-methanone (0.215 g, 0.6 mmol) and trifluoroacetic acid (1.4 mL, 6 mmol) in 5 mL of dichloromethane to yield 0.328 g of a yellow solid that was used on the next step without purification. MS (m/e): 222.3 (M+H$^+$).

Step 2

(4-Fluoro-phenyl)-(4-methyl-piperidin-4-yl]-methanone

Intermediate E

Trans (4-{2-[4-(4-Fluoro-benzoyl)-4-methyl-piperidin-1-yl]-ethyl}-cyclohexyl)-carbamic acid tert-butyl ester According to the procedure described for the synthesis of Trans-(4-{2-[4-(4 Fluoro-benzoyl)-piperidin-1-yl]-ethyl}-cyclohexyl)-carbamic acid tert-butyl ester (intermediate E, example 1), the title compound was synthesized from (4-Fluoro-phenyl)-(4-methyl-piperidin-4-yl)-methanone and Trans-[4-(2-Oxo-ethyl)-cyclohexyl]-carbamic acid tert-butyl ester. MS (m/e): 447.4 (M+H$^+$).

Intermediate F

{1-trans-[2-(4-Amino-cyclohexyl)-ethyl]-4-methyl-piperidin-4-yl}-(4-fluoro-phenyl)-methanone According to the procedure described for the synthesis of {1-trans-[2-(4-Amino-cyclohexyl)-ethyl]-piperidin-4-yl}-(4-fluoro-phenyl)-methanone, trifluoroacetic acid salt (intermediate F, example 1), the title compound was synthesized from Trans (4-{2-[4-(4-Fluoro-benzoyl)-4-methyl-piperidin-1-yl]-ethyl}-cyclohexyl)-carbamic acid tert-butyl ester and trifluoroacetic acid. MS (m/e): 347.4 (M+H$^+$).

Trans N-(4-{2-[4-(4-Fluoro-benzoyl)-4-methyl-piperidin-1-yl]-ethyl}-cyclohexyl)-acetamide According to the procedure described for the synthesis of example 36 the title compound was synthesized from the {1-trans-[2-(4-Amino-cyclohexyl)-ethyl]-4-methyl-piperidin-4-yl}-(4-fluoro-phenyl)-methanone and the corresponding acetyl chloride. MS (m/e): 389.4 (M+H$^+$).

Example 58

N-Trans-(4-{2-[4-(2,4-Difluoro-benzoyl)-piperidin-1-yl]-ethyl}-cyclohexyl)-3-methoxy-propionamide Intermediate E

Trans-(4-{2-[4-(2,4-Fluoro-benzoyl)-piperidin-1-yl]-ethyl}-cyclohexyl)-carbamic acid tert-butyl ester According to the procedure described for the synthesis of Trans-(4-{2-[4-(4 Fluoro-benzoyl)-piperidin-1-yl]-ethyl}-cyclohexyl)-carbamic acid tert-butyl ester (intermediate E, example 1), the title compound was synthesized from 4-(2,4-fluorobenzoyl)piperidine and Trans-[4-(2-Oxo-ethyl)-cyclohexyl]-carbamic acid tert-butyl ester. MS (m/e): 451.5 (M+H$^+$).

Intermediate F

{1-trans-[2-(4-Amino-cyclohexyl)-ethyl]-piperidin-4-yl}-(2,4-difluoro-phenyl)-methanone; compound with trifluoro-acetic acid According to the procedure described for the synthesis of {1-trans-[2-(4-Amino-cyclohexyl)-ethyl]-piperidin-4-yl}-(4-fluoro-phenyl)-methanone, trifluoroacetic acid salt (intermediate F, example 1), the title compound was synthesized from Trans-(4-{2-[4-(2,4-Fluoro-benzoyl)-piperidin-1-yl]-ethyl}-cyclohexyl)-carbamic acid tert-butyl ester and trifluoroacetic acid. MS (m/e): 351.5 (M+H$^+$).

N-trans-(4-{2-[4-(2,4-Difluoro-benzoyl)-piperidin-1-yl]-ethyl}-cyclohexyl)-3-methoxy-propionamide According to the procedure described for the synthesis of {4-Chloro-N-trans (4-{2-[4-(4 fluoro-benzoyl)-piperidin-1-yl]-ethyl}-cyclohexyl)-benzamide (example 1) the title compound was synthesized from Trans-{1-[2-(4-Amino-cyclohexyl)-ethyl]-piperidin-4-yl}-(2,4-difluoro-phenyl)-methanone (example 58, intermediate F) and 3-methoxy-propionic acid using 2-(1H-benzotriazol-1-yl)-1,1,3,3-tetramethyl uronium tetrafluoroborate and N-ethyldiisopropylamine in DMF. MS (m/e): 437.0 (M+H$^+$).

According to the procedure described for the synthesis of example 58 further derivatives have been synthesized from Trans-{1-[2-(4-Amino-cyclohexyl)-ethyl]-piperidin-4-yl}-(2,4-difluoro-phenyl)-methanone (example 58, intermediate F) and the corresponding acid. The purification was performed with preparative HPLC on reversed phase column material eluting with a gradient formed from acetonitrile/water (0.05% Et$_3$N). The evaporation of the product fractions yielded the respective amides which comprise examples 58 to example 63A18.

| Ex. No | Systematic name | MW | Starting materials | MW found (M+H)+ |
|---|---|---|---|---|
| 58 | N-trans (4-{2-[4-(2,4-Difluoro-benzoyl)-piperidin-1-yl]-ethyl}-cyclohexyl)-3-methoxy-propionamide | 436.5 | Trans-{1-[2-(4-Amino-cyclohexyl)-ethyl]-piperidin-4-yl}-(2,4-difluoro-phenyl)-methanone and 3-methoxy-propionic acid | 437.0 |
| 59 | N-trans (4-{2-[4-(2,4-Difluoro-benzoyl)-piperidin-1-yl]-ethyl}-cyclohexyl)-4-ethoxy-benzamide | 498.6 | Trans-{1-[2-(4-Amino-cyclohexyl)-ethyl]-piperidin-4-yl}-(2,4-difluoro-phenyl)-methanone and 4-ethoxy-benzoic acid | 499.2 |
| 60 | N-trans (4-{2-[4-(2,4-Difluoro-benzoyl)-piperidin-1-yl]-ethyl}-cyclohexyl)-3-(5-methyl-[1,2,4]oxadiazol-3-yl)-benzamide | 536.6 | Trans-{1-[2-(4-Amino-cyclohexyl)-ethyl]-piperidin-4-yl}-(2,4-difluoro-phenyl)-methanone and 3-(5-methyl-[1,2,4]oxadiazol-3-yl)-benzoic acid | 537.3 |
| 61 | Tetrahydro-furan-3-carboxylic acid trans (4-{2-[4-(2,4-difluoro-benzoyl)-piperidin-1-yl]-ethyl}-cyclohexyl)-amide | 448.5 | Trans-{1-[2-(4-Amino-cyclohexyl)-ethyl]-piperidin-4-yl}-(2,4-difluoro-phenyl)-methanone and Tetrahydro-furan-3-carboxylic acid | 449.0 |

| Ex. No | Systematic name | MW | Starting materials | MW found (M + H)+ |
|---|---|---|---|---|
| 62 | N-trans (4-{2-[4-(2,4-Difluoro-benzoyl)-piperidin-1-yl]-ethyl}-cyclohexyl)-acetamide | 392.4 | Trans-{1-[2-(4-Amino-cyclohexyl)-ethyl]-piperidin-4-yl}-(2,4-difluoro-phenyl)-methanone and acetic acid | 393.4 |
| 63 | Tetrahydro-pyran-4-carboxylic acid trans (4-{2-[4-(2,4-difluoro-benzoyl)-piperidin-1-yl]-ethyl}-cyclohexyl)-amide | 462.5 | Trans-{1-[2-(4-Amino-cyclohexyl)-ethyl]-piperidin-4-yl}-(2,4-difluoro-phenyl)-methanone and Tetrahydro-pyran-4-carboxylic acid | 463.4 |
| 63A1 | N trans-(4-{2-[4-(2,4-Difluoro-benzoyl)-piperidin-1-yl]-ethyl}-cyclohexyl)-propionamide | 406.5 | Trans-{1-[2-(4-Amino-cyclohexyl)-ethyl]-piperidin-4-yl}-(2,4-difluoro-phenyl)-methanone and propionic acid | 407.3 |
| 63A2 | 4-Chloro-N-(4-{2-[4-(2,4-difluoro-benzoyl)-piperidin-1-yl]-ethyl}-cyclohexyl)-benzamide | 406.5 | Trans-{1-[2-(4-Amino-cyclohexyl)-ethyl]-piperidin-4-yl}-(2,4-difluoro-phenyl)-methanone and propionic acid and 4-Chloro benzoic acid | 407.3 |
| 63A3 | Cyclopropanecarboxylic acid (4-{2-[4-(2,4-difluoro-benzoyl)-piperidin-1-yl]-ethyl}-cyclohexyl)-amide | 418.5 | Trans-{1-[2-(4-Amino-cyclohexyl)-ethyl]-piperidin-4-yl}-(2,4-difluoro-phenyl)-methanone and propionic acid and Cyclopropanecarboxylic acid | 419.4 |
| 63A4 | Cyclobutanecarboxylic acid (4-{2-[4-(2,4-difluoro-benzoyl)-piperidin-1-yl]-ethyl}-cyclohexyl)-amide | 432.5 | Trans-{1-[2-(4-Amino-cyclohexyl)-ethyl]-piperidin-4-yl}-(2,4-difluoro-phenyl)-methanone and propionic acid and Cyclobutanecarboxylic acid | 433.3 |
| 63A5 | 5-Methanesulfonyl-thiophene-2-carboxylic acid (4-{2-[4-(2,4-difluoro-benzoyl)-piperidin-1-yl]-ethyl}-cyclohexyl)-amide | 538.6 | Trans-{1-[2-(4-Amino-cyclohexyl)-ethyl]-piperidin-4-yl}-(2,4-difluoro-phenyl)-methanone and propionic acid and 5-Methanesulfonyl-thiophene-2-carboxylic acid | 538.5 |
| 63A6 63A7 63A8 | Chroman-3-carboxylic acid (4-{2-[4-(2,4-difluoro-benzoyl)-piperidin-1-yl]-ethyl}-cyclohexyl)-amide | 510.6 | Trans-{1-[2-(4-Amino-cyclohexyl)-ethyl]-piperidin-4-yl}-(2,4-difluoro-phenyl)-methanone and propionic acid and Chroman-3-carboxylic acid (note: Chiral separation yields both enantiomers) | 511.5 |
| 63A9 | Biphenyl-4-carboxylic acid (4-{2-[4-(2,4-difluoro-benzoyl)-piperidin-1-yl]-ethyl}-cyclohexyl)-amide | 530.7 | {1-[2-(4-amino-cyclohexyl)-ethyl]-piperidin-4-yl}-(2,4-difluoro-phenyl)-methanone and biphenyl-4-carboxylic acid | 530.9 |
| 63A10 | N-trans (4-{2-[4-(2,4-Difluoro-benzoyl)-piperidin-1-yl]-ethyl}-cyclohexyl)-6-morpholin-4-yl-nicotinamide | 540.6 | Trans {1-[2-(4-amino-cyclohexyl)-ethyl]-piperidin-4-yl}-(2,4-difluoro-phenyl)-methanone 2-morpholino nicotinic acid | 541.0 |
| 63A11 | N-trans (4-{2-[4-(2,4-Difluoro-benzoyl)-piperidin-1-yl]-ethyl}-cyclohexyl)-2-(3-methyl-isoxazol-5-yl)-acetamide | 473.5 | Trans {1-[2-(4-amino-cyclohexyl)-ethyl]-piperidin-4-yl}-(2,4-difluoro-phenyl)-methanone and 3-methyl 5-isoxazoleacetic acid | 474.6 |
| 63A12 | 4-Trifluoromethyl-cyclohexanecarboxylic acid trans (4-{2-[4-(2,4-difluoro-benzoyl)-piperidin-1-yl]-ethyl}-cyclohexyl)-amide | 528.6 | Trans {1-[2-(4-amino-cyclohexyl)-ethyl]-piperidin-4-yl}-(2,4-difluoro-phenyl)-methanone and 4-Trifluoromethyl-cyclohexanecarboxylic acid | 529.2 |
| 63A13 | N-(4-{2-[4-(2,4-Difluoro-benzoyl)-piperidin-1-yl]-ethyl}-cyclohexyl)-4-morpholin-4-yl-benzamide | 539.6 | Trans {1-[2-(4-amino-cyclohexyl)-ethyl]-piperidin-4-yl}-(2,4-difluoro-phenyl)-methanone and 4-morpholino benzoic acid | 540.3 |
| 63A14 | N-(4-{2-[4-(2,4-Difluoro-benzoyl)-piperidin-1-yl]-ethyl}-cyclohexyl)-2-hydroxy-acetamide | 408.4 | Trans {1-[2-(4-amino-cyclohexyl)-ethyl]-piperidin-4-yl}-(2,4-difluoro-phenyl)-methanone and 2-hydroxy-acetic acid | 409.4 |
| 63A15 | (R)—N-Trans (4-{2-[4-(2,4-Difluoro-benzoyl)-piperidin-1-yl]-ethyl}-cyclohexyl)-2-methoxy-propionamide | 436.5 | Trans {1-[2-(4-amino-cyclohexyl)-ethyl]-piperidin-4-yl}-(2,4-difluoro-phenyl)-methanone and 2-methoxy-propionamide | 437.4 |

-continued

| Ex. No | Systematic name | MW | Starting materials | MW found (M + H)+ |
|---|---|---|---|---|
| 63A16 | 2-Benzyloxy-N-trans (4-{2-[4-(2,4-difluoro-benzoyl)-piperidin-1-yl]-ethyl}-cyclohexyl)-acetamide | 498.6 | Trans {1-[2-(4-amino-cyclohexyl)-ethyl]-piperidin-4-yl}-(2,4-difluoro-phenyl)-methanone and 2-Benzyloxy acetic acid | 499.3 |
| 63A17 | (S)-Tetrahydro-furan-3-carboxylic acid (4-{2-[4-(2,4-difluoro-benzoyl)-piperidin-1-yl]-ethyl}-cyclohexyl)-amide | 448.5 | Trans {1-[2-(4-amino-cyclohexyl)-ethyl]-piperidin-4-yl}-(2,4-difluoro-phenyl)-methanone and (S)-Tetrahydro-furan-3-carboxylic acid | 449.4 |
| 63A18 | (R)-Tetrahydro-furan-3-carboxylic acid (4-{2-[4-(2,4-difluoro-benzoyl)-piperidin-1-yl]-ethyl}-cyclohexyl)-amide | 448.5 | Trans {1-[2-(4-amino-cyclohexyl)-ethyl]-piperidin-4-yl}-(2,4-difluoro-phenyl)-methanone and (R)-Tetrahydro-furan-3-carboxylic acid | 449.3 |

Example 64

Trans-1-(4-Chloro-phenyl)-3-(4-{2-[4-(2,4-difluoro-benzoyl)-piperidin-1-yl]-ethyl}-cyclohexyl)-urea The title compound was synthesized from Trans-{1-[2-(4-Amino-cyclohexyl)-ethyl]-piperidin-4-yl}-(2,4-difluoro-phenyl)-methanone (example 58, intermediate F) and 4-Chloro phenyl isocyanate in acetonitrile according to the procedure described for example 38. MS (m/e): 504.3 (M+H$^+$).

According to the procedure described for the synthesis of example 64, further urea derivates were synthesized from Trans-{1-[2-(4-Amino-cyclohexyl)-ethyl]-piperidin-4-yl}-(2,4-difluoro-phenyl)-methanone (example 58, intermediate F) and the respective commercially available isocyanate. The purification was performed with preparative HPLC on reversed phase column material eluting with a gradient formed from acetonitrile/water (0.05% Et$_3$N). The evaporation of the product fractions yielded the respective ureas which comprise examples 64 and example 65.

| Ex. No | Systematic name | MW | Starting materials | MW found (M + H)+ |
|---|---|---|---|---|
| 64 | 1-(4-Chloro-phenyl)-3-trans (4-{2-[4-(2,4-difluoro-benzoyl)-piperidin-1-yl]-ethyl}-cyclohexyl)-urea | 504.02 | Trans-{1-[2-(4-Amino-cyclohexyl)-ethyl]-piperidin-4-yl}-(2,4-difluoro-phenyl)-methanone and 4-Chloro phenyl isocyanate | 504.3 |
| 65 | 1-(4-{2-[4-(2,4-Difluoro-benzoyl)-piperidin-1-yl] trans-ethyl}-cyclohexyl)-3-(4-ethoxy-phenyl)-urea | 513.6 | Trans-{1-[2-(4-Amino-cyclohexyl)-ethyl]-piperidin-4-yl}-(2,4-difluoro-phenyl)-methanone and 4-ethoxy phenyl isocyanate | 514.5 |

According to the procedure described for the synthesis of example 42A1 further derivatives have been synthesized from the respective trans-{1-[2-(4-amino-cyclohexyl)-ethyl]-piperidin-4-yl}-(2,4-difluoro-phenyl)-methanone (example 58, intermediate F) and the corresponding amine. They comprise examples 65A1 to 65A4.

| Ex. No | Systematic name | MW | Starting materials | MW found (M + H)+ |
|---|---|---|---|---|
| 65A1 | 4-Phenyl-piperazine-1-carboxylic acid trans (4-{2-[4-(2,4-difluoro-benzoyl)-piperidin-1-yl]-ethyl}-cyclohexyl)-amide | 538.7 | Trans {1-[2-(4-amino-cyclohexyl)-ethyl]-piperidin-4-yl}-(2,4-difluoro-phenyl)-methanone hydrochloride and 1-phenyl-piperazine | 539.0 |
| 65A2 | 2,3-Dihydro-indole-1-carboxylic acid (4-{2-[4-(2,4-difluoro-benzoyl)-piperidin-1-yl]-ethyl}-cyclohexyl)-amide | 495.6 | {1-[2-(4-amino-cyclohexyl)-ethyl]-piperidin-4-yl}-(2,4-difluoro-phenyl)-methanone hydrochloride and indoline | 496.2 |
| 65A4 | Morpholine-4-carboxylic acid (4-{2-[4-(2,4-difluoro-benzoyl)-piperidin-1-yl]-ethyl}-cyclohexyl)-amide | 463.6 | {1-[2-(4-amino-cyclohexyl)-ethyl]-piperidin-4-yl}-(2,4-difluoro-phenyl)-methanone hydrochloride and morpholine | 464.2 |
| 65A4 | Pyrrolidine-1-carboxylic acid (4-{2-[4-(2,4-difluoro-benzoyl)-piperidin-1-yl]-ethyl}-cyclohexyl)-amide | 447.6 | {1-[2-(4-amino-cyclohexyl)-ethyl]-piperidin-4-yl}-(2,4-difluoro-phenyl)-methanone hydrochloride and pyrrolidine | 448.3 |

Example 65A5

Quinoline-4-carboxylic acid trans-(4-{2-[4-(3,4-difluoro-benzoyl)-piperidin-1-yl]-ethyl}-cyclohexyl)-amide The title compound was prepared according to example 1 from Trans {1-[2-(4-amino-cyclohexyl)-ethyl]-piperidin-4-yl}-(2,4-difluoro-phenyl)-methanone and Quinoline-4-carboxylic acid to yield a white solid. (m/e): 506.3 (M+H$^+$).

Further amide derivates were synthesized from Trans {1-[2-(4-amino-cyclohexyl)-ethyl]-piperidin-4-yl}-(2,4-difluoro-phenyl)-methanone and the respective acid. The purification was performed with preparative HPLC on reversed phase column material eluting with a gradient formed from acetonitrile/water (0.05% Et$_3$N). The evaporation of the product fractions yielded the respective amides which comprise examples 65A5 to example 65A17.

| Ex. No | Systematic name | MW | Starting materials | MW found (M + H)+ |
|---|---|---|---|---|
| 65A5 | Quinoline-4-carboxylic acid trans (4-{2-[4-(3,4-difluoro-benzoyl)-piperidin-1-yl]-ethyl}-cyclohexyl)-amide | 505.6 | Trans {1-[2-(4-amino-cyclohexyl)-ethyl]-piperidin-4-yl}-(2,4-difluoro-phenyl)-methanone and Quinoline-4-carboxylic acid | 506.3 |
| 65A6 | Tetrahydro-furan-3-carboxylic acid trans (4-{2-[4-(3,4-difluoro-benzoyl)-piperidin-1-yl]-ethyl}-cyclohexyl)-amide | 448.5 | Trans {1-[2-(4-amino-cyclohexyl)-ethyl]-piperidin-4-yl}-(2,4-difluoro-phenyl)-methanone Tetrahydro-furan-3-carboxylic acid | 449.4 |
| 65A7 | Cyclopropanecarboxylic acid (4-{2-[4-(3,4-difluoro-benzoyl)-piperidin-1-yl]-ethyl}-cyclohexyl)-amide | 418.5 | Trans {1-[2-(4-amino-cyclohexyl)-ethyl]-piperidin-4-yl}-(2,4-difluoro-phenyl)-methanone and Cyclopropane-carboxylic acid | 419.3 |
| 65A8 | 5-Methanesulfonyl-thiophene-2-carboxylic acid (4-{2-[4-(3,4-difluoro-benzoyl)-piperidin-1-yl]-ethyl}-cyclohexyl)-amide | 538.6 | Trans {1-[2-(4-amino-cyclohexyl)-ethyl]-piperidin-4-yl}-(2,4-difluoro-phenyl)-methanone and 5-Methanesulfonyl-thiophene-2-carboxylic acid | 539.5 |
| 65A9 | N-trans (4-{2-[4-(3,4-Difluoro-benzoyl)-piperidin-1-yl]-ethyl}-cyclohexyl)-butyramide | 420.5 | Trans {1-[2-(4-amino-cyclohexyl)-ethyl]-piperidin-4-yl}-(2,4-difluoro-phenyl)-methanone and butyric acid | 421.1 |
| 65A10 | 2,2-Difluoro-cyclopropanecarboxylic acid (4-{2-[4-(3,4-difluoro-benzoyl)-piperidin-1-yl]-ethyl}-cyclohexyl)-amide | 454.3 | Trans {1-[2-(4-amino-cyclohexyl)-ethyl]-piperidin-4-yl}-(2,4-difluoro-phenyl)-methanone and 2,2-Difluoro-cyclopropane-carboxylic acid | 455.3 |
| 65A11 | Tetrahydro-pyran-4-carboxylic acid (4-{2-[4-(3,4-difluoro-benzoyl)-piperidin-1-yl]-ethyl}-cyclohexyl)-amide | 462.5 | Trans {1-[2-(4-amino-cyclohexyl)-ethyl]-piperidin-4-yl}-(2,4-difluoro-phenyl)-methanone and Tetrahydro-pyran-4-carboxylic acid | 463.4 |
| 65A12 | 2-Cyclopropyl-N-(4-{2-[4-(3,4-difluoro-benzoyl)-piperidin-1-yl]-ethyl}-cyclohexyl)-acetamide | 432.5 | Trans {1-[2-(4-amino-cyclohexyl)-ethyl]-piperidin-4-yl}-(2,4-difluoro-phenyl)-methanone and 2-Cyclopropyl acetamide | 433.2 |
| 65A13 | Chroman-3-carboxylic acid (4-{2-[4-(3,4-difluoro-benzoyl)-piperidin-1-yl]-ethyl}-cyclohexyl)-amide | 510.6 | Trans {1-[2-(4-amino-cyclohexyl)-ethyl]-piperidin-4-yl}-(2,4-difluoro-phenyl)-methanone and Chroman-3-carboxylic acid | 511.5 |
| 65A14 | 4-Cyano-N-trans (4-{2-[4-(3,4-difluoro-benzoyl)-piperidin-1-yl]-ethyl}-cyclohexyl)-benzamide | 479.5 | Trans {1-[2-(4-amino-cyclohexyl)-ethyl]-piperidin-4-yl}-(2,4-difluoro-phenyl)-methanone and 4-cyano benzoic acid | 480.5 |
| 65A15 | N-trans (4-{2-[4-(3,4-Difluoro-benzoyl)-piperidin-1-yl]-ethyl}-cyclohexyl)-4-pyrrol-1-yl-benzamide | 519.6 | Trans {1-[2-(4-amino-cyclohexyl)-ethyl]-piperidin-4-yl}-(2,4-difluoro-phenyl)-methanone and 4-pyrrol benzoic acid | 520.2 |
| 65A16 | N-trans (4-{2-[4-(3,4-Difluoro-benzoyl)-piperidin-1-yl]-ethyl}-cyclohexyl)-4-pyrrol-1-yl-benzamide | 519.6 | Trans {1-[2-(4-amino-cyclohexyl)-ethyl]-piperidin-4-yl}-(2,4-difluoro-phenyl)-methanone and 4-pyrrol benzoic acid | 520.2 |

-continued

| Ex. No | Systematic name | MW | Starting materials | MW found (M + H)+ |
|---|---|---|---|---|
| 65A17 | N-trans (4-{2-[4-(3,4-Difluoro-benzoyl)-piperidin-1-yl]-ethyl}-cyclohexyl)-4-morpholin-4-yl-benzamide | 539.6 | Trans {1-[2-(4-amino-cyclohexyl)-ethyl]-piperidin-4-yl}-(2,4-difluoro-phenyl)-methanone and 4-morpholine benzoic acid | 540.5 |

Example 65A18

2-Benzyloxy-N-trans (4-{2-[4-(2-chloro-4-fluoro-benzoyl)-piperidin-1-yl]-ethyl}-cyclohexyl)-acetamide Step 1

1-[4-(2-Chloro-4-fluoro-benzoyl)-piperidin-1-yl]-ethanone

2-Chloro-4-fluoro-1-iodobenzol (5 g, 19 mmol) is solved in THF (3 mL) and at −10° C. isopropyl magnesium chloride-lithium chloride (2M in THF) was added dropwise and the mixture stirred for 30 minutes at 0° C. At −10° C. 1-acetyl-isonipecotoyl chloride is added (3.3 g, 18 mmol) solved in THF (2 mL) and the mixture stirred for 10 minutes to −10° C. and 4 h to 0° C. Water was added and the reaction extracted with dichloromethane. Chromatography with Heptane/EtOAc (2:1) gave the desired compound as a clear orange liquid (1.8 g, 33% yield). (m/e): 284.3 (M+H$^+$).

Step 2

(2-Chloro-4-fluoro-phenyl)-piperidin-4-yl-methanone; hydrochloride

1-[4-(2-Chloro-4-fluoro-benzoyl)-piperidin-1-yl]-ethanone (1.8 g, 6.5 mmol) was solved in 6 N HCl (17 mL) and water was added 17 mL. The mixture is stirred at reflux overnight. Diethylether (20 mL) was added and the reaction extracted. The organic phase was discarded and to the water an aqueous solution (10%) of sodium hydroxide was added until pH 11 and was extracted with dichloromethane. Removal of the solvent gave 1.1 g, 5 mmol of the title compound (66% yield). (m/e): 242.3 (M+H$^+$).

Intermediate E and F

Trans {1-[2-(4-Amino-cyclohexyl)-ethyl]-piperidin-4-yl}-(2-chloro-4-fluoro-phenyl)-methanone The title compound was prepared following the steps already described on example 1 from (2-Chloro-4-fluoro-phenyl)-piperidin-4-yl-methanone and Trans-[4-(2-Oxo-ethyl)-cyclohexyl]-carbamic acid tert-butyl ester following removal of the Boc protecting group by treatment with trifluoroacetic acid. (m/e): 367.4 (M+H$^+$).

2-Benzyloxy-N-trans (4-{2-[4-(2-chloro-4-fluoro-benzoyl)-piperidin-1-yl]-ethyl}-cyclohexyl)-acetamide The title compound was prepared as described on example 1 from Trans {1-[2-(4-Amino-cyclohexyl)-ethyl]-piperidin-4-yl}-(2-chloro-4-fluoro-phenyl)-methanone, 2-(1H-benzotriazol-1-yl)-1,1,3,3-tetramethyl uronium tetrafluoroborate, N-ethyldiisopropylamine and 2-Benzyloxy acetic acid in DMF. (m/e): 515.3 (M+H$^+$).

According to the procedure described for the synthesis of example 65A18 further derivatives have been synthesized from Trans {1-[2-(4-Amino-cyclohexyl)-ethyl]-piperidin-4-yl}-(2-chloro-4-fluoro-phenyl)-methanone and the corresponding acid. The purification was performed with preparative HPLC on reversed phase column material eluting with a gradient formed from acetonitrile/water (0.05% Et$_3$N). The evaporation of the product fractions yielded the respective amides which comprise examples 65A18 to example 65A28.

| Ex. No | Systematic name | MW | Starting materials | MW found (M + H)+ |
|---|---|---|---|---|
| 65A18 | 2-Benzyloxy-N-trans (4-{2-[4-(2-chloro-4-fluoro-benzoyl)-piperidin-1-yl]-ethyl}-cyclohexyl)-acetamide | 515.1 | Trans {1-[2-(4-Amino-cyclohexyl)-ethyl]-piperidin-4-yl}-(2-chloro-4-fluoro-phenyl)-methanone and 2-Benzyloxy acetic acid | 515.3 |
| 65A19 | N-trans (4-{2-[4-(2-Chloro-4-fluoro-benzoyl)-piperidin-1-yl]-ethyl}-cyclohexyl)-4-morpholin-4-yl-benzamide | 556.1 | Trans {1-[2-(4-Amino-cyclohexyl)-ethyl]-piperidin-4-yl}-(2-chloro-4-fluoro-phenyl)-methanone and 4-morpholine benzoic acid | 556.1 |
| 65A20 | Tetrahydro-furan-3-carboxylic acid trans (4-{2-[4-(2-chloro-4-fluoro-benzoyl)-piperidin-1-yl]-ethyl}-cyclohexyl)-amide | 465.1 | Trans {1-[2-(4-Amino-cyclohexyl)-ethyl]-piperidin-4-yl}-(2-chloro-4-fluoro-phenyl)-methanone and Tetrahydro-furan-3-carboxylic acid | 465.3 |
| 65A21 | Cyclopropane-carboxylic acid trans (4-{2-[4-(2-chloro-4-fluoro-benzoyl)-piperidin-1-yl]-ethyl}-cyclohexyl)-amide | 434.9 | Trans {1-[2-(4-Amino-cyclohexyl)-ethyl]-piperidin-4-yl}-(2-chloro-4-fluoro-phenyl)-methanone and Cyclopropane-carboxylic acid | 435.4 |
| 65A22 | N-trans (4-{2-[4-(2-Chloro-4-fluoro-benzoyl)-piperidin-1-yl]-ethyl}-cyclohexyl)-butyramide | 437.0 | Trans {1-[2-(4-Amino-cyclohexyl)-ethyl]-piperidin-4-yl}-(2-chloro-4-fluoro-phenyl)-methanone and butyric acid | 437.4 |

-continued

| Ex. No | Systematic name | MW | Starting materials | MW found (M + H)+ |
|---|---|---|---|---|
| 65A23 | N-trans (4-{2-[4-(2-Chloro-4-fluoro-benzoyl)-piperidin-1-yl]-ethyl}-cyclohexyl)-2-cyclopropyl-acetamide | 449.0 | Trans {1-[2-(4-Amino-cyclohexyl)-ethyl]-piperidin-4-yl}-(2-chloro-4-fluoro-phenyl)-methanone and 2-cyclopropyl-acetic acid | 449.4 |
| 65A24 | N-trans (4-{2-[4-(2-Chloro-4-fluoro-benzoyl)-piperidin-1-yl]-ethyl}-cyclohexyl)-propionamide | 437.0 | Trans {1-[2-(4-Amino-cyclohexyl)-ethyl]-piperidin-4-yl}-(2-chloro-4-fluoro-phenyl)-methanone and propionic cid | 437.4 |
| 65A25 | Tetrahydro-pyran-4-carboxylic acid (4-{2-[4-(2-chloro-4-fluoro-benzoyl)-piperidin-1-yl]-ethyl}-cyclohexyl)-amide | 479.04 | Trans {1-[2-(4-Amino-cyclohexyl)-ethyl]-piperidin-4-yl}-(2-chloro-4-fluoro-phenyl)-methanone and Tetrahydro-pyran-4-carboxylic acid | 479.3 |
| 65A26 | 5-Methanesulfonyl-thiophene-2-carboxylic acid (4-{2-[4-(2-chloro-4-fluoro-benzoyl)-piperidin-1-yl]-ethyl}-cyclohexyl)-amide | 555.1 | Trans {1-[2-(4-Amino-cyclohexyl)-ethyl]-piperidin-4-yl}-(2-chloro-4-fluoro-phenyl)-methanone and 5-Methanesulfonyl-thiophene-2-carboxylic acid | 555.3 |
| 65A27 | N-trans (4-{2-[4-(2-Chloro-4-fluoro-benzoyl)-piperidin-1-yl]-ethyl}-cyclohexyl)-3-methoxy-propionamide | 453.0 | Trans {1-[2-(4-Amino-cyclohexyl)-ethyl]-piperidin-4-yl}-(2-chloro-4-fluoro-phenyl)-methanone and 3-methoxy-propionic acid | 453.2 |
| 65A28 | 4-Chloro-N-trans (4-{2-[4-(2-chloro-4-fluoro-benzoyl)-piperidin-1-yl]-ethyl}-cyclohexyl)-benzamide | 505.1 | Trans {1-[2-(4-Amino-cyclohexyl)-ethyl]-piperidin-4-yl}-(2-chloro-4-fluoro-phenyl)-methanone and 4-Chloro benzoic acid | 505.4 |

Example 65A29

N-trans (4-{2-[4-(2-Chloro-4-fluoro-benzoyl)-piperidin-1-yl]-ethyl}-cyclohexyl)-acetamide Prepared as described on example 36 from Trans {1-[2-(4-Amino-cyclohexyl)-ethyl]-piperidin-4-yl}-(2-chloro-4-fluoro-phenyl)-methanone and acetyl chloride. MS (m/e): 409.4 (M+H$^+$)

Example 66

4-Ethoxy-N {4-[4-(4-fluoro-benzoyl)-piperidin-1-yl]-butyl}-benzamide

Intermediate AC

{4-[4-(4-Fluoro-benzoyl)-piperidin-1-yl]-butyl}-carbamic acid tert-butyl ester 4-(4-fluorobenzoyl)piperidine hydrochloride (0.5 g, 2.01 mmol) is suspended in acetonitrile (5 mL), 4-(Boc-amino) Butyl Bromide was added (0.569 g, 2.01 mmol) and sodium iodide (0.461 g, 3.02 mmol) and the mixture was stirred at 80° C. overnight. Water was added and the aqueous phase was extracted with 30 mL dichloromethane. The combined organic phases were dried with magnesium sulfate, filtrated concentrated and purified with column chromatography on silica using dichloromethane/Methanol (95/0.5) to yield 0.830 g, (2.1 mmol, 100% yield) of the title compound as a brown solid. MS (m/e): 379.2 (M+H$^+$).

Intermediate AD

[1-(4-Amino-butyl)-piperidin-4-yl]-(4-fluoro-phenyl)-methanone; trifluoro-acetic acid salt According to the procedure described for the synthesis of Trans-{1-[2-(4-Amino-cyclohexyl)-ethyl]-piperidin-4-yl}-(4-fluoro-phenyl)-methanone, trifluoroacetic acid salt (intermediate F), the title compound was synthesized from {4-[4-(4-Fluoro-benzoyl)-piperidin-1-yl]-butyl}-carbamic acid tert-butyl ester and trifluoroacetic acid. MS (m/e): 279.2 (M+H$^+$).

4-Ethoxy-N-{4-[4-(4-fluoro-benzoyl)-piperidin-1-yl]-butyl}-benzamide

According to the procedure described for the synthesis of {4-Chloro-N-trans (4-{2-[4-(4 fluoro-benzoyl)-piperidin-1-yl]-ethyl}-cyclohexyl)-benzamide (example 1) the title compound was synthesized from Trans-[1-(4-Amino-butyl)-piperidin-4-yl]-(4-fluoro-phenyl)-methanone; trifluoro-acetic acid salt and 4-Ethoxy benzoic acid using 2-(1H-benzotriazol-1-yl)-1,1,3,3-tetramethyl uronium tetrafluoroborate and N-ethyldiisopropylamine in DMF. MS (m/e): 427.3 (M+H$^+$).

Following the procedure described for the synthesis of example 66, further amide derivates were synthesized from [1-(4-Amino-butyl)-piperidin-4-yl]-(4-fluoro-phenyl)-methanone; trifluoro-acetic acid salt and the respective commercially available acid. The purification was performed with preparative HPLC on reversed phase column material eluting with a gradient formed from acetonitrile/water (0.05% Et$_3$N). The evaporation of the product fractions yielded the respective amides which comprise examples 66 and example 68.

| Ex. No | Systematic name | MW | Starting materials | MW found (M + H)+ |
|---|---|---|---|---|
| 66 | 4-Ethoxy-N-{4-[4-(4-fluoro-benzoyl)-piperidin-1-yl]-butyl}-benzamide | 426.5 | [1-(4-Amino-butyl)-piperidin-4-yl]-(4-fluoro-phenyl)-methanone; trifluoro-acetic acid salt and 4-Ethoxy benzoic acid | 427.3 |

-continued

| Ex. No | Systematic name | MW | Starting materials | MW found (M + H)+ |
|---|---|---|---|---|
| 67 | N-{4-[4-(4-Fluoro-benzoyl)-piperidin-1-yl]-butyl}-3-(5-methyl-[1,2,4]oxadiazol-3-yl)-benzamide | 464.5 | [1-(4-Amino-butyl)-piperidin-4-yl]-(4-fluoro-phenyl)-methanone; trifluoro-acetic acid salt and 3-(5-methyl-[1,2,4]oxadiazol-3-yl)-benzoic acid | 465.1 |
| 68 | Tetrahydro-furan-3-carboxylic acid {4-[4-(4-fluoro-benzoyl)-piperidin-1-yl]-butyl}-amide | 376.4 | [1-(4-Amino-butyl)-piperidin-4-yl]-(4-fluoro-phenyl)-methanone; trifluoro-acetic acid salt and Tetrahydro-furan-3-carboxylic acid | 377.2 |

Example 69

1-(4-Chloro-phenyl)-3-{4-[4-(4-fluoro-benzoyl)-piperidin-1-yl]-butyl}-urea

The title compound was synthesized from Trans-[1-(4-Amino-butyl)-piperidin-4-yl]-(4-fluoro-phenyl)-methanone; trifluoro-acetic acid salt and 4-Chloro phenyl isocyanate in acetonitrile according to the procedure described for example 38. MS (m/e): 432.05 (M$^+$).

Following the procedure described for the synthesis of example 59, further ureas were synthesized using the respective commercially available isocyanate. The purification was performed with preparative HPLC on reversed phase column material eluting with a gradient formed from acetonitrile/water (0.05% Et$_3$N). The evaporation of the product fractions yielded the respective ureas.

| Ex. No | Systematic name | MW | Starting materials | MW found (M + H)+ |
|---|---|---|---|---|
| 69 | 1-(4-Chloro-phenyl)-3-{4-[4-(4-fluoro-benzoyl)-piperidin-1-yl]-butyl}-urea | 431.9 | [1-(4-Amino-butyl)-piperidin-4-yl]-(4-fluoro-phenyl)-methanone; trifluoro-acetic acid salt and 4-Chlorophenyl isocyanate | 432.5 |
| 70 | 1-(4-Ethoxy-phenyl)-3-{4-[4-(4-fluoro-benzoyl)-piperidin-1-yl]-butyl}-urea | 491.5 | [1-(4-Amino-butyl)-piperidin-4-yl]-(4-fluoro-phenyl)-methanone; trifluoro-acetic acid salt and 4-Ethoxyphenyl isocyanate | 492.4 |

Example 71

Quinoline-4-carboxylic acid trans-(4-{2-[4-(2-chloro-benzoyl)-piperidin-1-yl]-ethyl}-cyclohexyl)-amide Intermediate E Trans-(4-{2-[4-(2 Chloro-benzoyl)-piperidin-1-yl]-ethyl}-cyclohexyl)-carbamic acid tert-butyl ester According to the procedure described for the synthesis of Trans-(4-{2-[4-(4 Fluoro-benzoyl)-piperidin-1-yl]-ethyl}-cyclohexyl)-carbamic acid tert-butyl ester (intermediate E, example 1), the title compound was synthesized from 4-{2-[4-(2-chloro-benzoyl)]piperidine and Trans-[4-(2-Oxo-ethyl)-cyclohexyl]-carbamic acid tert-butyl ester. MS (m/e): 450.1 (M+H$^+$).

Intermediate F

Trans-{1-[2-(4-Amino-cyclohexyl)-ethyl]-piperidin-4-yl}-(2-chloro-phenyl)-methanone; trifluoro-acetic acid salt According to the procedure described for the synthesis of {1-trans-[2-(4-Amino-cyclohexyl)-ethyl]-piperidin-4-yl}-(4-fluoro-phenyl)-methanone, trifluoroacetic acid salt (intermediate F, example 1), the title compound was synthesized from Trans-(4-{2-[4-(2 Chloro-benzoyl)-piperidin-1-yl]-ethyl}-cyclohexyl)-carbamic acid tert-butyl ester and trifluoroacetic acid. MS (m/e): 349.5 (M+H$^+$).

Quinoline-4-carboxylic acid trans-(4-{2-[4-(2 chloro-benzoyl)-piperidin-1-yl]-ethyl}-cyclohexyl)-amide According to the procedure described for the synthesis of {4-Chloro-N-trans (4-{2-[4-(4 fluoro-benzoyl)-piperidin-1-yl]-ethyl}-cyclohexyl)-benzamide (example 1) the title compound was synthesized from Trans-{1-[2-(4-Amino-cyclohexyl)-ethyl]-piperidin-4-yl}-(2-chloro-phenyl)-methanone; trifluoro-acetic acid salt and Quinoline-4-carboxylic acid using 2-(1H-benzotriazol-1-yl)-1,1,3,3-tetramethyl uronium tetrafluoroborate and N-ethyldiisopropylamine in DMF. MS (m/e): 504.4 (M+H$^+$).

Further amide derivates were synthesized from Trans-{1-[2-(4-Amino-cyclohexyl)-ethyl]-piperidin-4-yl}-(2-chloro-phenyl)-methanone; trifluoro-acetic acid salt and the respective commercially available acid. The purification was performed with preparative HPLC on reversed phase column material eluting with a gradient formed from acetonitrile/water (0.05% Et$_3$N). The evaporation of the product fractions yielded the respective amides which comprise examples 71 to example 72.

| Ex. No | Systematic name | MW | Starting materials | MW found (M + H)+ |
|---|---|---|---|---|
| 71 | Quinoline-4-carboxylic acid trans-(4-{2-[4-(2-chloro-benzoyl)-piperidin-1-yl]-ethyl}-cyclohexyl)-amide | 504.07 | Trans-{1-[2-(4-Amino-cyclohexyl)-ethyl]-piperidin-4-yl}-(2-chloro-phenyl)-methanone; trifluoro-acetic | 504.4 |

-continued

| Ex. No | Systematic name | MW | Starting materials | MW found (M + H)+ |
|---|---|---|---|---|
| 72 | N-trans (4-{2-[4-(2-Chloro-benzoyl)-piperidin-1-yl]-ethyl}-cyclohexyl)-acetamide | 390.9 | acid salt and Quinoline-4-carboxylic acid Trans-{1-[2-(4-Amino-cyclohexyl)-ethyl]-piperidin-4-yl}-(2-chloro-phenyl)-methanone; trifluoro-acetic acid salt and Acetic Acid | 391.3 |

Example 73

N-trans (4-{2-[4-(2,4-Dichloro-benzoyl)-piperidin-1-yl]-ethyl}-cyclohexyl)-4-morpholin-4-yl-benzamide Step 1

1-[4-(2,4-Dichloro-benzoyl)-piperidin-1-yl]-ethanone

Acetylisonipecotoyl chloride (8 g, 42 mmol) was solved in dichlorobenzene and aluminium chloride (11.2 gr, 894 mmol) was added portionwise. The mixture was refluxed at 90° C. for 4 h after complexion of the reaction. Ice/water was added to the mixture that was extracted with dichloromethane. After chromatography from heptane to EtOAc the product was obtained as a yellow oil (6.3 g, 50%). MS (m/e): 300.2 (M+H$^+$)

Step 2

(2,4-Dichloro-phenyl)-piperidin-4-yl-methanone

Removal of the acetyl protecting group was performed refluxing on 6 N HCl as described on example 65A18. MS (m/e): 258.0 (M+H$^+$)

Intermediate E

Trans (4-{2-[4-(2,4-Dichloro-benzoyl)-piperidin-1-yl]-ethyl}-cyclohexyl)-carbamic acid tert-butyl ester The title compound was prepared as described on example 1 from (2,4-Dichloro-phenyl)-piperidin-4-yl-methanone and Trans-[4-(2-Oxo-ethyl)-cyclohexyl]-carbamic acid tert-butyl ester (m/e): 483.4 (M+H$^+$)

Intermediate F

Trans {1-[2-(4-Amino-cyclohexyl)-ethyl]-piperidin-4-yl}-(2,4-dichloro-phenyl)-methanone The title compound was prepared as described on example 1 from Trans (4-{2-[4-(2,4-Dichloro-benzoyl)-piperidin-1-yl]-ethyl}-cyclohexyl)-carbamic acid tert-butyl ester and trifluoroacetic acid (m/e): 383.3 (M+H$^+$).

N-trans (4-{2-[4-(2,4-Dichloro-benzoyl)-piperidin-1-yl]-ethyl}-cyclohexyl)-4-morpholin-4-yl-benzamide The title compound was prepared as described on example 1 from Trans {1-[2-(4-Amino-cyclohexyl)-ethyl]-piperidin-4-yl}-(2,4-dichloro-phenyl)-methanone and 4-morpholino benzoic acid using 2-(1H-benzotriazol-1-yl)-1,1,3,3-tetramethyl uronium tetrafluoroborate and N-ethyldiisopropylamine in DMF (m/e): 572.3 (M+H$^+$)

Example 74

N-Trans (4-{2-[4-(2,4-Dichloro-benzoyl)-piperidin-1-yl]-ethyl}-cyclohexyl)-acetamide Prepared as described on example 36 from Trans {1-[2-(4-Amino-cyclohexyl)-ethyl]-piperidin-4-yl}-(2,4-Dichloro-phenyl)-methanone and acetyl chloride. MS (m/e): 425.3 (M+H$^+$)

Example 75

N-Trans (4-{2-[4-(2,5-Dichloro-benzoyl)-piperidin-1-yl]-ethyl}-cyclohexyl)-acetamide 1-[4-(2,5-Dichloro-benzoyl)-piperidin-1-yl]-ethanone The title compound was prepared according as described on example 65A18 from 2,5 Dichloro 1-iodobenzol, isopropyl magnesium chloride-lithium chloride (2M in THF) and 1-acetyl-isonipecotoyl chloride. (m/e): 301.1 (M+H$^+$).

(2,5-Dichloro-phenyl)-piperidin-4-yl-methanone

Removal of the acetyl protecting group was performed refluxing on 6 N HCl as described on example 65A18. MS (m/e): 258.1 (M+H$^+$)

Intermediate E

Trans (4-{2-[4-(2,5-Dichloro-benzoyl)-piperidin-1-yl]-ethyl}-cyclohexyl)-carbamic acid tert-butyl ester The title compound was prepared as described on example 1 from (2,5-Dichloro-phenyl)-piperidin-4-yl-methanone and Trans-[4-(2-Oxo-ethyl)-cyclohexyl]-carbamic acid tert-butyl ester (m/e): 483.5 (M+H$^+$)

Intermediate F

Trans {1-[2-(4-Amino-cyclohexyl)-ethyl]-piperidin-4-yl}-(2,5-dichloro-phenyl)-methanone The title compound was prepared as described on example 1 from Trans (4-{2-[4-(2,5-Dichloro-benzoyl)-piperidin-1-yl]-ethyl}-cyclohexyl)-carbamic acid tert-butyl ester and trifluoroacetic acid (m/e): 383.0 (M+H$^+$).

N-Trans (4-{2-[4-(2,5-Dichloro-benzoyl)-piperidin-1-yl]-ethyl}-cyclohexyl)-acetamide Prepared as described on example 36 from Trans {1-[2-(4-Amino-cyclohexyl)-ethyl]-piperidin-4-yl}-(2,4-Dichloro-phenyl)-methanone and acetyl chloride. MS (m/e): 425.3 (M+H$^+$).

Example 76

N-Trans (4-{2-[4-(4-Fluoro-2-methyl-benzoyl)-piperidin-1-yl]-ethyl}-cyclohexyl)-acetamide Prepared as described on example 36 from Trans {1-[2-(4-Amino-cyclohexyl)-ethyl]-piperidin-4-yl}-(4-fluoro-2-methyl-phenyl)-methanone (prepared as the Trans {1-[2-(4-Amino-cyclohexyl)-ethyl]-piperidin-4-yl}-(2-chloro-4-fluoro-phenyl)-methanone described on example 65A18 and acetyl chloride. MS (m/e): 389.1 (M+H$^+$).

General Procedure A.1 for the Reductive Amination

A mixture of amine hydrochloride (1.0 eq.) and aldehyde (1.1 eq.) in 1,2-dichloroethane (ca. 0.2 M) was stirred over night at room temperature. Na(AcO)$_3$BH (1.5 eq.) was added and the reaction was monitored by TLC and MS. After completion sat. aq. NHCO$_3$ sol. was added and the product was extracted with CH$_2$Cl$_2$. After drying (Na$_2$SO$_4$ or MgSO$_4$) the solvent was evaporated and the product purified by flash chromatography.

General Procedure A.2 for the Reductive Amination

A mixture of amine hydrochloride (1.0 eq.) aldehyde (1.1 eq.) and AcOH (2.0 eq.) in 1,2-dichloroethane (ca. 0.2 M) was stirred over night at room temperature. Na(AcO)$_3$BH (1.5 eq.) was added and the reaction was monitored by TLC and MS. After completion sat. aq. NHCO$_3$ sol. was added and the product was extracted with CH$_2$Cl$_2$. After drying (Na$_2$SO$_4$ or MgSO$_4$) the solvent was evaporated and the product purified by flash chromatography.

General Procedure B.1 for the Boc Cleavage

A mixture of Boc protected amine (1.0 eq.), MeOH (10 eq.) and 4.6 M HCl in EtOAc (15 eq.) was stirred until no more starting material was detected by TLC and MS. The solid product was collected by filtration and dried under HV.

General Procedure B.2 for the Boc Cleavage

To a solution of Boc protected amine (1.0 eq.) in CH$_2$Cl$_2$ (ca. 0.2 M) was added a saturated solution of HCl in Et$_2$O (½ the volume of CH$_2$Cl$_2$). The mixture was stirred until no more starting material was detected by TLC and MS. The product was precipitated by addition of Et$_2$O, collected by filtration, washed with more Et$_2$O and dried under HV.

General Procedure C for the Amide Formation

To a stirred solution under N2 of acid (1.1 eq.) in DMF (ca. 0.1 M) was added TBTU (1.1 eq.) and Et$_3$N (3.1 eq.). After stirring 1 h at room temperature the amine hydrochloride was added (1.0 eq.). Stirring was continued and the reaction was monitored by TLC and MS. After completion sat. aq. NHCO$_3$ sol. was added and the product was extracted with 3 portions of EtOAc. After drying (Na$_2$SO$_4$ or MgSO$_4$) the solvent was evaporated and the crude product was purified by flash chromatography.

General Procedure D

A 1.6 M solution of n-BuLi (1.1 eq.) in Hex was added dropwise to a solution under inert atmosphere of the thiophene (1.1 eq.) in THF (0.1 M) at −78° C. After stirring 2 h at −78° C. 4-formyl-piperidine-1-carboxylic acid tert-butyl ester (1.0 eq.) dissolved in a small amount of THF was added. Stirring at −78° C. was continued 2.5 h then the reaction mixture was allowed to warm to room temperature, poured into EtOAc and washed with sat. aq.NaHCO$_3$ sol. The aqueous layers were extracted with more EtOAc. The combined organic layers were dried (Na$_2$SO$_4$ or MgSO$_4$), the solvent was evaporated and the product purified by flash chromatography.

General Procedure E.1 for the MnO$_2$ Oxidation of Alcohols to Ketones

MnO$_2$ (20 eq.) was added to a solution of alcohol (1.0 eq.) in CH$_2$Cl$_2$ (0.1 M). The resulting mixture was stirred over night at 30° C. Filtration over Dicalite and evaporation of the solvent afforded the crude product that was purified by flash chromatography.

General Procedure E.2 for the TPAP Oxidation of Alcohols to Ketones

The alcohol (1.0 eq.) was dissolved in CH$_2$Cl$_2$ (0.25 M), powdered 4 Å molecular sieves (500 mg/mmol) and NMO were added followed by tetrapropylammonium perruthenate (0.05 eq.). The reaction mixture was stirred at room temperature and monitored by TLC. After completion the mixture was diluted with CH$_2$Cl$_2$ then washed with 1 M aq. Na$_2$SO$_3$ solution, brine and finally a 1 M aq. CuSO$_4$ solution. Drying (Na$_2$SO$_4$ or MgSO$_4$) and evaporation of the solvent afforded the crude product that was purified by flash chromatography.

Example 77

N-{trans-4-[2-(4-Benzoyl-piperidin-1-yl)-ethyl]-cyclohexyl}-acetamide

Step 1

{trans-4-[2-(4-Benzoyl-piperidin-1-yl)-ethyl]-cyclohexyl}-carbamic acid tert-butyl ester From 4-benzoylpiperidine hydrochloride (200 mg) and [trans-4-(2-oxo-ethyl)-cyclohexyl]-carbamic acid tert-butyl ester (intermediate C, 235 mg) by procedure A.2. Yield: 181 mg (49%). Off-white solid. MS (m/z): 415.3 ([M+H]$^+$).

Step 2

{1-[2-(trans-4-Amino-cyclohexyl)-ethyl]-piperidin-4-yl}-phenyl-methanone dihydrochloride From {trans-4-[2-(4-benzoyl-piperidin-1-yl)-ethyl]-cyclohexyl}-carbamic acid tert-butyl ester (172 mg) by procedure B.1. Yield: 148 mg (92%). White solid. MS (m/z): 315.1 ([M+H])$^+$.

Step 3

N-{trans-4-[2-(4-Benzoyl-piperidin-1-yl)-ethyl]-cyclohexyl}-acetamide

From {1-[2-(trans-4-amino-cyclohexyl)-ethyl]-piperidin-4-yl}-phenyl-methanone dihydrochloride (138 mg) and acetic acid (23 mg) by procedure C. Yield: 85 mg (66%). White solid. 357.3 ([M+H]$^+$).

Example 78

N-(trans-4-{2-[4-(4-Chloro-benzoyl)-piperidin-1-yl]-ethyl}-cyclohexyl)-4-morpholin-4-yl-benzamide Step 1

(trans-4-{2-[4-(4-Chloro-benzoyl)-piperidin-1-yl]-ethyl}-cyclohexyl)-carbamic acid tert-butyl ester From (4-chlorophenyl)(4-piperidyl)methanone hydrochloride (100 mg) and [trans-4-(2-oxo-ethyl)-cyclohexyl]- carbamic acid tert-butyl ester (intermediate C, 102 mg) by procedure A.1. Yield: 128 mg (74%). Light yellow solid. MS (m/z): 449.3 ([M+H]$^+$).

Step 2

{1-[2-(trans-4-Amino-cyclohexyl)-ethyl]-piperidin-4-yl}-(4-chloro-phenyl)-methanone dihydrochloride From (4-{2-[4-(4-Chloro-benzoyl)-piperidin-1-yl]-ethyl}-cyclohexyl)-carbamic acid tert-butyl ester by procedure B.2. Yield: 100 mg (84%). White solid. MS (m/z): 349.3 ([M+H]$^+$).

Step 3

N-(trans-4-{2-[4-(4-Chloro-benzoyl)-piperidin-1-yl]-ethyl}-cyclohexyl)-4-morpholin-4-yl-benzamide From {1-[2-(trans-4-amino-cyclohexyl)-ethyl]-piperidin-4-yl}-(4-chloro-phenyl)-methanone dihydrochloride (100 mg) and 4-morpholin-4-yl-benzoic acid. Yield: 56 mg (40%). MS (m/z): 538.5 ([M+H]$^+$).

Examples 79 and 80

Examples 79 and 80 were prepared in analogy to example 78

| Ex. No | Systematic name | MW | Starting materials | MW found (M + H)+ |
|---|---|---|---|---|
| 79 | Tetrahydro-pyran-4-carboxylic acid (trans-4-{2-[4-(4-chloro-benzoyl)-piperidin-1-yl]-ethyl}-cyclohexyl)-amide | 461.05 | From {1-[2-(trans-4-amino-cyclohexyl)-ethyl]-piperidin-4-yl}-(4-chloro-phenyl)-methanone dihydrochloride and tetrahydro-pyran-4-carboxylic acid | 461.5 |
| 80 | (R,S)-Chroman-3-carboxylic acid (trans-4-{2-[4-(4-chloro-benzoyl)-piperidin-1-yl]-ethyl}-cyclohexyl)-amide | 509.09 | From {1-[2-(trans-4-amino-cyclohexyl)-ethyl]-piperidin-4-yl}-(4-chloro-phenyl)-methanone dihydrochloride and (R,S)-3-chromanecarboxylic acid | 509.3 |

Intermediate AG

N-[trans-4-(2-Oxo-ethyl)-cyclohexyl]-acetamide

AE (trans-4-Acetylamino-cyclohexyl)-acetic acid ethyl ester (trans-4-Amino-cyclohexyl)-acetic acid ethyl ester hydrochloride (10.0 g, 45 mmol, intermediate B) was dissolved in CH$_2$Cl$_2$ (150 ml) and Et$_3$N and AcCl (3.89 g, 50 mmol) were added. The reaction mixture was stirred 3 h at room temperature before washing it with H$_2$O and brine. After drying (Na$_2$SO$_4$) the solvent was evaporated to yield 8.42 g (82%, 37 mmol) of a white solid. MS (m/z): 228.3 ([M+H]$^+$).

AF
N-[trans-4-(2-Hydroxy-ethyl)-cyclohexyl]-acetamide

LiAlH$_4$ (2.10 g, 55 mmol) and THF (150 ml) were placed in a dry ballon. After cooling this mixture to 0° C. a solution of (trans-4-acetylamino-cyclohexyl)-acetic acid ethyl ester (8.42 g, 37 mmol) in little THF was added dropwise. The reaction was stirred 1 h before careful neutralization with H$_2$O (5.6 ml), 1 N NaOH (3×5.6 ml) and more H$_2$O (5.6 ml). The resulting mixture was stirred over night before filtering off the solids. Evaporation of the solvent and drying under high vacuum afforded 5.25 g (76%, 28 mmol) of a light brown solid. MS (m/z): 186.4 ([M+H]$^+$).

AG N-[trans-4-(2-Oxo-ethyl)-cyclohexyl]-acetamide

DMSO (3.68 g, 47 mmol) in CH$_2$Cl$_2$ (20 ml) was added at −78° C. to a stirred solution of oxalylchloride (2.9 g, 23 mmol) in CH$_2$Cl$_2$ (100 ml). After 1 h stirring at −78° C. a solution of N-[trans-4-(2-hydroxy-ethyl)-cyclohexyl]-acetamide (2.18 g, 12 mmol) in CH$_2$Cl$_2$ (80 ml) was added followed after 2 h by Et$_3$N (7.14 g, 71 mmol). The mixture was allowed to reach room temperature and was then diluted with H$_2$O and extracted with CH$_2$Cl$_2$. The combined organic layers were dried (Na$_2$SO$_4$) and the solvent was evaporated to afford the crude product. Chromatography (CH$_2$Cl$_2$/MeOH 95:5) yielded 1.75 g (81%, 9.5 mmol) of a light brown solid. MS (m/z): 184.3 ([M+H])$^+$.

Example 81

N-(trans-4-{2-[4-(Thiophene-2-carbonyl)-piperidin-1-yl]-ethyl}-cyclohexyl)-acetamide Step 1

4-(Hydroxy-thiophen-2-yl-methyl)-piperidine-1-carboxylic acid tert-butyl ester

From thiophene (130 mg) and 4-formyl-piperidine-1-carboxylic acid tert-butyl ester (300 mg) by procedure D. Yield: 167 mg (40%). Yellow oil. MS (m/z): 298.1 ([M+H]$^+$).

Step 2

4-(Thiophene-2-carbonyl)-piperidine-1-carboxylic acid tert-butyl ester

From 4-(hydroxy-thiophen-2-yl-methyl)-piperidine-1-carboxylic acid tert-butyl ester (127 mg) by procedure E.1. Yield: 117 mg (93%). Yellow oil. MS (m/z): 296.2 ([M+H]$^+$).

Step 3

Piperidin-4-yl-thiophen-2-yl-methanone hydrochloride

From 4-(thiophene-2-carbonyl)-piperidine-1-carboxylic acid tert-butyl ester (115 mg) by procedure B.2. Yield: 74 mg (82%). Yellow solid. MS (m/z): 196.0 ([M+H]$^+$).

Step 4

N-(trans-4-{2-[4-(Thiophene-2-carbonyl)-piperidin-1-yl]-ethyl}-cyclohexyl)-acetamide From piperidin-4-yl-thiophen-2-yl-methanone hydrochloride (74 mg) and N-[trans-4-(2-oxo-ethyl)-cyclohexyl]-acetamide (64 mg, intermediate AG). Yield: 75 mg (65%). Light yellow solid. MS (m/z): 363.4 ([M+H]⁺).

Example 82

(R,S)-Chroman-3-carboxylic acid (trans-4-{2-[4-(3-chloro-thiophene-2-carbonyl)-piperidin-1-yl]-ethyl}-cyclohexyl)-amide

Step 1

4-[(3-Chloro-thiophen-2-yl)-hydroxy-methyl]-piperidine-1-carboxylic acid tert-butyl ester From 3-chlorothiophene (612 mg) and 4-formyl-piperidine-1-carboxylic acid tert-butyl ester (1.00 g) by procedure D. Yield: 420 mg (27%). Yellow solid. MS (m/z): 332.2 ([M+H]⁺).

Step 2

4-(3-Chloro-thiophene-2-carbonyl)-piperidine-1-carboxylic acid tert-butyl ester

From 4-[(3-chloro-thiophen-2-yl)-hydroxy-methyl]-piperidine-1-carboxylic acid tert-butyl ester (420 mg) by procedure E.2. Yield: 255 mg (61%). Light yellow oil. MS (m/z): 330.2 ([M+H]⁺).

Step 3

(3-Chloro-thiophen-2-yl)-piperidin-4-yl-methanone hydrochloride

From 4-(3-chloro-thiophene-2-carbonyl)-piperidine-1-carboxylic acid tert-butyl ester (255 mg) by procedure B.2. Yield: 178 mg (86%). White solid. MS (m/z): 230.4 ([M+H]⁺).

Step 4

(trans-4-{2-[4-(3-Chloro-thiophene-2-carbonyl)-piperidin-1-yl]-ethyl}-cyclohexyl)-carbamic acid tert-butyl ester From (3-chloro-thiophen-2-yl)-piperidin-4-yl-methanone hydrochloride (100 mg) and [trans-4-(2-oxo-ethyl)-cyclohexyl]-carbamic acid tert-butyl ester (intermediate C, 91 mg) by procedure A.1. Yield: 85 mg (50%). White foam. MS (m/z): 455.3 ([M+H]⁺).

Step 5

{1-[2-(trans-4-Amino-cyclohexyl)-ethyl]-piperidin-4-yl}-(3-chloro-thiophen-2-yl)-methanone dihydrochloride From (trans-4-{2-[4-(3-Chloro-thiophene-2-carbonyl)-piperidin-1-yl]-ethyl}-cyclohexyl)-carbamic acid tert-butyl ester (85 mg) by procedure B.2. Yield: 60 mg (75%). White solid. MS (m/z): 355.3 ([M+H]⁺).

Step 6

(R,S)-Chroman-3-carboxylic acid (trans-4-{2-[4-(3-chloro-thiophene-2-carbonyl)-piperidin-1-yl]-ethyl}-cyclohexyl)-amide From {1-[2-(trans-4-amino-cyclohexyl)-ethyl]-piperidin-4-yl}-(3-chloro-thiophen-2-yl)-methanone dihydrochloride (30 mg) and (R,S)-chromanecarboxylic acid by procedure C. Yield: 1 mg (2.7%). White solid. MS (m/z): 515.3 ([M+H])⁺.

Example 83

N-(trans-4-{2-[4-(3-Chloro-thiophene-2-carbonyl)-piperidin-1-yl]-ethyl}-cyclohexyl)-acetamide From (3-chloro-thiophen-2-yl)-piperidin-4-yl-methanone hydrochloride (78 mg) and N-[trans-4-(2-oxo-ethyl)-cyclohexyl]-acetamide (54 mg, intermediate AG) by procedure A.1. Yield: 52 mg (45%). White solid. MS (m/z): 397.1 ([M+H]⁺).

Example 84

N-(trans-4-{2-[4-(5-Chloro-thiophene-2-carbonyl)-piperidin-1-yl]-ethyl}-cyclohexyl)-acetamide

Step 1

4-[(5-Chloro-thiophen-2-yl)-hydroxy-methyl]-piperidine-1-carboxylic acid tert-butyl ester From 2-chlorothiophene (183 mg) and 4-formyl-piperidine-1-carboxylic acid tert-butyl ester (300 mg) by procedure D. Yield: 180 mg (38%). Brown oil. MS (m/z): 332.1 ([M+H])⁺.

Step 2

4-(5-Chloro-thiophene-2-carbonyl)-piperidine-1-carboxylic acid tert-butyl ester

From 4-[(5-chloro-thiophen-2-yl)-hydroxy-methyl]-piperidine-1-carboxylic acid tert-butyl ester (20 mg) by procedure E.1. Yield: 18 mg (90%). Yellow oil. MS (m/z): 330.2 ([M+H]⁺).

Step 3

(5-Chloro-thiophen-2-yl)-piperidin-4-yl-methanone hydrochloride

From 4-(5-chloro-thiophene-2-carbonyl)-piperidine-1-carboxylic acid tert-butyl ester (12 mg) by procedure B.2. Yield: 10 mg (100%). White solid. MS (m/z): 230.3 ([M+H]⁺).

Step 4

N-(trans-4-{2-[4-(5-Chloro-thiophene-2-carbonyl)-piperidin-1-yl]-ethyl}-cyclohexyl)-acetamide From (5-chloro-thiophen-2-yl)-piperidin-4-yl-methanone hydrochloride (10 mg) and N-[trans-4-(2-oxo-ethyl)-cyclohexyl]-acetamide (7 mg, intermediate AG) by procedure A.1. Yield: 9 mg (59%). White solid. MS (m/z): 397.4 ([M+H]⁺).

Example 85

Benzo[1,3]dioxole-5-carboxylic acid (trans-4-{2-[4-(5-chloro-thiophene-2-carbonyl)-piperidin-1-yl]-ethyl}-cyclohexyl)-amide

Step 1

(trans-4-{2-[4-(5-chloro-thiophene-2-carbonyl)-piperidin-1-yl]-ethyl}-cyclohexyl)-carbamic acid tert-butyl ester From (5-chloro-thiophen-2-yl)-piperidin-4-yl-methanone hydrochloride (585 mg) and [trans-4-(2-oxo-ethyl)-cyclohexyl]-carbamic acid tert-butyl ester (intermediate C, 530 mg) by procedure A.2. Yield: 513 mg (51%). Light yellow solid. MS (m/z): 455.2 ([M+H]$^+$).

Step 2

{1-[2-(trans-4-Amino-cyclohexyl)-ethyl]-piperidin-4-yl}-(5-chloro-thiophen-2-yl)-methanone dihydrochloride From (trans-4-{2-[4-(5-chloro-thiophene-2-carbonyl)-piperidin-1-yl]-ethyl}-cyclohexyl)-carbamic acid tert-butyl ester (1.14 g) by procedure B.1. Yield: 970 mg (91%). Light grey solid. MS (m/z): 355.1 ([M+H]$^+$).

Step 3

Benzo[1,3]dioxole-5-carboxylic acid (trans-4-{2-[4-(5-chloro-thiophene-2-carbonyl)-piperidin-1-yl]-ethyl}-cyclohexyl)-amide From {1-[2-(trans-4-amino-cyclohexyl)-ethyl]-piperidin-4-yl}-(5-chloro-thiophen-2-yl)-methanone dihydrochloride (100 mg) and benzo[1,3]dioxole-5-carboxylic acid (45 mg) by procedure C. Yield: 62 mg (52%). Off-white solid. MS (m/z): 503.2 ([M+H]$^+$).

Example 86

N-(trans-4-{2-[4-(5-Fluoro-thiophene-2-carbonyl)-piperidin-1-yl]-ethyl}-cyclohexyl)-acetamide Step 1

4-[(5-Fluoro-thiophen-2-yl)-hydroxy-methyl]-piperidine-1-carboxylic acid tert-butyl ester A 1.6 M solution of n-BuLi in Hex (3.71 ml, 5.9 mmol) was added to a cooled (−78° C.) solution of thiophene (500 mg, 5.9 mmol) in THF (15 ml) under Ar. After stirring 30 min at −78° C. a solution of N-fluorodibenzenesulfonimide (1.87 g, 5.9 mmol) in THF (10 ml) was added. Stirring at −78° C. was continued for 10 min before slow rising of the temperature to 0° C. over a period of 15 min. A solid precipitate was formed. The mixture was cooled to −78° C., a 1.6 M n-BuLi solution in Hex (3.71 ml, 0.59 ml) was added, then it was stirred 10 min before addition of 4-formyl-piperidine-1-carboxylic acid tert-butyl ester (836 mg, 3.9 mmol) in THF (5 ml). After stirring 30 min at −78° C. the solution was slowly warmed to room temperature. Sat. aq. NH$_4$Cl sol. (5 ml) was added, the mixture was diluted with EtOAc (100 ml) and washed with sat. aq. NH$_4$Cl sol. (100 ml), sat. aq. NaHCO$_3$ (2×100 ml) and brine (100 ml). After drying (Na$_2$SO$_4$) and evaporation of the solvent, the crude product was purified by chromatography (amino modified silica gel, Hept to EtOAc) to yield 971 mg (79%) of a brown oil. MS (m/z): 316.1 ([M+H]$^+$).

Step 2

4-(5-Fluoro-thiophene-2-carbonyl)-piperidine-1-carboxylic acid tert-butyl ester

From 4-[(5-fluoro-thiophen-2-yl)-hydroxy-methyl]-piperidine-1-carboxylic acid tert-butyl ester (968 mg) by procedure E.2. MeCN (0.6 ml) was added to the reaction mixture. Yield: 577 mg (60%). Light brown gum. MS (m/z): 336.4 ([M+Na]$^+$).

Step 3

(5-Fluoro-thiophen-2-yl)-piperidin-4-yl-methanone hydrochloride

From 4-(5-fluoro-thiophene-2-carbonyl)-piperidine-1-carboxylic acid tert-butyl ester (51 mg) by procedure B.1. Yield: 20 mg (49%). Off-white solid. MS (m/z): 214.1 ([M+H]$^+$).

Step 4

N-(trans-4-{2-[4-(5-Fluoro-thiophene-2-carbonyl)-piperidin-1-yl]-ethyl}-cyclohexyl)-acetamide From (5-fluoro-thiophen-2-yl)-piperidin-4-yl-methanone hydrochloride (17 mg) and N-[trans-4-(2-oxo-ethyl)-cyclohexyl]-acetamide (20 mg, intermediate AG) by procedure A.2. Yield: 19 mg (73%). White solid. MS (m/z): 381.3 ([M+H]$^+$).

The following Examples A to E are prophetic.

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

Capsule Contents

| | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |

Gelatin Capsule

| | |
|---|---|
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

The invention claimed is:

1. A compound of formula (I):

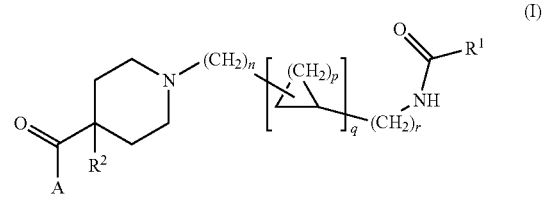

wherein:

A is aryl optionally substituted by one to five substituents selected from the group consisting of halo, $C_{1-6}$-alkyl and $C_{1-6}$-alkoxy;

n is 2;
p is 4;
q is 1;
r is 0;

$R^1$ is 5 to 10 membered heterocycloalkyl optionally substituted by one or more $R^a$,
wherein $R^a$ is selected from:
halo,
cyano,
oxo,
hydroxy,
halobenzenesulfonyl,
$C_{1-6}$-alkyl optionally substituted by one, two or three substitutents selected from the group consisting of:
5 to 6 membered heterocycloalkyl, and
aryl which is optionally substituted by halo or by $C_{1-6}$-alkoxy,
$C_{1-6}$-haloalkyl,
$C_{1-6}$-haloalkoxy,
$C_{1-6}$-alkoxy optionally substituted by aryl or by 5 to 6 membered heteroaryl each of which is optionally substituted by $C_{1-6}$-alkyl,
aryloxy,
—NH(CO)—$C_{1-6}$-alkyl,
—O(CO)—$C_{1-6}$-alkyl,
$C_{1-6}$-alkylsulfonyl,
aryl,
5 to 6 membered heterocycloalkyl optionally substituted by hydroxy, $C_{1-6}$-alkyl or oxo,
5 to 6 membered heteroaryl optionally substituted by $C_{1-6}$-alkyl or oxo, and
di($C_{1-6}$)alkylamino; and $R^2$ is H, OH, $C_{1-6}$-alkyl or halo;

or a pharmaceutically acceptable salt thereof.

2. The compound of claim 1 having formula (Ia):

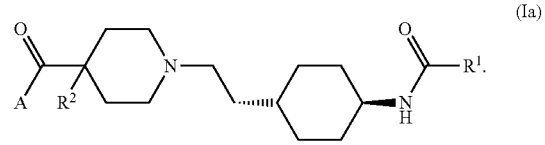

3. The compound of claim 2, selected from the group consisting of:

Tetrahydro-pyran-4-carboxylic acid trans-(4-{2-[4-(4-fluoro-benzoyl)-piperidin-1-yl]-ethyl}-cyclohexyl)-amide;

Tetrahydro-furan-3-carboxylic acid trans-(4-{2-[4-(4-fluoro-benzoyl)-piperidin-1-yl]-ethyl}-cyclohexyl)-amide;

Morpholine-4-carboxylic acid trans-(4-{2-[4-(4-fluoro-benzoyl)-piperidin-1-yl]-ethyl}-cyclohexyl)-amide 3-Phenoxy-pyrrolidine-1-carboxylic acid trans (4-{2-[4-(4-fluoro-benzoyl)-piperidin-1-yl]-ethyl}-cyclohexyl)-amide 1,1-Dioxo-thiomorpholine-4-carboxylic acid trans (4-{2-[4-(4-fluoro-benzoyl)-piperidin-1-yl]-ethyl}-cyclohexyl)-amide Tetrahydro-furan-3-carboxylic acid trans-(4-{2-[4-fluoro-4-(4-fluoro-benzoyl)-piperidin-1-yl]-ethyl}-cyclohexyl)-amide Tetrahydro-furan-3-carboxylic acid trans-(4-{2-[4-(2,4-difluoro-benzoyl)-piperidin-1-yl]-ethyl}-cyclohexyl)-amide (S)-Tetrahydro-furan-3-carboxylic acid (4-{2-[4-(2,4-difluoro-benzoyl)-piperidin-1-yl]-ethyl}-cyclohexyl)-amide; and (R)-Tetrahydro-furan-3-carboxylic acid (4-{2-[4-(2,4-difluoro-benzoyl)-piperidin-1-yl]-ethyl}-cyclohexyl)-amide.

4. The compound of claim 2, selected from the group consisting of:

4-Phenyl-piperazine-1-carboxylic acid trans (4-{2-[4-(2,4-difluoro-benzoyl)-piperidin-1-yl]-ethyl}-cyclohexyl)-amide;

Morpholine-4-carboxylic acid (4-{2-[4-(2,4-difluoro-benzoyl)-piperidin-1-yl]-ethyl}-cyclohexyl)-amide;

Pyrrolidine-1-carboxylic acid (4-{2-[4-(2,4-difluoro-benzoyl)-piperidin-1-yl]-ethyl}-cyclohexyl)-amide;

Tetrahydro-furan-3-carboxylic acid trans (4-{2-[4-(3,4-difluoro-benzoyl)-piperidin-1-yl]-ethyl}-cyclohexyl)-amide;

Tetrahydro-pyran-4-carboxylic acid (4-{2-[4-(3,4-difluoro-benzoyl)-piperidin-1-yl]-ethyl}-cyclohexyl)-amide Tetrahydro-furan-3-carboxylic acid trans (4-{2-[4-(2-chloro-4-fluoro-benzoyl)-piperidin-1-yl]-ethyl}-cyclohexyl)-amide;

Tetrahydro-pyran-4-carboxylic acid (4-{2-[4-(2-chloro-4-fluoro-benzoyl)-piperidin-1-yl]-ethyl}-cyclohexyl)-amide; and Tetrahydro-pyran-4-carboxylic acid (trans-4-{2-[4-(4-chloro-benzoyl)-piperidin-1-yl]-ethyl}-cyclohexyl)-amide.

5. A pharmaceutical composition comprising a therapeutically effective amount of a compound of formula (I)

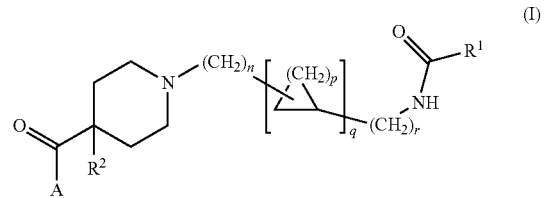

wherein:

A is aryl optionally substituted by one to five substituents selected from the group consisting of halo, $C_{1-6}$-alkyl and $C_{1-6}$-alkoxy;

n is 2;

p is 4;

q is 1;

r is 0;

$R^1$ is 5 to 10 membered heterocycloalkyl optionally substituted by one or more $R^a$, wherein $R^a$ is selected from:
halo,
cyano,
oxo,
hydroxy,
halobenzenesulfonyl,
$C_{1-6}$-alkyl optionally substituted by one, two or three substitutents selected from the group consisting of:
5 to 6 membered heterocycloalkyl, and
aryl which is optionally substituted by halo or by $C_{1-6}$-alkoxy,
$C_{1-6}$-haloalkyl,
$C_{1-6}$-haloalkoxy,
$C_{1-6}$-alkoxy optionally substituted by aryl or by 5 to 6 membered heteroaryl each of which is optionally substituted by $C_{1-6}$-alkyl,
aryloxy,
—NH(CO)—$C_{1-6}$-alkyl,
—O(CO)—$C_{1-6}$-alkyl,
$C_{1-6}$-alkylsulfonyl,
aryl,
5 to 6 membered heterocycloalkyl optionally substituted by hydroxy, $C_{1-6}$-alkyl or oxo,
5 to 6 membered heteroaryl optionally substituted by $C_{1-6}$-alkyl or oxo, and
di($C_{1-6}$)alkylamino; and $R^2$ is H, OH, $C_{1-6}$-alkyl or halo;

or a pharmaceutically acceptable salt thereof and a pharmaceutically acceptable carrier.

* * * * *